(12) United States Patent
Davis et al.

(10) Patent No.: US 7,317,087 B2
(45) Date of Patent: Jan. 8, 2008

(54) MEMBERS OF THE FC RECEPTOR HOMOLOG GENE FAMILY (FCRH1-3, 6), RELATED REAGENTS, AND USES THEREOF

(75) Inventors: Randall S. Davis, Birmingham, AL (US); Max D. Cooper, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/508,374

(22) PCT Filed: Mar. 25, 2003

(86) PCT No.: PCT/US03/09600

§ 371 (c)(1),
(2), (4) Date: Mar. 25, 2005

(87) PCT Pub. No.: WO03/089624

PCT Pub. Date: Oct. 30, 2003

(65) Prior Publication Data

US 2005/0240006 A1    Oct. 27, 2005

Related U.S. Application Data

(60) Provisional application No. 60/367,667, filed on Mar. 25, 2002.

(51) Int. Cl.
*C07K 14/00* (2006.01)
(52) U.S. Cl. .................................................. 530/350
(58) Field of Classification Search .................... None
See application file for complete search history.

(56) References Cited

U.S. PATENT DOCUMENTS

| 4,342,566 A | 8/1982 | Theofilopoulos |
| 4,816,567 A | 3/1989 | Cabilly |
| 4,868,116 A | 9/1989 | Morgan |
| 4,980,286 A | 12/1990 | Morgan |
| 2003/0078396 A1 | 4/2003 | Gaiger et al. |

FOREIGN PATENT DOCUMENTS

| WO | WO 89/07136 | | 8/1989 |
| WO | WO 90/02806 | | 3/1990 |
| WO | WO 94/04679 | | 3/1994 |
| WO | WO 94/29348 | | 12/1994 |
| WO | WO 01/38490 | * | 5/2001 |
| WO | WO 01/38490 A2 | | 5/2001 |

OTHER PUBLICATIONS

Alizadeh, et al. "Distinct types of diffuse large B-cell lymphoma identified by gene expression profiling." Nature. Feb. 3, 2000;403(6769):503-11.
Arnon et al. "The mechanisms controlling the recognition of tumor- and virus-infected cells by NKp46." Blood. Jan. 15, 2004;103(2):664-72.
Borges, L. et al. "A family of human lymphoid and myeloid Ig-like receptors, some of which bind to MHC class I molecules." J Immunol. Dec. 1, 1997;159(11):5192-6.
Bork, P. et al. "The immunoglobulin fold. Structural classification, sequence patterns and common core." J Mol Biol. Sep. 30, 1994;242(4):309-20.
Daeron, M. "Fc receptor biology." Annu Rev Immunol. 1997;15:203-34.
Davis et al. "Definition of an Fc receptor-related gene (FcRX) expressed in human and mouse B cells." Int Immunol. Sep. 2002;14(9):1075-83.
Davis et al. "Fc receptor homologs (FcRH1-5) extend the Fc receptor family." Curr Top Microbiol Immunol. 2002;266:85-112.
Davis et al. "Fc receptor homologs: newest members of a remarkably diverse Fc receptor gene family." Immunol Rev. Dec. 2002;190:123-36.
Davis et al. "Identification of a family of Fc receptor homologs with preferential B cell expression." Proc Natl Acad Sci U S A. Aug. 14, 2001;98(17):9772-7.
Davis et al "Differential B cell expression of mouse Fc receptor homologs." Int Immunol. Sep. 2004;16(9):1343-53.
Dennis, G. et al. "Paired Ig-like receptor homologs in birds and mammals share a common ancestor with mammalian Fc receptors." Proc Natl Acad Sci U S A. Nov. 21, 2000;97(24):13245-50.
Ehrhardt et al. "The inhibitory potential of Fc receptor holog4 on memory cells." PNAS 100:13489-13494.
Findley, H. W. et al. "Two new acute lymphoblastic leukemia cell lines with early B-cell phenotypes." Blood. Dec. 1982;60(6):1305-9.
Gergely, J. et al. "Immunoreceptor tyrosine-based inhibition motif-bearing receptors regulate the immunoreceptor tyrosine-based activation motif-induced activation of immune competent cells." Immunol Lett. May 3, 1999;68(1):3-15.
Hatzivassiliou, G. et al. "IRTA1 and IRTA2, novel immunoglobulin superfamily receptors expressed in B cells and involved in chromosome 1q21 abnormalities in B cell malignancy." Immunity. Mar. 2001;14(3):277-89.
Hayami, K. et al. "Molecular cloning of a novel murine cell-surface glycoprotein homologous to killer cell inhibitory receptors." J Biol Chem. Mar. 14, 1997;272(11):7320-7.

(Continued)

*Primary Examiner*—Maher M. Haddad
*Assistant Examiner*—Chun Crowder
(74) *Attorney, Agent, or Firm*—Fish & Richardson P.C.

(57) ABSTRACT

The invention relates to members of the Fc receptor homolog (FcRH) subfamily, as well as fragments and variants thereof. Each FcRH is a Type I transmembrane receptor, preferably, comprises an extracellular region, a transmembrane region, and a cytoplasmic region. The cytoplasmic region preferably comprises one or more immunoreceptor tyrosine-based inhibitory or activation motifs ("ITIMs" or "ITAMs). The invention provides polypeptides, nucleic acids, vectors, expression systems, and antibodies and antibody fragments related to the FcRHs as well as uses thereof. Such uses include uses in the diagnosis and treatment of a malignancy of hematopoietic cell lineage or an inflammatory or autoimmune disease in a subject and in the modulation of a humoral immune response in a subject.

1 Claim, 10 Drawing Sheets

OTHER PUBLICATIONS

Higgins, D. G. & Sharp, P. M. "Fast and sensitive multiple sequence alignments on a microcomputer." Comput Appl Biosci. Apr. 1989;5(2):151-3.

Jones et al. "Replacing the complementarity-determining regions in a human antibody with those from a mouse." Nature. May 29-Jun. 4, 1986;321(6069):522-5.

Klein, E. et al. "Surface IgM-kappa specificity on a Burkitt lymphoma cell in vivo and in derived culture lines." Cancer Res. Jul. 1968;28(7):1300-10.

Klein, G. et al. "An EBV-genome-negative cell line established from an American Burkitt lymphoma; receptor characteristics. EBV infectibility and permanent conversion into EBV-positive sublines by in vitro infection." Intervirology. 1975;5(6):319-34.

Korsmeyer, S. J. et al. "Immunoglobulin gene rearrangement and cell surface antigen expression in acute lymphocytic leukemias of T cell and B cell precursor origins." J Clin Invest. Feb. 1983;71(2):301-13.

Kremer, E. J. et al. "The gene for the human IgA Fc receptor maps to 19q13.4." Hum Genet. Apr. 1992;89(1):107-8.

Kubagawa, H. et al. "A novel pair of immunoglobulin-like receptors expressed by B cells and myeloid cells." Proc Natl Acad Sci U S A. May 13, 1997;94(10):5261-6.

Kulczycki, A., Jr. et al.. "Genomic organization of mouse Fc gamma receptor genes." Proc Natl Acad Sci U S A. Apr. 1990;87(7):2856-60.

Leu et al. "FcRH1: an activation co-receptor on human B cells" Blood First Ed. Paper, prepublished online Oct. 12, 2004: DOI 10.1182/blood-2004-06-2344.

Lonberg And Huszar "Human antibodies from transgenic mice." Int Rev Immunol. 1995;13(1):65-93.

Long, E. O. "Regulation of immune responses through inhibitory receptors." Annu Rev Immunol. 1999;17:875-904.

Martin, D. et al. "Induced rearrangement of kappa genes in the BLIN-1 human pre-B cell line correlates with germline J-C kappa and V kappa transcription." J Exp Med. Mar. 1, 1991;173(3):639-45.

Miller et al. "IRTAs: a new family of immunoglobulinlike receptors differentially expressed in B cells." Blood. Apr. 15, 2002;99(8):2662-9.

Monteiro et al. "Molecular heterogeneity of Fc alpha receptors detected by receptor-specific monoclonal antibodies." J Immunol. Mar. 15, 1992;148(6):1764-70.

Morrison et al., "Chimeric human antibody molecules: mouse antigen-binding domains with human constant region domains." Proc Natl Acad Sci U S A. Nov. 1984;81(21):6851-5.

Morton, E. C. et al. "Functional association between the human myeloid immunoglobulin A Fc receptor (CD89) and FcR gamma chain. Molecular basis for CD89/FcR gamma chain association." J Biol Chem. Dec. 15, 1995;270(50):29781-7.

Pang, J. et al.. "Characterization of the gene for the high affinity TgE receptor (Fc epsilon RI) alpha chain" J. Immunol. 151:6166-6174 (1994).

Pascual et al. "Analysis of somatic mutation in five B cell subsets of human tonsil." J Exp Med. Jul. 1, 1994;180(1):329-39.

Pfefferkom, L. C. & Yeaman, G. R. "Association of IgA-Fc receptors (Fc alpha R) with Fc epsilon RI gamma 2 subunits in U937 cells. Aggregation induces the tyrosine phosphorylation of gamma 2." J Immunol. Oct. 1, 1994;153(7):3228-36.

Ravetch, & Kinet, "Fc receptors." Annu Rev Immunol. 1991;9:457-92.

Ravetch& Bolland, "IgG Fc receptors." Annu Rev Immunol. 2001;19:275-90.

Ravetch & Lanier, "Immune inhibitory receptors." Science. Oct. 6, 2000;290(5489):84-9.

Reth, M. "Antigen receptors on B lymphocytes." Annu Rev Immunol. 1992;10:97-121.

Samaridis, J. & Colonna, M. "Cloning of novel immunoglobulin superfamily receptors expressed on human myeloid and lymphoid cells: structural evidence for new stimulatory and inhibitory pathways." Eur J Immunol. Mar. 1997;27(3):660-5.

Sonnhammer et al. "A hidden marker model for predicting transmembrane helices in protein sequences" eds. Glasgo, Little John, Marore et al. Am. Associate of Artificial Intelligence pp. 175-182.

Unkeless, J. C. & Jin, J. "Inhibitory receptors, ITIM sequences and phosphatases." Curr Opin Immunol. Jun. 1997;9(3):338-43.

Van De Winkel & Capel, "Human IgG Fc receptor heterogeneity: molecular aspects and clinical implications." Immunol Today. May 1993;14(5):215-21.

Vaughn and Bjorkman "The (Greek) key to structures of neural adhesion molecules." Neuron. Feb. 1996;16(2):261-73.

Vely, F. & Vivier, E "Conservation of structural features reveals the existence of a large family of inhibitory cell surface receptors and noninhibitory/activatory counterparts." J Immunol. Sep. 1, 1997;159(5):2075-7.

Verhoeyen et al. "Reshaping human antibodies: grafting an antilysozyme activity." Science. Mar. 25, 1988;239(4847):1534-6.

Wagtmann, N. et al. "A new human gene complex encoding the killer cell inhibitory receptors and related monocyte/macrophage receptors." Curr Biol. Aug. 1, 1997;7(8):615-8.

Wende, H. et al. "Organization of the leukocyte receptor cluster (LRC) on human chromosome 19q13.4." Mamm Genome. Feb. 1999;10(2):154-60.

Williams & Barclay. "The immunoglobulin superfamily—domains for cell surface recognition." Annu Rev Immunol. 1988;6:381-405.

Wilson, et al. "Plasticity in the organization and sequences of human KIR/ILT gene families." Proc Natl Acad Sci U S A. Apr. 25, 2000;97(9):4778-83.

Yoder et al. "Immune-type receptor genes in zebrafish share genetic and functional properties with genes encoded by the mammalian leukocyte receptor cluster." Proc Natl Acad Sci U SA. Jun. 5, 2001;98(12):6771-6.

Davis, R.S., et al. "Identification of a Family of Fc Receptor Homologs with Preferential B Cell Expression", PNAS, Aug. 14, 2001, vol. 98, No. 17, pp. 9772-9777.

Davis, R.S., et al., "Fc Receptor Homologs: Newest Members of a Remarkably Diverse FC Receptor Gene Family", Immunological Reviews, 2002, vol. 190, pp. 123-136.

Kant, A.M., et al. "Heterogeneity in the Expression of FcgammaRIII in Morphologically Mature Granuleocytes from Patients with Chronic Myeloid Leukemia", Leukemia Research, Mar. 1997, vol. 21, No. 3, pp. 225-234.

Morton, H.C., et al. Structure and Function of Human IgA Fc Receptors (FcalphaR). Critical Reviews in Immunology, 1996, vol. 16, No. 4, pp. 423-440.

Morton, H.C., et al. "Alternatively Spliced Forms of the Human Myeloid Fcalpha Receptor (CD89) in Neurtrophils", Immunogenics, 1996, vol. 43, No. 4, pp. 246-247.

Carlsson et al. "Expression of FcgammaRIII Defines Distinct Subpopulations of Fetal Liver B Cell and Myeloid Precursors", Eur J Immunol., Aug. 1995, vol. 23, No. 8, pp. 2308-2317.

* cited by examiner

```
SP.
FcRH3  MLWLLLLIL TPGREQS--              (17)
FcRH2  ...S..V.F DAVT..ADS              (19)
FcRH1  ..PR.....C A.LC.P---             (16)

EC1
FcRH3  GVAPKAVLLL NPPWSTAFKG EKVALICSGI SHSLAQGDTY WYHDEKLLKI KHDKIQITEP GNYQCKTRGS SLSDAVHVEF SP     (82)
FcRH2  ---------- ---------- ---------- ---------- ---------- ---------- ---------- ---------- --
FcRH1  ---------- ---------- ---------- ---------- ---------- ---------- ---------- ---------- --

EC2
FcRH3  DALIQALHP VFEGDNVILR CQGKDNKNTH QKVYYKDGKQ LPNSYMLERI TVNS-VSRDN SKYHCTAYRK FYILDIEVTS KPLNIQVQ  (87)
FcRH2  --T.V.PSS .....SIVLK ...EQ.WKIQ KWA.H..N.E .SVFKKFSDF LIQ.A.LS.S GN.F.STKGQ LFLW.K-.. NIVK.K..  (84)
FcRH1  ---------- ---------- ---------- ---------- ---------- ---------- ---------- ---------- --------

EC3
FcRH3  -ELFLHPVLR ASSSTPIEGS PMTLTGETQL SPQRPDVQLQ FSLFRDSQTL GLGWSRSPRL QIPAMWTEDS GSYNCEVETV THSIKKRSLRS QIRVQ-   (95)
FcRH2  -...QR...T ....FQ....G .VS.K..R.. .....CF.EN.V. S..S.E. ..S.V.S.T .......KA... .R.R.Q..Q. ..H.R    (95)
FcRH1  A...--..-I ..P.H.T... .V....KMPF L-.SS.A.F. .CF...TRA. .P..S.K. .A..K.T ......AQ.M ASKVLR-.R. ..N.H-  (90)

EC4
FcRH3  RVPVSNWLE IRPTGEQLIE GENMWLICSV AQGSGTVTFS WHKEGRVRSL GRKTQPSLLA ELHVLTVKES DAGRYYCAAD NVHSPILSTW IRVTVR    (96)
FcRH2  -I.I..S... ..AP..VT.. .QKLILL... ...G.T.N.. ..YR.ATGT.M K......S. ...EIPA... ..K..R. .G.V..Q.KV VHIP..    (95)
FcRH1  ...AD.S... TQ.P...VM. .DRL...... ...M.T.DI.L .Y.GAVGLN. QS......T. .YEIPS.R.. ...EQ..V.E .GYG.SP.GL VSI...   (96)

EC5
FcRH3  IPVSHPVLTF RAPRAHTVWG DLLELHCESL RGSPPILYRF YHEDVTLGNS SAPSGGGASF NLSLTAEHSG NYSCDADNGL GAQHSHGVSL RVT     (93)
FcRH2  ....R....L .S.G.QAA.. .......... ..........Q. ..........    ----........ .......... ....E.H... ...C.EA.PV SIS     (93)
FcRH1  ....R.I.ML .....QAA.E .V........ ..........W. ...I..SR.    ---........ .......... ....E.N... ...R.EA.T. NE.     (93)

EC6
FcRH3  VPVSRPVLTL RAPGAQAVVG DLLELHCESL RGSFPILYWF YHEDDTLGNI SARSGGGASF NLSLTTEHSG NYSCEADNGL GAQHSKVVTL NVI     (93)
FcRH2  ---------- ---------- ---------- ---------- ---------- ---------- ---------- ---------- ---
FcRH1  ---------- ---------- ---------- ---------- ---------- ---------- ---------- ---------- ---
```

FIG.2B-1

```
MP-TM
FcRH3    ---GTSRMRT GLTAAGITGL VLSILVLAAA AALL------ -------YALF   (31)
FcRH2    GPD.YR.DL- -M..GVLN.. -FGV.GFTGV ---------- ---.L-FCYGL   (36)
FcRH1    VPT.ARS.H- -...SGV.E. -...T.GP.TV ---------- ---L-FCYGL-   (35)

CY
FcRH3    HYARARRKPG GLSATGTSSH SPSECQEPSS SRPSRIDPQE ELEPMYSNVN PGDSNPIYSQ IWSIQHTKEN SANCPWHQE HEELTVLYSE   (86)
FcRH2    HKISGESSAT NEPRGASRPN PQEFTYSSPT PQMEELQPVY VMWGSVDVDV VYSQMSMQQ PESSANIRTL LENKDSQVIY SSVKKS       (99)
FcRH1    KRKIGRRSAR DPLRSLPSPL PQEFTYLNSP TPGQLQPIYE NVNWSGDEG YSLAYYNQPE QESVAAETLG THMEDKVSLD IYSRLRKANI TDVDYEDAM (140)

FcRH3    LKKTHPDDSA GEASSRGRAH EDDEBNYEN VPRVLLASDH        (140)
```

FIG. 2B-2

Comparison of Tyrosine Based Motifs in
FcRH Cytoplasmic Tails

```
         1                                                                                          80
huFcRH1  ---KRKIGRRSARDPLRS---------------LPSPLPQEFTYLNSPTP-GQLQPIYENVNVVSGDEVYSLAYYNQPEQE
huFcRH2  H--------KISGESSATNEPRG---------ASRPNPQEFTYSSPTPDMEELQPVYYNVGSVDVDVYSQIWSMQQPES
huFcRH3  HYARARRKPGGLSATGTSSHSPSECQEPSSSRPSRIDPQEPTHSKPLAPME-LEPMYSNVNPGDSNPIYSQIWSIQHTKE
huFcRH4  HCWRRRKSGVGFLGDETRL------------PPAPGPGESSHSICPAQVE-LQSLYVDVHPKKGDLVYSEIQTTQLGEE
huFcRH5  ----SRKAGRKPASDPARS-------------PSDSDSQEPTYHN-VPAMEELQPVYINANPRGENVIYSEVRIIQEKKK
moFcRH2  ----KRKIGRQSE-DPVRS-------------PPQTVLQGSTYPKSPDS-RQPEPLYENVNVVSGNEVYSLVYHTPQVLE
moFcRH3  ----SRKAGGKPTSDDSRN-------------PSDSEPQEPTYYN-VPACTELQPVYSNE--PEENVIYTEVRRTQPRQK 81
huFcRH1  SVAAETLGTHMED---KVSLDIYSRLRKANITDV------------------DYEDA------M   (99)
huFcRH2  SAN--IRTLLENKDS--------QVIYSSVKK------------------------S  (86)
huFcRH3  NSANCPMMHQEHEEL----TVLYSELKKTHPDDSAGEASSRGRAHEEDDEENYENVPRVLLASDH (140)
huFcRH4  EEANTSRTLLEDKDV-----SVVYSEVKTQHPDNSAGKISSKD-------------EES (107)
huFcRH5  HAVASDPRHLRNKGS-----PIIYSEVKVASTPVSGSLFLASS------------APHR (104)
moFcRH2  PAAAQHVRTHGVSESFQVSSGLYSKPR-INIAHM----------------DYEDA------M  (100)
moFcRH3  HAD--------QESES------PRSRCQM---------------------AEKK  (79)
```

FIG. 5

MEMBERS OF THE FC RECEPTOR HOMOLOG GENE FAMILY (FCRH1-3, 6), RELATED REAGENTS, AND USES THEREOF

This application claims the benefit of U.S. Provisional Application No. 60/367,667, filed Mar. 25, 2002.

ACKNOWLEDGEMENTS

This invention was made with government support under Grants 2R37 and AI39816 awarded by NIAID. The government has certain rights in the invention.

FIELD OF THE INVENTION

This invention relates generally to immunology and modulation of immunologic responses in the context of inflammatory diseases and cancer.

BACKGROUND OF THE INVENTION

Receptors for the Fc region (FcRs) of Igs have broad tissue distribution patterns and can modulate cellular and humoral immunity by linking their antibody ligands with effector cells of the immune system (Ravetch, J. V. & Kinet, J.-P. (1991) Annu. Rev. Immunol. 9, 457-492; Daeron, M. (1997) Annu. Rev. Immunol. 15, 203-234. These cellular receptors have the ability to sense humoral concentrations of antibody, initiate cellular responses in host defense, and participate in autoimmune disorders (Ravetch, J. V. & Bolland, S. (2001) Annu. Rev. Immunol. 19, 275-290). Their diverse regulatory roles depend on the Ig isotype specificity and cellular distribution of the individual FcR. These Ig superfamily members share similarities in their ligand binding subunits, and they may have inhibitory or activating signaling motifs in their intracellular domains or instead pair with signal transducing subunits possessing activating signaling motifs.

Recently, characterization of FcR homologs in mice, the paired Ig-like receptors (Kubagawa, H. et al. (1997) Proc. Natl. Acad. Sci. USA 94, 5261-5266; Hayami, K. et al. (1997) J. Biol. Chem. 272, 7320-7327), and their relatives in humans the Ig-like transcripts/leucocyte Ig-like receptors (Borges, L. et al. (1997) J. Immunol. 159, 5192-5196; Samaridis, J. & Colonna, M. (1997) Eur. J. Immunol. 27, 660-665) have been elucidated. This multigene family, which includes the FcαR (Kremer, E. J. et al. (1992) Hum. Genet. 89, 107-108) and the natural killer cell Ig-like receptors (Wagtmann, N. et al. (1997) Curr. Biol. 7, 615-618), is located in a human chromosome 19q13 region known as the leucocyte receptor complex (LRC) (Wende, H. et al. (1999) Mamm. Genome 10, 154-160; Wilson, M. J. et al. (2000) Proc. Natl. Acad. Sci. USA 97, 4778-4783). These Ig-like multigene families belong to a larger class of receptors characterized by their possession of common cytoplasmic tyrosine-based signaling motifs. These can be either immunoreceptor tyrosine-based activation motifs (ITAMs) containing two repeats of the consensus sequence Y-X-X-L/I spaced by 6-8 amino acids (E/D)-X-X-Y-X-X-(L/I)-$X_{6-8}$-Y-X-X-(L/I) (SEQ ID NO:64, with six amino acid between the consensus sequences; SEQ ID NO:65, with seven amino acid residues between the consensus sequences; and SEQ ID NO:66, with eight amino acid residues between the consensus sequences) or immunoreceptor tyrosine-based inhibitory motifs (ITIMs) with a 6-amino acid consensus sequence (I/V/L/S)-X-Y-X-X-(L/V) (SEQ ID NO:67) (Reth, M. (1992) Annu. Rev. Immunol. 10, 97-121; Vely, F. & Vivier, E. (1997) J. Immunol. 159, 2075-2077; Ravetch, J. V. & Lanier, L. L. (2000) Science 290, 84-89; Gergely, J. et al. (1999) Immunol. Lett. 68, 3-15). The phylogenetic conservation of these types of receptors in birds (Dennis, G. et al. (2000) Proc. Natl. Acad. Sci. USA 97, 13245-13250) and bony fish (Yoder, J. A. et al. (2001) Proc. Natl. Acad. Sci. USA 98, 6771-6717) is indicative of their biological value. After ligand binding of the activating receptor complexes, ITAM tyrosines are rapidly phosphorylated by Src family kinases to initiate a cascade of signaling events that trigger cellular activation. In the case of ITIM-bearing receptors, the tyrosines provide a docking site for phosphatases containing Src homology 2 domains that can abrogate cellular activation (Long, E. O. (1999) Annu. Rev. Immunol. 17, 875-904; Unkeless, J. C. & Jin, J. (1997) Curr. Opin. Immunol. 9, 338-343). The balance in the utilization of these activating and inhibitory receptor pairs can serve to modulate cellular responses to a variety of stimuli.

The genes encoding the classical FcγRs, FcγRI, FcγRII, FcγRIII, and FcεRI, lie on the long arm of chromosome 1 (1q21-23) near the polymeric Ig receptor (pIgR) and Fcα/μR genes (1q32) (20-23). Members of this FcR subfamily have relatively low extracellular homology with the FcR-related genes that reside in the LRC on chromosome 19. Like the FcγR- and FcεR-activating receptors, the ligand binding chain of the FcαR coassociates with the ITAM containing FcR common γ-chain (Pfefferkorn, L. C. & Yeaman, G. P (1994) J. Immunol. 153, 3228-3236; Morton, E. C. et al. (1995) J. Biol. Chem. 270, 29781-29787). New members of the FcR family were sought which could have diverse signally properties and oncogenic potential.

SUMMARY OF THE INVENTION

In accordance with the purpose(s) of this invention, as embodied and broadly described herein, this invention, in one aspect, relates to members of a cluster of FcR and FcR gene relatives encoded, for example, by genes in the human chromosome 1q21-23 region, or analogous region in non-human subjects. The members are Type I transmembrane receptors, or alternatively spliced forms thereof, with homology to the FcR family and are referred to herein as FcRHs. Each FcRH can comprise an extracellular region, a transmembrane region, and a cytoplasmic region. The cytoplasmic region preferably comprises one or more immunoreceptor tyrosine-based inhibitory or activation motifs ("ITIMs" or "ITAMs).

The invention relates to polypeptides corresponding to isolated FcRHs (e.g., huFcRH 1, 2, 3, and 6 and moFcRH1, 2, and 3), as well as fragments and isoforms thereof. The invention further relates to nucleic acids that encode the FcRHs, as well as hybridization probes related thereto and complementary sequences. The invention further provides vectors and cells related to the nucleic acids of the invention.

The invention further relates to making an FcRH, or a fragment or variant thereof, comprising culturing a cell comprising a vector of the invention under conditions permitting expression of the FcRH. The invention also provides an antibody reagent kit comprising the antibody, or a fragment or variant thereof, and reagents for detecting binding of the antibody, fragment, or antibody variant to a ligand.

The invention further relates to uses of the polypeptides, nucleic acids and antibodies of the invention. For example, the invention relates to methods of diagnosing and methods of treating a malignancy of hematopoietic cell lineage or an inflammatory or autoimmune disease in a subject. The invention also relates to modulation of a humoral immune response in a subject.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

FIG. 2 shows the structural and sequence diversity of FcRH1, FcRH2, and FcRH3. FIG. 2B shows the multiple alignment comparison of FcRH1, FcRH2, and FcRH3 amino acid sequences (one-letter code) based on the FcRH3 sequence. Amino acid identity is represented by dots, and gaps are indicated by dashes. Predicted N-linked glycosylation sites and transmembrane domains are underlined in black. Consensus ITAM (bold) and ITIM (bold, underlined) motifs are indicated. Putative structural domains are labeled: SP, signal peptide; EC, extracellular domain; MP-TM, membrane proximal-transmembrane; and CY, cytoplasmic regions. Amino acid lengths are indicated in parentheses.

FIG. 5 shows the multiple alignment comparisons of huFcRH1-5 and mouse FcRH1 and 2 amino acid sequences (one-letter code) based on the FcRH3 sequence. Amino acid gaps are indicated by dashes. Consensus ITAM (underlined) and ITIM (italic, underlined) motifs are indicated. Amino acid lengths are indicated in parentheses.

DESCRIPTION OF THE PREFERRED EMBODIMENTS

Figure 1:
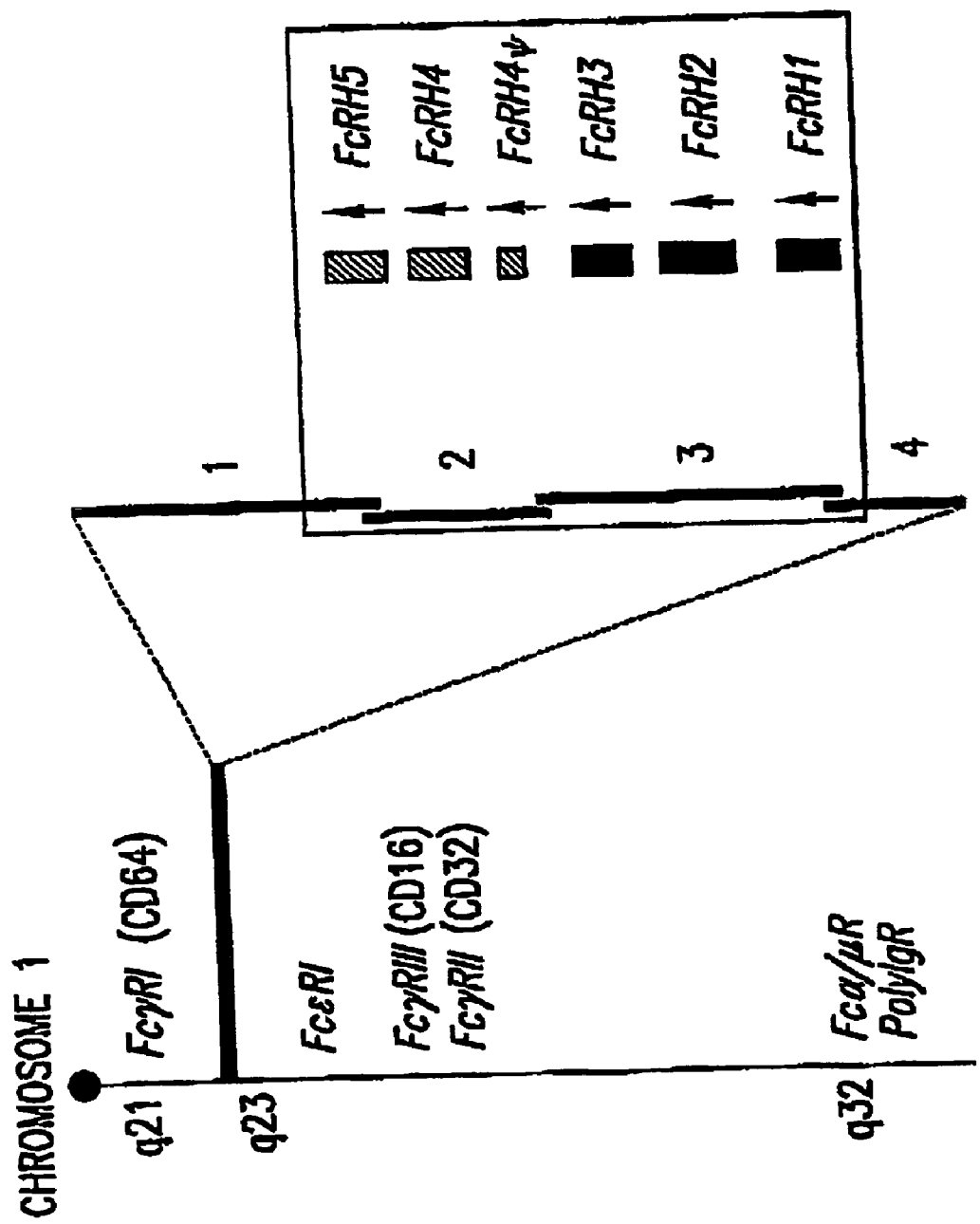
FIG. 1 shows the relative position of the FcRH locus within the FcR cluster on chromosome 1. The cytogenetic location of the FcR genes is approximated from the GenBank Mapview database. The BAC clones (4, GenBank accession no. AL139409; 3, GenBank accession no. AL356276; 2, GenBank accession no. AL135929; and 1, GenBank accession no. AL353721) that span the locus are oriented in relation to their respective FcRH genes (shaded area).

The present invention may be understood more readily by reference to the following detailed description of preferred embodiments of the invention and the Examples included therein and to the Figures and their previous and following description.

In this specification and in the claims that follow, reference will be made to a number of terms that shall be defined to have the following meanings:

As used in the specification and the appended claims, the singular forms "a," "an" and "the" include plural referents unless the context clearly dictates otherwise. Thus, for example, reference to a receptor includes mixtures of various receptors, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally contains two ITAM consensus motifs" means that the two ITAMs may or may not be present and that the description includes both the presence and absence of two ITAM consensus motifs.

As used throughout, by "subject" is meant an individual. Preferably, the subject is a mammal such as a primate, and, more preferably, a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

By "isolated nucleic acid" is meant a nucleic acid the structure of which is not identical to that of the naturally occurring nucleic acid or to that of any fragment of the naturally occurring genomic nucleic acid spanning more than three separate genes. The term therefore covers, for example, (a) a DNA which has the sequence of part of the naturally occurring genomic DNA molecules but is not flanked by both of the coding sequences that flank that part of the molecule in the genome of the organism in which it naturally occurs; (b) a nucleic acid incorporated into a vector or into the genomic DNA of a prokaryote or eukaryote in a maimer such that the resulting molecule is not identical to any naturally occurring vector or genomic DNA; (c) a separate molecule such as cDNA, a genomic fragment, a fragment produced by polymerase chain reaction, or a restriction fragment; and (d) a recombinant nucleotide sequence that is part of a hybrid gene, i.e., a gene encoding a fusion protein.

By "label" is meant any detectable tag that can be attached directly (e.g. a fluorescent molecule integrated into a polypeptide or nucleic acid) or indirectly (e.g., by way of binging to a primary antibody a secondary antibody with an integrated fluorscent molecule) to the molecule of interest. A "label" is any tag that can be visualized with imaging methods. The detectable tag can be a radio-opaque substance, radiolabel a fluorescent label, or a magnetic label. The detectable tag can be selected from the group consisting of gamma-emitters, beta-emitters, and alpha emitters, gamma-emitters, positron-emitters, X-ray-emitters and fluorescence-emitters suitable for localization. Suitablle fluorescent compounds include fluorescein sodium, fluorescein isothiocyanate, phycoerythrin, and TEXAS RED® sulfonyl chiloride (Molecular Probes, Eugene, OR). See, de Belder & Wik (Preparation and properties of fluorescein-labelled hyaluronate. Carbohydr. Res.44(2):251-57 (1975). Those skilled in the art will know, or will be able to ascertain with no more than routine experimentation, other fluorescent compounds that are suitable for labeling the molecule.

Polypeptides

The invention provides members of a cluster of FcR and FcR gene relatives encoded by genes in the human chromosome 1 q21-23 region, or analogous region in non-human subjects, including for example, chromosome 3 in mouse. A consensus amino acid motif, based on the FcγRI, FcγRII, FcγRIII and pIgR extracellular regions, was used in a GenBank protein database query to identify member of the gene subfamily. Genomic clones were identified that were found to contain FcR relatives and are termed the Fc receptor homolog (FcRH) subfamily: specifically, FcRH1, FcRH2, FcRH3, and FcRH6. Also, found were mouse Fc receptor homologs designated moFcR1, 2, and 3.

By "homologous" is meant about 25% percent homology or greater. Homology is also characterized by proximity in the location of the genes and by similarities as identified in a composite analysis. As used herein, "percent homology" of two amino acid sequences or of two nucleic acid sequences is determined using the algorithm of Karlin and Altschul (Proc. Natl. Acad. Sci. USA 87:2264-2268 (1990)). Such an algorithm is incorporated into the NBLAST and XBLAST programs of Altschul et al. (J. Mol. Biol. 215:403-410 (1990)). BLAST nucleotide searches are performed with the NBLAST program, score 100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped Blast is utilized as described in Altschul et al. (Nucl. Acids Res. 25: 3389-3402 (1997)). When utilizing BLAST and Gapped BLAST programs, the default parameters of the respective programs (e.g., XBLAST and NBLAST) are used. See http://ww.ncbi.nlm.nih.gov.

By "FcRH" is meant a Type I transmembrane receptor, or an alternatively spliced form thereof, including, for example, a secreted form or a GPI-anchored form, with homology to the classical Fc receptor family. In a preferred embodiment, the FcRH shows homology with the extracellular regions of FcγRI, FcγRII, FcγRIII, or pIgR. More specifically, the FcRH shows homology with an amino acid sequence corresponding with the amino terminal sequences of the second Ig domains of the FcγRs and the third Ig domain of pIgR or FcγRH1. The FcRH can comprise an extracellular region, a transmembrane region, and a cytoplasmic region. The extracellular region preferably comprises one or more Ig domains, and more preferably less than 9, and even more preferably less than 7 or less than 8 Ig domains. Preferably, the cytoplasmic region comprises more than 107 (including more than 108, 109, 110, 111, 112, 113, 114, 115, 120, 121, 122, 123, 124, 125, 126, 127, 128, 129, 130, 131, 132, 133, 134, 135, 136, 137, 138, 139, 140, 141, 142, 143, 144, or 145 amino acids). Alternatively, the cytoplasmic region comprises less than 104 amino acids (including less than 103, 102, 101, 100, 99, 98, 97, 96, 95, 94, 93, 92, 91, 90, 89, 88, 87, 86, 85, 84, 83, 82, 81, 80). The cytoplasmic region preferably comprises one or more immunoreceptor tyrosine-based inhibitory or activation motifs ("ITIMs" or "ITAMs).

The invention provides isolated FcRHs (e.g., huFcRH 1, 2, 3, and 6, and moFcRH1-3, as described in detail below), as well as fragments and isoforms thereof. The isolated amino acid sequences provided herein optionally are combined with a human signal sequence (e.g., MLPRLLLLI-CAPLCEP (SEQ ID NO:29), MLLWSLLVIFDAVTEQADS (SEQ ID NO:30), MLLWLLLILTPGREQS (SEQ ID NO:31), MLLWTAVLLFVPCVG (SEQ ID NO:32)) or a mouse signal sequence (e.g., MPLCLLLLVFAPVGVQS (SEQ ID NO:69), MLPWLLLLICALPCEPA (SEQ ID NO:72), MSGSFSPCVVFTQMWLTLLVVTPVN (SEQ ID NO:79)).

In one embodiment, the invention provides huFcRH1 and its fragments and isoforms. Thus, in one embodiment of the isolated FcRH, the extracellular region comprises less than four Ig domains. Preferably, the cytoplasmic region comprises less than 104 amino acids and, even more preferably, comprises less than 104 and more than 86 amino acids. In one embodiment, the transmembrane region comprises an acidic amino acid (e.g., glutamate or aspartate). The isolated FcRH of the invention comprises a cytoplasmic region having the amino acid sequence of SEQ ID NO:1, in the presence or absence of conservative amino acid substitutions. Further provided is the isolated FcRH, wherein the extracellular region comprises the amino acid sequence of SEQ ID NO:21, in the presence or absence of conservative amino acid substitutions, and in the presence and absence of a signal sequence. More specifically, the isolated FcRH comprises the amino acid sequence of SEQ ID NO:2, in the presence or absence of conservative amino acid substitutions, and in the presence or absence of a signal sequence. In one embodiment the signal sequence is MLPRLLLLI-CAPLCEP (SEQ ID NO:29). In a preferred embodiment, the FcRH of the invention is expressed by myeloid cells (e.g., granulocytes and monocytes). Additional characteristics of the full length FcRH1 include a predicted molecular weight of about 46-47 kDaltons; about 425-435 (e.g., 429) amino acids in length with about 35 strongly basic(+) amino acids (K,R), about 45 strongly acidic(−) amino acids (D,E), about 144 hydrophobic amino acids (A,I,L,F,W,V), and about 127 polar amino acids (N,C,Q,S,T,Y); a predicted isoelectric point of about 5-5.5 (e.g., 5.310); and charge of about −9 at PH 7.0.

In another embodiment, the invention provides an isolated FcRH corresponding to huFcRH2, its fragments, or isoforms. Thus, the invention provides a FcRH wherein the cytoplasmic region comprises less than 99 amino acids (e.g., 80, 81, 82, 83, 84, 85, 86, 87, 88, 89, 90, 91, 92, 93, 94, 95, 96, 97, 98) and wherein the receptor further comprises an extracellular domain with up to four Ig domains and up to five N-linked glycosylation sites. More specifically, the isolated FcRH has a cytoplasmic region that comprises the amino acid sequence of SEQ ID NO:3, in the presence or absence of conservative amino acid substitutions, or an extracellular region comprising SEQ ID NO:22, in the presence or absence of conservative amino acid substitutions, and in the presence or absence of a signal sequence. Even more specifically, the isolated FcRH comprises the amino acid sequence of SEQ ID NO:4, in the presence or absence of conservative amino acid substitutions, and in the presence or absence of a signal sequence. In one embodiment, the signal sequence WSLLVIFDAVTEQADS (SEQ ID NO:30). Additional characteristics of the fall length FcRH1 include a predicted molecular weight of about 50-60 kDaltons; about 495-515 (e.g., 508) amino acids in length with about 44 strongly basic(+) amino acids (K,R), about 49 strongly acidic(−) amino acids (D,E), about 175 hydrophobic amino acids (A,I,L,F,W,V), and about 161 polar amino acids (N,C,Q,S,T,Y); a predicted isoelectric point of about 6-6.5 (e.g., 6.188); and charge of about −4 at PH 7.0.

In another embodiment, the invention provides huFcRH3, its fragments, and isoforms. More specifically, the invention provides an isolated FcRH having a cytoplasmic region that comprises more than 107 amino acids (e.g., 108, 109, 110, 111, 112, 113, 114, 115, 116, 117, 118, 119, 120, 212, 122, 123, 124, 125, 126, 127, 128, 129, 130, 131, 132, 133, 134, 135, 136, 137, 138, 139, 140, 141, 142, 143, 144, 145, 146, 247, 148, 149, 150 amino acids). Optionally, the isolated FcRH has a cytoplasmic region comprising one ITAM and one ITIM. More specifically, the cytoplasmic region comprises the amino acid sequence of SEQ ID NO:5 or SEQ ID NO:23, in the presence or absence of conservative amino acid substitutions. In one embodiment, the extracellular domain of the FcRH comprises the amino acid sequence of SEQ ID NO:24, in the presence or absence of conservative amino acid substitutions, and in the presence or absence of a signal sequence. Also provided is an isolated FcRH comprising the amino acid sequence of SEQ ID NO:6 or SEQ ID NO:25, in the presence or absence of one or more amino acid substitutions, and in the presence or absence of a signal sequence. In one embodiment the signal sequence comprises MLLWLLLLILTPGREQS (SEQ ID NO:31). Additional characteristics of the full length FcRH1 include a predicted molecular weight of about 80-90 kDaltons; about 725-740 (e.g., 734) amino acids in length with about 68 strongly basic(+) amino acids (K,R), about 75 strongly acidic(−) amino acids (D,E), about 232 hydrophobic amino acids (A,I,L,F,W,V), and about 224 polar amino acids (N,C, Q,S,T,Y); a predicted isoelectric point of about 6.5-7.0 (e.g., 6.852); and charge of about −2 at PH 7.0.

The invention further provides an isolated huFcRH6, its fragments, and isoforms. More specifically, the FcRH comprises a cytoplasmic region having the amino acid sequence of SEQ ID NO:26, in the presence or absence or one or more conservative amino acid substitutions. The extracellular domain comprises the amino acid sequence of SEQ ID NO:27, in the presence or absence of conservative amino acid substitutions, and in the presence or absence of a signal sequence. Also, provided by the invention is a FcRH having the amino acid substitutions of SEQ ID NO:28, in the presence or absence of conservative amino acid substitutions, and in the presence or absence of a signal sequence. In one embodiment the signal sequence is MLLWTAVLL-FVPCVG (SEQ ID NO:32).

The invention further provides a polypeptide comprising the amino acid sequence of SEQ ID NO:1, 21, 2, 3, 22, 4, 5, 23, 24, 6, 25, 26, 27, or 28, in the presence or absence of conservative amino acid substitutions. The invention also provides a polypeptide having at least 80, 85, 90, or 95% homology with SEQ ID NOs: 1, 21, 2, 3, 22, 4, 5, 23, 24, 6, 25, 26, 27, or 28.

The invention further provides an isolated moFcRH1 isoform, its fragments, and isoforms. The moFcRH1 is an isoform of SEQ ID NO:68. More specifically, the FcRH comprises four Ig domains, optionally having the sequence of SEQ ID NO: 70, in the presence or absence or one or more conservative amino acid substitutions, and in the presence or absence of a signal sequence (e.g., the sequence of SEQ ID NO:71).

The invention further provides an isolated moFcRH2, its fragments, and isoforms. The provided isoforms include one isoform with a transmembrane region and one isoform lacking the transmembrane region. More specifically, the FcRH comprises a cytoplasmic region having the amino acid sequence of SEQ ID NO:76, in the presence or absence or one or more conservative amino acid substitutions. The extracellular domain comprises the amino acid sequence of SEQ ID NO:74, in the presence or absence of conservative amino acid substitutions, and in the presence or absence of a signal sequence. Also, provided by the invention is a FcRH having the amino acid sequence of SEQ ID NO:73, which comprises a transmembrane region, or SEQ ID NO:77, which lacks the transmembrane region. In each case, the FcRH sequence can include the presence or absence of conservative amino acid substitutions, and the presence or absence of a signal sequence. In one embodiment the signal sequence is the sequence of SEQ ID NO:72.

The invention also provided a moFcRH3, its fragments and isoforms. The cytoplasmic region can comprise the amino acid sequence of SEQ ID NO:81, in the presence or absence of conservative amino acid substitutions. Optionally, the extracellular domain comprises the amino acid sequence of SEQ ID NO:80, in the presence or absence of conservative amino acid substitutions or in the presence or absence of a signal sequence (e.g., the sequence of SEQ ID NO:79). The full length sequence optionally has the aminoacid sequence of SEQ ID NO:78, in the presence or absence of conservative amino acid substitutions or in the presence or absence of a signal sequence (e.g., the sequence of SEQ ID NO:79).

Fragments, variants, or isoforms of the FcRHs of the invention are provided. It is understood that these terms include functional variants. Fragments can include the cytoplasmic region, the extracellular region, the transmembrane region or any portion of at least 10 amino acids or any combination of the regions or portions. The variants are produced by making amino acid substitutions, deletions, and insertions, as well as post-translational modifications. Variations in post-translational modifications can include variations in the type or amount of carbohydrate moieties of the protein core or any fragment or derivative thereof. Variations in amino acid sequence may arise naturally as allelic variations (e.g., due to genetic polymorphism) or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations.

Amino acid sequence modifications fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about 2 to 6 residues are deleted at any one site within the protein molecule. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues but may include multiple substitutions at different positions; insertions usually will be on the order of about from 1 to 10 amino acid residues but can be more; and deletions will range about from 1 to 30 residues, but can be more. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with Table 1 and are referred to as conservative substitutions.

TABLE 1

Amino Acid Substitutions

| Original Residue | Exemplary Substitutions |
|---|---|
| Ala | Ser |
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions that in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl. Modifications in the FcRH can also include modifications in glycosylation.

In all mutational events, it is understood that the controlling aspect of the mutation is the function that the subsequent protein possesses. The preferred mutations are those that do not detectably change the desired function or that increase the desired function.

Nucleic Acids

Also provided is an isolated nucleic acid that encodes the FcRH of the invention. The nucleic acid can be single or double stranded and can be RNA or DNA. More specifically, the invention provides an isolated nucleic acid, comprising a nucleotide sequence that encodes SEQ ID NO:1, SEQ ID NO:21, SEQ ID NO:2. SEQ ID NO: 3, SEQ ID NO:22, SEQ ID NO:4, SEQ ID NO:5, SEQ ID NO:23, SEQ ID NO:24, SEQ ID NO:25, SEQ ID NO:26, SEQ ID NO:27, SEQ ID NO:28, or SEQ ID NO:6, SEQ ID NO:70, SEQ ID NO:73, SEQ ID NO:74, SEQ ID NO:76, SEQ ID NO:77, SEQ ID NO:78, SEQ ID NO:80, SEQ ID NO:81, optionally with conservative amino acid substitutions. Optionally the nucleic acid further encodes a signal sequence (e.g., the signal sequences of SEQ ID NO:29, 30, 31, 32, 71, 75, 79). The isolated nucleic acid optionally encodes the sequences with 80, 85, 90, or 95% identity. More specifically, the invention provides an isolated nucleic acid, comprising a nucleotide sequence of SEQ ID NO:7, SEQ ID NO:13, SEQ ID NO:8, SEQ ID NO:34, SEQ ID NO:9, SEQ ID NO:14, SEQ ID NO:10, SEQ ID NO:36, SEQ ID NO:11, SEQ ID NO:15, SEQ ID NO:16, SEQ ID NO:12, SEQ ID NO:38, SEQ ID NO:17, SEQ ID NO:18, SEQ ID NO:19, SEQ ID NO:20; SEQ ID NO:40, SEQ ID NO:84, SEQ ID NO:85, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, or SEQ ID NO:102. Optionally, the isolated nucleic acid can further included bases that encode a signal sequence and thus the nucleotide sequence encoding the extracellular region or full-length huFcRH1, 2, 3, or 6 can optionally further comprise the nucleotide sequence of SEQ ID NO:33, SEQ ID NO:35, SEQ ID NO:37, SEQ ID NO:39. Optionally, the isolated nucleic acids for moFcRHs include nucleic acid sequences that encode signal sequences as well, including for example, those portions of nucleic acid sequences SEQ ID NO:101, SEQ ID NO:97, SEQ ID NO:94, SEQ ID NO:91, SEQ ID NO:88, SEQ ID NO:84.

Preferably the nucleic acid that encodes the full length FcRH1 includes about 290 bases. The nucleic acid that encodes the full length FcRH2 includes about 1527 bases, and the nucleic acid that encodes the full length FcRH3 includes about 2205 bases.

The invention also provides an isolated nucleic acid comprising a sequence that hybridizes under stringent conditions to a hybridization probe, wherein the hybridization probe comprises the nucleotide sequence of SEQ ID NO:7, SEQ ID NO:13, SEQ ID NO:8, SEQ ID NO:34, SEQ ID NO:9, SEQ ID NO:14, SEQ ED NO:10, SEQ ID NO:36, SEQ ID NO:11, SEQ ID NO:15, SEQ ID NO:16, SEQ ID NO:12, SEQ ID NO:38, SEQ ID NO:17, SEQ ID NO:18, SEQ ID NO:19, and SEQ ID NO:20; SEQ ID NO:40, SEQ ID NO:84, SEQ ID NO:85, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, or SEQ ID NO:102, or the complement of either sequence.

Further provided is a single stranded nucleic acid that hybridizes under stringent conditions to a nucleic acid having the sequence of SEQ ID NO:7, SEQ ID NO:13, SEQ ID NO:8, SEQ ID NO:34, SEQ ID NO:9, SEQ ID NO:14, SEQ ID NO:10, SEQ ID NO:36, SEQ ED NO:11, SEQ ID NO:15, SEQ ID NO:16, SEQ ID NO:12, SEQ ID NO:38, SEQ ID NO:17, SEQ ID NO:18, SEQ ID NO:19, and SEQ ID NO:20; SEQ ID NO:40, SEQ ID NO:84, SEQ ID NO:85, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, or SEQ ID NO:102.

By "hybridizing under stringent conditions" or "hybridizing under highly stringent conditions" is meant that the hybridizing portion of the hybridizing nucleic acid, typically comprising at least 15 (e.g., 20, 25, 30, or 50 nucleotides), hybridizes to all or a portion of the provided nucleotide sequence under stringent conditions. The term "hybridization" typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art.

For example, the salt concentrations, pH, and temperature of the reaction all affect whether two nucleic acid molecules will hybridize. Generally, the hybridizing portion of the hybridizing nucleic acid is at least 80%, for example, at least 90%, 95%, or 98%, identical to the sequence of or a portion of a nucleic acid encoding an FcRH of the invention, or its complement. Hybridizing nucleic acids of the invention can be used, for example, as a cloning probe, a primer (e.g., for PCR), a diagnostic probe, or an antisense probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Assuming that a 1% mismatch results in a 1° C. decrease in the Tm, the temperature of the final wash in the hybridization reaction is reduced accordingly (for example, if sequence having >95% identity with the probe are sought, the final wash temperature is decreased by 5° C.). In practice, the change in Tm can be between 0.5° C. and 1.5° C. per 1% mismatch. Stringent conditions involve hybridizing at 68° C. in 5×SSC/5× Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, in Sambrook et al., 1989, Molecular Cloning, A Laboratory Manual, Cold Spring Harbor Press, NY; and Ausubel et al. (eds.), 1995, Current Protocols in Molecular Biology, (John Wiley & Sons, NY) at Unit 2.10.

The nucleic acids of the present invention are optionally labeled, directly or indirectly. Such labeled nucleic acids are useful in various diagnostic techniques including for example, in situ hybridization, FISH, in situ PCR, and PRINS. Both methods involve the preparation of short sequences of single-stranded nucleic acid probes that are complementary to the nucleic acid sequences that encode an FcRH. See, e.g., M Andreeff and D Pinkel (1999), An Introduction to Flourescent In-Situ Hybridization: Principles and Clinical Applications, John Wiley & Sons, Ltd; Roche Applied Sciences (2000), Nonradioactive In Situ Hybridization Application Manual; Roche Applied Sciences (1999), PCR Manual, 2d edition, which are incorporated in their entirety for methods of using nucleic acids.

Vectors, Cells, and Methods of Using

Also provided is an expression vector comprising a nucleic acid of the invention, wherein the nucleic acid is operably linked to an expression control sequence. A wide variety of expression system/regulatory sequence combinations may be employed in expressing the disclosed. Such useful regulatory sequences include, for example, the early or late promoters of SV40, CMV, vaccinia, polyoma or adenovirus, the lac system, the trp system, the TAC system, the TRC system, the LTR system, the major operator and promoter regions of phage lambda, the control regions of fd coat protein, the promoter for 3-phosphoglycerate kinase or other glycolytic enzymes, the promoters of acid phosphatase (for example, Pho5), the AOX 1 promoter of methylotrophic yeast, the promoters of the yeast a-mating factors, and other sequences known to control the expression of genes of prokaryotic or eukaryotic cells or their viruses, and various combinations thereof.

Such an expression vector can be designed to be expressed by eukaryotic cells or prokaryotic cells. The vectors of the present invention thus provide DNA molecules which are capable of integration into a prokaryotic or eukaryotic chromosome and expression. The inserted genes in viral and retroviral vectors usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. It has been shown that all specific regulatory elements can be cloned and used to construct expression vectors that are selectively expressed in specific cell types. For example, the glial fibrillary acetic protein (GFAP) promoter has been used to selectively express genes in cells of glial origin. Expression vectors used in eukaryotic host cells (e.g., yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

The invention further provides transfer vectors, which include any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). As used herein, plasmid or viral vectors are agents that transport the disclosed nucleic acids into the cell without degradation and include a promoter yielding expression of the gene in the cells into which it is delivered. In some embodiments the FcRHs are derived from either a virus or a retrovirus. Viral vectors include, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families that share the properties of these viruses that make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines that have been engineered to express the gene products of the early genes in trans.

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference. A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules that are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line that has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang, Generation and identification of recombinant adenovirus by liposome-mediated transfection and PCR analysis, BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorproated by reference for material related to the AAV vector.

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes. Other useful systems include, for example, replicating and host-restricted non-replicating vaccinia virus vectors.

The invention also provides an isolated cell comprising a vector of the invention. The isolated cell can be either a eukaryotic or prokaryotic cell, such as strains of *E. coli, Pseudomonas, Bacillus, Streptomyces*; fungi such as yeasts (*Saccharomyces*, and methylotrophic yeast such as *Pichia, Candida, Hansenula,* and *Torulopsis*); and animal cells, such as CHO, R1.1, B-W and LM cells, African Green Monkey kidney cells (for example, COS 1, COS 7, BSC1, BSC40, and BMT10), insect cells (for example, Sf9), and human cells and plant cells in tissue culture.

Also provided is a method of making a FcRH, or a fragment or variant thereof comprising culturing a cell comprising a vector of the invention under conditions permitting expression of the FcRH. The method comprises culturing a cell comprising an exogeneous nucleic acid that encodes the FcRH, fragment, or variant, wherein the exogeneous nucleic acid is operably linked to an expression control sequence, and wherein the culture conditions permit expression of the FcRH, fragment, or variant under the control of the expression control sequence; harvesting the medium from the cultured cells, and isolating the FcRH, fragment, or variant from the cell or culture medium. Optionally the exogenous nucleic acid is the nucleotide sequence of SEQ ID NO:7, SEQ ID NO:13, SEQ ID NO:8, SEQ ID NO:34, SEQ ID NO:9, SEQ ID NO:14, SEQ ID NO:10, SEQ D NO:36, SEQ ID NO:11, SEQ ID NO:15, SEQ ID NO:16, SEQ ID NO:12, SEQ ID NO:38, SEQ ID NO:17, SEQ ID NO:18, SEQ ID NO:19, and SEQ ID NO:20; SEQ ID NO:40, SEQ ID NO:84, SEQ ID NO:85, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, or SEQ ID NO:102 or a combination thereof. Optionally, the exogenous nucleic acid further comprises a nucleotide sequence that encodes a signal sequence. In the recombinant methods, the cell can be any known host cell, including for example, a prokaryotic or eukaryotic cell. The nucleic acids that are delivered to cells, generally in a plasmid or other vector, typically contain expression controlling systems. For example, the inserted genes in viral and retroviral systems usually contain promoters, and/or enhancers to help control the expression of the desired gene product.

Those skilled in the art of molecular biology will understand that a wide variety of expression systems may be used to produce recombinant FcRH polypeptides (as well as fragments, fusion proteins, and amino acid sequence variants with therapeutic activity) for use in the methods of the invention. Thus, FcRH may be produced using prokaryotic host cells (e.g., *Escherichia coli*) or eukaryotic host cells (e.g., *Saccharomyces cerevisiae*, insect cells such as Sf9 cells, or mammalian cells such as CHO cells, COS-1, NIH 3T3, or HeLa cells). These cells are commercially available from, for example, the American Type Culture Collection, Rockville, Md. (see also F. Ausubel et al., Current Protocols in Molecular Biology, John Wiley & Sons, New York, N.Y., 1998). The method of transformation and the choice of expression vector will depend on the host system selected. Transformation and transfection methods are described, e.g., in Ausubel et al., supra, and expression vectors may be chosen from the numerous examples known in the art.

A nucleic acid sequence encoding an FcRH is introduced into a plasmid or other vector, which is then used to transform living cells. Constructs in which a cDNA containing the entire FcRH coding sequence, a fragment of the FcRH coding sequence, amino acid variations of the FcRH coding sequence, or fusion proteins of the aforementioned, inserted in the correct orientation into an expression plasmid, may be used for protein expression. In some cases, for example, it may be desirable to express the FcRH coding sequence under the control of an inducible or tissue-specific promoter.

Eukaryotic expression systems permit appropriate post-translational modifications to expressed proteins. Thus, eukaryotic, and more preferably mammalian expression systems, allow glycosylations patterns comparable to naturally expressed FcRH. Transient transfection of a eukaryotic expression plasmid allows the transient production of FcRH by a transfected host cell. FcRH may also be produced by a stably-transfected mammalian cell line. A number of vectors suitable for stable transfection of mammalian cells are available to the public (e.g., see Pouwels et al., Cloning Vectors: A Laboratory Manual, 1985, Supp. 1987), as are methods for constructing such cell lines (see e.g., F. Ausubel et al., Current Protocols in Molecular Biology, John Wiley & Sons, New York, N.Y., 1998). Another preferred eukaryotic expression system is the baculovirus system using, for example, the vector pBacPAK9, which is available from Clontech (Palo Alto, Calif.). If desired, this system may be used in conjunction with other protein expression techniques, for example, the myc tag approach described by Evan et al. (Mol. Cell Biol. 5:3610-3616, 1985) or analogous tagging approaches, e.g., using a hemagluttinin (HA) tag.

Once the recombinant protein is expressed, it can be isolated from the expressing cells by cell lysis followed by protein purification techniques such as affinity chromatography. In this example, an antibody that specifically binds to FcRH, which may be produced by methods that are well-known in the art, can be attached to a column and used to isolate FcRH. Once isolated, the recombinant protein can, if desired, be purified further, e.g., by high performance liquid chromatography (HPLC; e.g., see Fisher, Laboratory Techniques In Biochemistry And Molecular Biology, Work and Burdon, Eds., Elsevier, 1980).

Antibodies

The invention also provides a purified antibody or immunologic fragment thereof, wherein the antibody or fragment thereof selectively binds to an FcRH. As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest" National Institutes of Health, Bethesda, Md. (1987)). The constant domains are not involved directly in binding an antibody to an antigen, but exhibit various effector functions, such as participation of the antibody in antibody-dependent cellular toxicity.

The term "antibody or fragments thereof" can also encompass chimeric antibodies and hybrid antibodies, with dual or multiple antigen or epitope specificities, and fragments, such as F(ab')$_2$, Fab', Fab and the like, including hybrid fragments. Thus, fragments of the antibodies that retain the ability to bind their specific antigens are provided. For example, fragments of antibodies which maintain FcRH binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

In one embodiment, the antibody is a monoclonal antibody. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., Proc. Natl. Acad. Sci. USA, 81:6851-6855 (1984)).

Monoclonal antibodies of the invention may be prepared using hybridoma methods, such as those described by Kohler and Milstein, Nature, 256:495 (1975) or Harlow and Lane, Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises an FcRH. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of FcRH, preferably the N- or C-terminal region, is injected into the host animal according to methods known in the art.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63).

The culture medium in which the hybridoma cells are cultured can then be assayed for the presence of monoclonal antibodies directed against an FcRH. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody comprising one antigen-combining site having specificity for FcRH and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 10 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific epitope or fragment of the antibody is also provided. A specific immunogenic epitope of the antibody can be isolated from the whole antibody by chemical or mechanical disruption of the molecule. The purified fragments thus obtained can be tested to determine their immunogenicity and specificity by the methods taught herein. Immunoreactive epitopes of the antibody can also be synthesized directly. An immunoreactive fragment is defined as an amino acid sequence of at least about two to five consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY). Alternatively, the peptide or polypeptide can by independently synthesized in vivo as described above. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-α-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments can be chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with fall biological activity (deLisle Milton R C et al., Techniques in Protein Chemistry IV. Academic Press, New York, pp. 257-267 (1992)).

The invention also provides fragments of antibodies that have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with FcRH. For example, amino acids found to not contribute to either the activity or the binding specificity or affinity of the antibody can be deleted without a loss in the respective activity.

For example, amino or carboxy-terminal amino acids can be sequentially removed from either the native or the modified non-immunoglobulin molecule or the immunoglobulin molecule and the respective activity assayed in one of many available assays. In another example, a fragment of an antibody can comprise a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry of cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences, can also include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

As used herein, the phrase "specific binding" or "selective binding" refers to a binding reaction which is determinative of the presence of the FcRH in a heterogeneous population of proteins and other biologics. Thus, under designated conditions, the antibodies or fragments thereof of the present invention bind to a particular FcRH (e.g., human FcRH 1 or any variant thereof), fragment, or variant thereof and do not bind in a significant amount to other proteins (e.g., human FcRH 2, 3, 4, 5, or 6), present in the subject. The absence of binding in the present invention is concisderd to be binding that is less than 1.5 times background (i.e., the level of non-specific binding or slightly above non-specific binding levels), Selective binding to an antibody under such conditions may require an antibody that is selected for its specificity for a particular protein, variant, or fragment. In one embodiment the purified antibody selectively binds to the FcRH comprising a cytoplasmic region with more than 107 or less than 104 amino acids, a transmembrane region, and an extracellular region. More specifically, the antibody in alternative embodiments selectively binds FcRH1 but not FcRH2-6; selectively binds FcRH2 but not 1 or 3-6; selectively binds FcRH3 but not FcRH1-2 or 4-6; selectively binds FcRH6 but not 1-5. Thus, as one embodiment, the antibody selectively binds a polypeptide comprising the amino acid sequence of SEQ ID NO:1, 21, or 2, or a subset thereof, but not to polypeptides comprising the amino acid of SEQ ID NO:3, 22, 4, 5, 23, 24, 6, 25, 26, 27, 28, or a subset thereof. In another embodiment the purified antibody binds to the FcRH comprising the amino acid sequence of SEQ ID NO:3, 22, or 4, but not to the FcRH comprising the amino acid of SEQ ID NO:1, 21, 2, 5, 23, 24, 6, 25, 26, 27, or 28. In yet another embodiment, the purified antibody that binds to the FcRH comprising the amino acid sequence of SEQ ID NO:5, 23, 24, or 6, but not to the FcRH comprising the amino acid of SEQ ID NO:1, 21, 2, 3, 22, 4, 26, 27, 28. Similarly, the antibodies of the present invention may bind only moFcRH1, but not moFcRH 2 or moFcRH3; may bind only FcRH2 and not FcRH1 or FcRH3, and may bind only FcRH3 and not FcRH1 or FcRH2.

In certain embodiments, the antibody binds the extracellular region of one or more FcRHs and in other embodiments the antibody binds the cytoplasmic region of one or more FcRHs. In other embodiments the antibody may selectively bind one isoform of a FcRH. For example, the antibody may bind a polypeptide having the amino acid sequence of SEQ ID NO:23 but not the SEQ ID NO:24 or vice versa. Furthermore, the antibody can bind to moFcRH1 having the amino acid sequence of SEQ ID NO:70, but not to a moFcRH1 having amino acid sequence of SEQ ID NO:68. The antibody may selectively bind a moFcRH2 with a transmembrane region (e.g., having amino acid sequence of SEQ ID NO:73), but not bind to a moFcRH2 lacking a transmembrane region (e.g., having the amino acid sequence of 77). Optionally the antibody of the invention can selectively bind moFcRH but not human, or vice versa.

A variety of immunoassay formats may be used to select antibodies that selectively bind with a particular protein, variant, or fragment. For example, solid-phase ELISA immunoassays are routinely used to select antibodies selectively immunoreactive with a protein, variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

The Invention also provides an antibody reagent kit comprising the antibody or fragment thereof of the invention and reagents for detecting binding of the antibody or fragment thereof to a ligand. The kit can further comprise containers containing the antibody or fragment thereof of the invention and containers containing the reagents. Preferably the ligand is a FcRH, variant, or fragment thereof, Particularly, the kit can detect the presence of one or more FcRHs specifically reactive with the antibody or an immunoreactive fragment thereof. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above, The diagnostic kit can alternatively, be in immunoblot kit generally comprising the components and reagents described herein. Alternatively, the kit could be a radioimmunoassay kit, a Western blot assay kit, an immunohistological assay kit, an immunocytochemical assay kit, a dot blot assay kit, a fluorescence polarization assay kit, a scintillation proximity assay kit, a homogeneous time resolved fluorescence assay kit, or a BIACORE® analysis kit (Pharmacia, Sweden).

As used throughout methods of detectina an PeRil or antigen/antibody complexes, including complexes comprising an FCRH and optionally the antibody of the present invention, can comprise an ELISA (competition or sandwich), a radioimmunoassay, a Western blot assay, an immunohistological assay, an immunocytochemical assay, a dot blot assay, a fluorescence polarization assay (Jolley (1981); Jiskoot et al (1991); Seethala et al. (1998); Bicainuinpaka et al. (1998)), a scintillation proximity assay (Amersham Life Science (1995) Proximity News, Issue 17; Amersham Life Science (1995) Proximity News. Issue 18; Park et al. (1999)), a homogeneous time-resolved fluorescence assay (Park et al. (1999); Stenroos et al. (1988); Morrison, 1988)), or a BIACORE® (Pharmacia, Sweden) analysis (Fägerstam et al. (1992) Chromatography 597:397-410). Preferably, the antigen/antibody complex is detectably tagged either directly or indirectly. Any desired tag can be utilized, such as a fluorescent tag, a radiolabel, a magnetic tag, or an enzymatic reaction product.

Optionally, the antibody or fragment is a humanized antibody or a fully human antibody. For example, the antibodies can also be generated in other species and "humanized" for administration to humans. Alternatively, fully human antibodies can also be made by immunizing a mice or other species capable of making a fully human antibody (e.g., mice genetically modified to produce human antibodies), screening clones that bind FcRH. See, e.g., Lonberg and Huszar (1995) Human antibodies from transgenic mice, Int. Rev. Immunol. 13:65-93, which is incorporated herein by reference in its entirety for methods of producing fully human antibodies. As used herein, the term "humanized" and "fully human" in relation to antibodies, relate to any antibody which is expected to elicit a therapeutically tolerable weak immunogenic response in a human subject.

Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et at, Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679 published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(l):86-95 (1991)).

In one embodiment, the antibody or fragment thereof is a single chain antibody. In another embodiment, the antibody or fragment is labeled. Optionally the antibody or fragment is conjugated or fused with a toxin or fragment thereof. Examples of the toxin or toxin moiety include diphtheria, ricin, and modifications thereof.

Diagnosis and Treatment

The invention provides uses of the reagents described herein in in vitro and iii vivo methods of diagnosing and treating a malignancy of hematopoietic cell lineage or an autoimmune disease in a subject. The reagents of the present invention are also useful in screening for disease manifestations. Such screening may be useful even before the onset of other clinical symptoms and could be used to screening subjects at risk for disease, so that prophylactic treatment can be started before the manifestation of other signs or symptoms.

By "malignancy" is meant a tumor or neoplasm whose cells possess one or more nuclear or cytoplasmic abnormalities, including, for example, high nuclear to cytoplasmic ratio, prominent nucleolar/nucleoli variations, variations in nuclear size, abnormal mitotic figures, or multinucleation. "Malignancies of hematopoietic cell lineage" include, but are not limited to, myelomas, leukemias, lymphomas (Hodgkin's and non-Hodgkin's forms), T-cell malignancies, B-cell malignancies, and lymphosarcomas or other malignancies described in the REAL classification system or the World Health Organization Classification of Hematologic Malignancies. It should be noted that the absence or presence of specific FcRHs can be diagnostic for a particular malignancy of hematopoietic cell linage or can be diagnostic for a particular form of a malignancy (e.g., a specific form of leukemia).

By "inflammatory and autoimmune diseases" illustratively including systemic lupus erythematosus, Hashimoto's disease, rheumatoid arthritis, graft-versus-host disease, Sjögren's syndrome, pernicious anemia, Addison disease, scleroderma, Goodpasture's syndrome, Crohn's disease, autoimmune hemolytic anemia, sterility, myasthenia gravis, multiple sclerosis, Basedow's disease, thrombopenia purpura, insulin-dependent diabetes mellitus, allergy; asthma, atopic disease; arteriosclerosis; myocarditis; cardiomyopathy; glomerular nephritis; hypoplastic anemia; rejection after organ transplantation and numerous malignancies of lung, prostate, liver, ovary, colon, cervix, lymphatic and breast tissues.

Specifically, the diagnostic methods comprise the steps of contacting a biological sample of the subject with an antibody or nucleic acid of the invention under conditions that allow the antibody to bind to cells of hematopoietic cell lineage or allow the nucleic acid to hybridize, preferably under stringent conditions, with nucleic acids of the biological sample; and detecting the amount or pattern of binding. Changes in the amount or pattern of binding as compared to binding in a control sample indicate a malignancy or an inflammatory or autoimmune disease.

In various embodiments, the antibody used in the diagnostic method can selectively bind with an FcRH having the amino acid sequence of SEQ ID NO:1, 21, 2, 3, 22, 4, 5, 24, or 6.

The detecting step of the diagnostic method can be selected from methods routine in the art. For example, the detection step can be performed in vivo using a noninvasive medical technique such as radiography, fluoroscopy, sonography, imaging techniques such as magnetic resonance imaging, and the like. In vitro detection methods can be used to detect bound antibody or fragment thereof in an ELISA, RIA, immunohistochemically, FACS, IHC, FISH, or similar assays.

As used throughout, "biological sample" refers to a sample from any organism. The sample can be, but is not limited to, peripheral blood, plasma, urine, saliva, gastric secretion, feces, bone marrow specimens, primary tumors, embedded tissue sections, frozen tissue sections, cell preparations, cytological preparations, exfoliate samples (e.g., sputum), fine needle aspirations, amnion cells, fresh tissue, dry tissue, and cultured cells or tissue. It is further contemplated that the biological sample of this invention can also be whole cells or cell organelles (e.g., nuclei). The sample can be unfixed or fixed according to standard protocols widely available in the art and can also be embedded in a suitable medium for preparation of the sample. For example, the sample can be embedded in paraffin or other suitable medium (e.g., epoxy or acrylamide) to facilitate preparation of the biological specimen for the detection methods of this invention.

The invention also provides a method of treating a malignancy of hematopoietic cell lineage or an inflammatory or autoimmune disease in a subject, comprising contacting the subject's malignant cells or inflammatory cells with a therapeutically effective amount of a reagent (e.g., an antibody or nucleic acid) or a therapeutic composition of a reagent of the invention. The contacting step can occur by administration of the reagent or composition using any number of means available in the art. Typically, the reagent or composition is administered to the subject transdermally (e.g., by a transdermal patch or a topically applied cream, ointment, or the like), orally, subcutaneously, intrapulmonaryily, transmucosally, intraperitoneally, intrauterinely, sublingually, intrathecally, intramuscularly, intraarticularly, etc. using conventional methods. In addition, the reagent or composition can be administered via injectable depot routes such as by using 1-, 3-, or 6-month depot injectable or biodegrable materials and methods.

Regardless of the route of administration, the amount of the reagent administered or the schedule for administration will vary among individuals based on age, size, weight, condition to be treated, mode of administration, and the severity of the condition. One skilled in the art will realize that dosages are best optimized by the practicing physician and methods for determining dosage are described, for example in Remington's Pharmaceutical Science, latest edition. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical dose of the antibody used alone might range from about 1 μg/kg to up to 100 mg/kg of body weight or more per day, and preferably 1 μg/kg to up to 1 mg/kg, depending on the factors mentioned above. An intravenous injection of the antibody or fragment thereof, for example, could be 10 ng-1 g of antibody or fragment thereof, and preferably 10 ng-1 mg depending on the factors mentioned above. For local injection, a typical quantity of antibody ranges from 1 pg to 1 mg. Preferably, the local injection would be at an antibody concentration of 1-100 μg/ml, and preferably 1-20 μg/ml.

The nucleic acids of the invention can delivered to cells in a variety of ways. For example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$ pfu per injection. Ideally, a subject will receive a single injection. If additional injections are necessary, they can be repeated at six month intervals for an indefinite period and/or until the efficacy of the treatment has been established. As set forth herein, the efficacy of treatment can be determined by evaluating the clinical parameters.

The exact amount of the nucleic acid or vector required will vary as described above. Thus, it is not possible to specify an exact amount for every nucleic acid or vector. An appropriate amount can be determined by one of ordinary skill in the art using only routine experimentation given the teachings herein.

The invention further provides a therapeutic composition of the reagent of the invention. Such a composition typically contains from about 0.1 to 90% by weight (such as 1 to 20% or 1 to 10%) of a therapeutic agent of the invention in a pharmaceutically acceptable carrier. Solid formulations of the compositions for oral administration may contain suitable carries or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limtation, microcrystalline cellulose, corn starch, sodium starch, glycolate, and alginic acid. Table binders that may be used include acacia, methylcellulose, sodium carboxymethlcellulose, polyvinylpyrrolindone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble version of the compounds may be administered by the drip method, whereby a pharmaceutical formulation containing the antifungal agent and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as water-for-injection, 0.9% saline, or 5% glucose solution. A suitable insoluble form of the compound may be prepared and administered as a suspension in an aqueous base or a pharmaceutically acceptable oil base, such as an ester of a long chain fatty acid (e.g., ethy, oleate).

A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens.

The effectiveness of the method of treatment can be assessed by monitoring the patient for known signs or symptoms of the conditions being treated. For example, in the treatment of a malignancy of hematopoietic cell lineage, the reduction or stabilization of the number of abnormally proliferative cells would indicate successful treatment. In the treatment of arthritis, for example, a reduction in the amount of joint inflammation would indicate successful treatment. Thus, by "therapeutically effective" is meant an amount that provides the desired treatment effect.

The invention further provides a method of modulating a humoral immune response in a subject, comprising administering to the subject an isolated FcRH, an antibody, or nucleic acid of the invention. By "modulation" is meant either up-regulating or down-regulating. Thus, in the case of an allergic response, one skilled in the art would choose to down-regulate the humoral immune response. In the case of exposure of a subject to an infectious agent (e.g., a viral or bacterial agent), one skilled in the art would choose to upregulate the humoral antibody response.

Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE 1

Identification of FcRH1, FcRH2, and FcRH3

In order to isolation of FcRH cDNA Clones, rapid amplification of cDNA ends (RACE)-PCR was performed by using a Marathon-Ready™ human lymph node cDNA library (CLONTECH, Mountain View, Ca), Gene-specific primers were as follows: FcRH3, forward 5'-TGAGTCT-CAGGGTCACAGTTCCG -3' (SEQ ID NO41) and reverse 5'-GCTCTTGAACTTGGATATTTAGGGGT3' SEQ ID NO: 42); FcRH2, forward 5'-CCAGTGTATGTCAAT-GTGGGCTCTG3' (SEQ ID NO: 43) and reverse 5'-CGT-TGAAAGAGCTCTTGGACTTTTATC3' (SEQ ID NO:44); and FeRH 1, forward 5'-GCCTCAAAAGAAAAATAG-CAAGACGTT3' (SEQ ID NO: 45) and reverse 5'-AAGCT-CACATCAGCGACAGGGAC-3' (SEQ ID NO: 46). RACE products were subjected to a second round of nested PCR and visualized by agarose gel electrophoresis and ethidium bromide staining.

Primers used in end-to-end amplification to generate full-length cDNAs were as follows: FcRH3, forward 5'-TCTTGGAGATAAGTCGGGCTTT-3' (SEQ ID NO:47) and reverse 5'-ATCCTGCAGCCCAGCCTCGTAGGAG-3' (SEQ ID NO:48); FcRH2, forward 5'-GGTCCTCATGCT-GCTGTGGTCATT-3' (SEQ ID NO:49)and reverse 5'-GCT-GTTGATCTTCCCTTCTGATTC-3' (SEQ ID NO:50); and FcRH1, forward 5'-ATGCTGCCGAGGCTGTTGCT-GTTG3' (SEQ ID NO:51) and reverse 5'-CATAGCATCT-TCATAGTCCACATC-3' (SEQ ID NO:52). Each amplification reaction underwent initial denaturation of 94° C. for 30 s followed by 30 cycles of denaturation at 94° C. for 5 s and annealing at 68° C. for 4 min, and final extension at 72° C. for 6 min.

PCR. products were ligated into the pCR2.1 TOPO T/A vector (Invitrogen, Carlsbad, CA). Inserts were DNA-sequenced on both strands by the dideoxy chain termination method using Thermo Sequenase (Amersham Pharmacia, Piscataway, NJ) and an automated sequencer (Li-Cor, Lincoln, Nebr.). Nucleotide and amino acid sequence alignment was analyzed with a DNASTAR™ (DNAStar, Madison, Wis.) software package, and homology searches were performed by using BLASE (Altschul, S. F. et al. (1990) J. Mol. Biol. 215,403-410).

RNA blot analysis was subsequently performed. Northern blots (CLONTECH) were hybridized with 32P-dCTP-labeled probes: a 528-bp EcoRI fragment corresponding to the 5' untranslated (UT)-EC1 regions of the FcRH3 cDNA, a 200-bp PCR product corresponding to a portion of the 3' UT region of the FcRH2 cDNA, and a 257-bp PCR product corresponding to a portion of the 3' UT region of the FcRH1 cDNA. Membranes were hybridized for 1 h at 65° C., washed, and exposed to x-ray film (Kubagawa, H. et al. (1997) Proc. Natl. Acad. Sci. USA 94, 5261-5266).

Reverse transcription (RT)-PCR was performed Human tonsillar cells, obtained with Institutional Review Board approval, were separated into CD19+and CD19 subpopulations by magnetic cell sorting (Miltenyi Biotec, Auburn, Calif.). Viable CD19+ cells were stained with FITC-labeled anti-CD38 (Immunotech, Westhrook, Me.) and phycoerytbrin-labeled anti-IgD mAbs (Southern Biotechnology Associates, Birmingham, AL) before sorting cells with a FACSTARPLUS™ instrument (Becton Dickinson, Franklin Lakes, NJ) into TRIZOL® reagent (Life Technologies, Grand Island, N.Y. ) for RNA isolation. Total cellular RNA was primed with random hexamers and oligo(dT) primers and reverse-transcribed with SUPERSCRIPT™ II Invitrogen, Carlsbad, CA) into single stranded cDNA. RT-PCR was performed by using RNA from tonsillar B cells and cell lines, with GIBCO/BRL Taq polymerase (Life Technologies). The following gene-specific primer pairs were used in the RT-PCR analysis of FcRH1-5 expresion in cell lines and tonsillar B cell subpopulations: FcRH1 forward, 5'-CTC AACTTC ACA GTG CCT ACT GGG-3' (SEQ ID NO:53) and reverse, 5'-TCC TGC AGA GTC ACT AACCTT GAG-3' (SEQ ID NO:54): FcRH-2 forward, 5'-CCA GTG TAT GTC AAT GTG GGC TCT G (SEQ ID NO:55) and reverse, 5'-CAT TCT TCC CTC AAA TCT TTA CAC-3' (SEQ ID NO:56); FcRH3 forward, 5'-CAG CAC GTG GAT TCG AGT CDC-3' (SEQ ID NO:57) and reverse, 5'-CAG ATC TGG GAA TAA ATC GGG TTG3' (SEQ ID NO:58)fcRH4 forward, 5'-TCT TCA GAG ATC GGG AGG TGA-3' (SEQ ID NO:59) and reverse, 5'-TTT TGG GGT GTA CAT CAA CAT ACA AG-3' (SEQ ID NO:60); and FcRH forward, 5'-TGT TGC CCT GTT TCT TCC ATT ACA-3' (SEQ ID NO:61) and reverse, 5'CAG ACT TGG CCG ACC TAC GC-3' (SEQ ID NO:62) Each amplification reaction underwent initial denaturation at 94. degree, for 5 min followed by 35 cycles of denaturation at 94. degree for 30 s, annealing at 60 degree. for 30 s, extension at 72.degree. for 1 min, and final extension at 72. degree. for 7 min. Amplified products were visualized in 1% agarose gels containing ethidium bromide and documented with the BIO-RAD FLUOR-S™ IMAGER (Bio-Rad Laboratories, Hercules, CA).

The following human cell lines were used: REH and Nalm 16 pro-B cell lines (Korsmeyer, S. J. et al. (1983) J. Clin. Invest. 71, 301-313); 697, 207, and OB5 pre-B cell lines (Findley, H. W. et al. (1982) Blood 60, 1305-1309; Martin, D. et al. (1991) J. Exp. Med. 173, 639-645); Ramos, Daudi, and Raji B cell lines (Pulvertaft, R. J. V. (1964) Lancet 1, 238-240; Klein, E. et al. (1968) Cancer Res. 28, 1300-1310; Klein, G. et al. (1975) Intervirology 5, 319-33431-33); THP-1 and U937 monocytoid cell lines, HL-60 promyelocytic and KG-1 myelocytic cell lines, Jurkat T cell line and the K562 erythroid cell line (American Type Culture Collection).

A consensus sequence was generated that corresponds to the GenBank-derived amino terminal sequences of the second Ig-like domains of FcR (FcγRI and FcγRII/III) and the third Ig-like domain of the polymeric Ig receptor:GEPIXLRCHSWKDKXLXKVTYXQNGKAXKFFH (SEQ ID NO:63). A search of the National Center for Biotechnology Information protein database with this sequence identified two overlapping human genomic bacterial artificial chromosome (BAC) clones, AL135929 and AL356276, which are located at 1q21.2-22. The second clone contained three putative Ig superfamily genes encoding complementary amino acid sequences that were designated FcRH1, FcRH2, and FcRH3. See FIG. 1. The predicted amino acid sequences of these gene segments shared 23-57% identity with each other and 14-28% identity with human FcγRI (CD64). Further analysis of the FcRH locus led to the identification of two additional genes (FcRH4, and FcRH5) and one pseudogene (FcRH4ψ), immediately centromeric of FcRH1-3, two of which have recently been described as IRTA1 (FcRH4) and IRTA2 (FcRH5) (Hatzivassiliou, G. et al. (2001) Immunity 14, 277-289).

To determine whether these genes are expressed by lymphocytes, the predicted amino acid sequences of their protein products were used to search the Lymphochip expressed sequence tag database with the TBLASTN algorithm (Alizadeh, A. A. et al. (2000) Nature (London) 403, 503-511). Two expressed sequence tags (AA505046 and AA282433) were identified that share complete identity over 23 amino acids in their translated ORFs with the N terminus of FcRH1. Lymphochip microarray data analysis indicated that these expressed sequence tags are expressed at relatively high levels in peripheral lymphoid tissues, including the lymph nodes, tonsils, resting peripheral B cells, and normal germinal center (GC) B cells. Among the different lymphoid malignancies, their expression proved to be highest in chronic lymphocytic leukemias, follicular lymphomas, and some diffuse large cell lymphomas of B lineage.

Figure 2A:
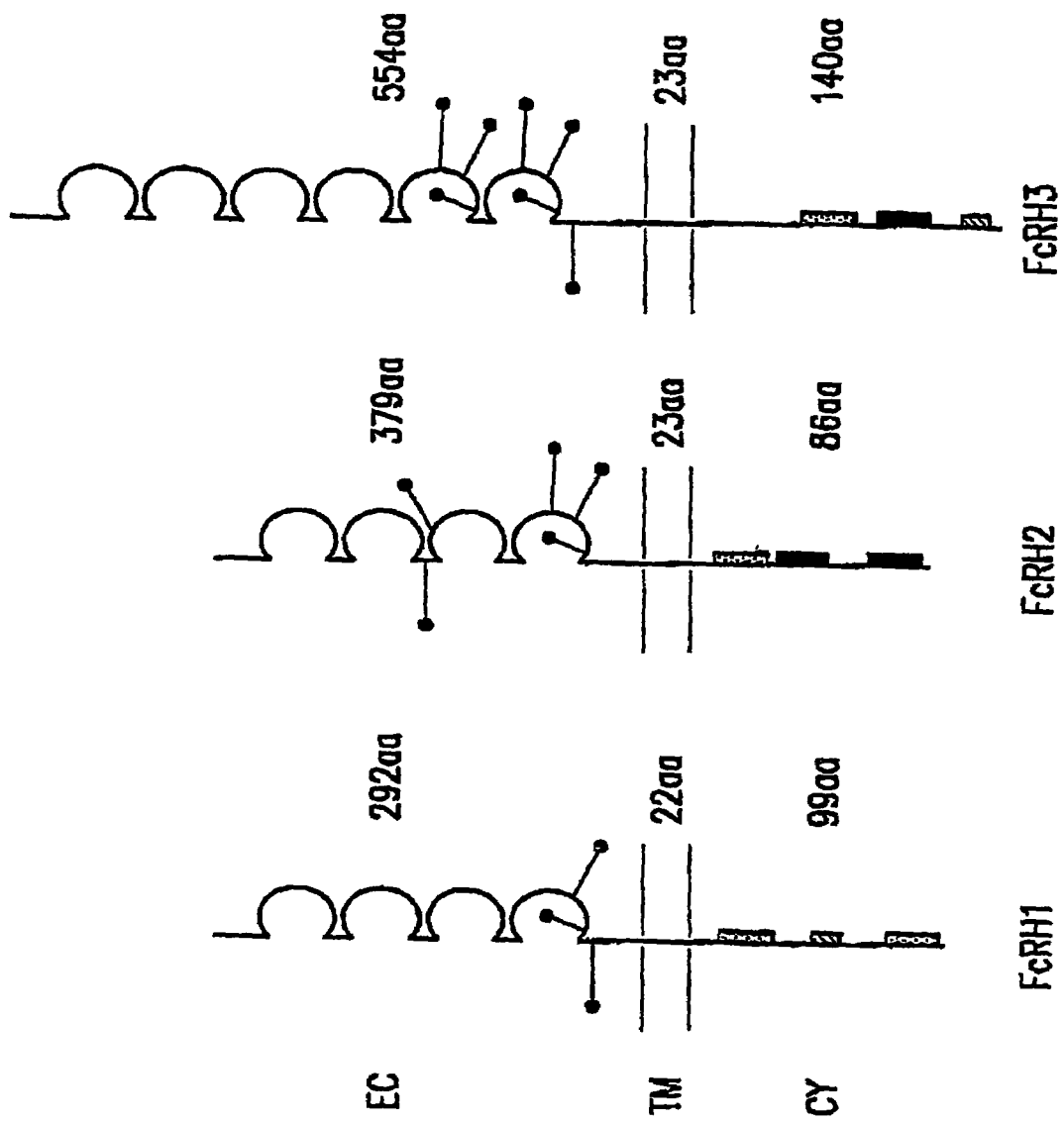
FIG. 2A is a schematic representation of FcRH molecules. The three cDNAs encode type I transmembrane proteins with similar extracellular domains, but different cytoplasmic regions. The extracellular (EC) regions contain different numbers of C2-like Ig domains and potential sites of N-linked glycosylation. The transmembrane (TM) domains are uncharged, except in the case of FcRH1. The cytoplasmic (CY) region of FcRH1 contains two ITAMs (light gray boxes) and one ITAM-like region (small, lined box), whereas FcRH2 contains one ITAM and two ITIMs (dark gray boxes). FcRH3 has a long cytoplasmic tail with one ITAM, one ITIM, and an ITAM-like region. The amino acid length of each region is indicated.
Figure 3:
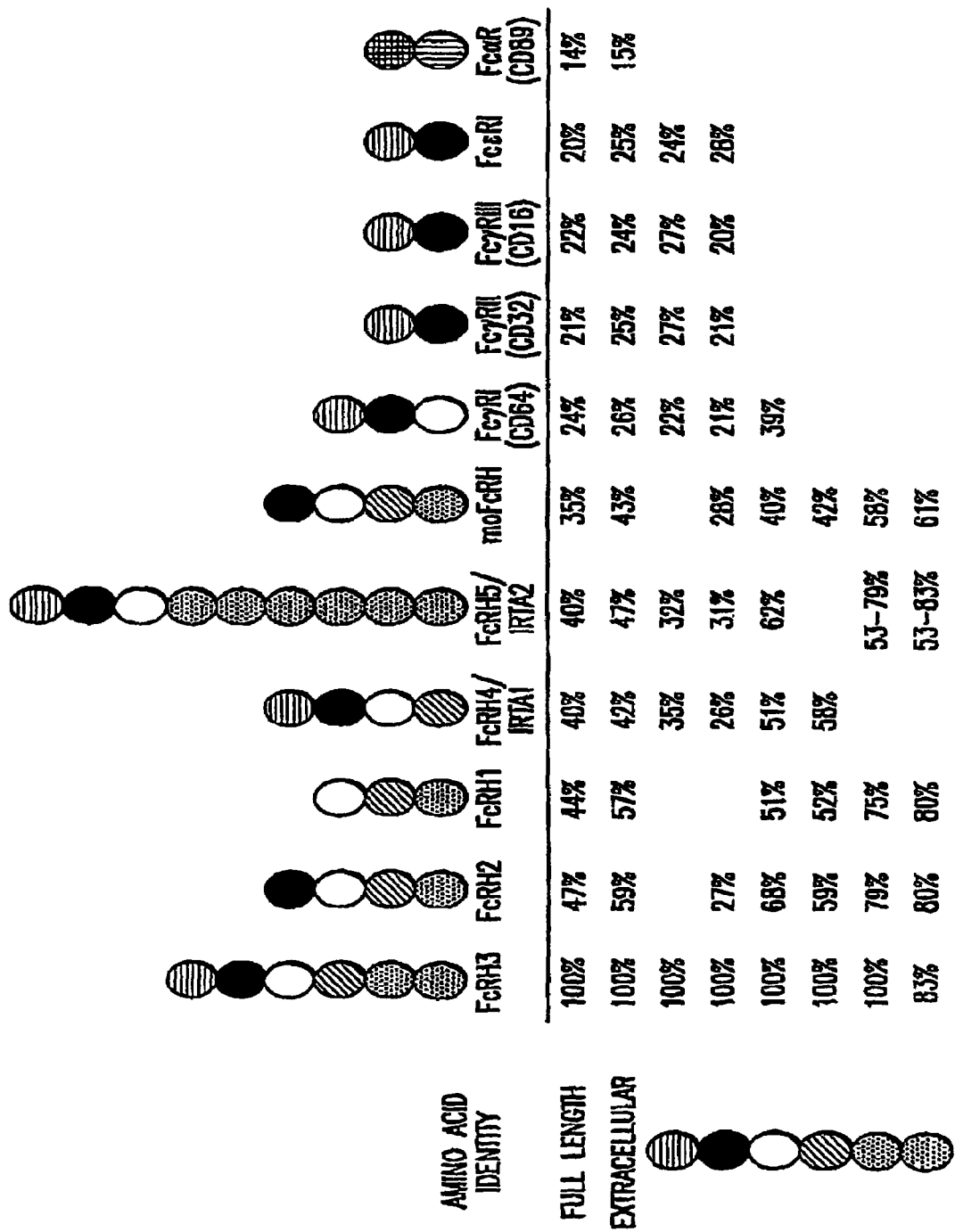
FIG. 3 shows a composite analysis of the extracellular homology among FcRH and FcR family members. Pairwise analysis of individual Ig-like subunits was performed with the CLUSTAL method algorithm using FcRH3 as the index of comparison. Individual homologous domains are coded to indicate relatedness. Percent amino acid identities for related domains are indicated and aligned in relation to the comparative FcRH3 subunit. The amino acid identity for the membrane proximal domains (light gray subunits) of FcRH5 are provided as the range of identity for all individually related domains. Comparisons that are not applicable are left blank Amino acid sequences were derived from IRTA1 (GenBank accession no. AF343659), IRTA2 (GenBank accession no. AF34364), moFcRH (GenBank accession no. AAG28775) FcγRI (GenBank accession no. AAA35678), FcγRII (Swiss-Prot accession no. P31994), FcγRIII (Swiss-Prot accession no. P08637), FcεRI (Swiss-Prot accession no. P12319), and FcαRI (Swiss-Prot accession no. P24071).

FcRH1, FcRH2, and FcRH3 cDNAs were isolated by RACE-PCR from a human lymph node cDNA library in both 5' and 3' directions. Full-length cDNAs of the coding regions for FcRH1, FcRH2, and FcRH3 were obtained by end-to-end PCR using unique primers generated from the cDNA sequences delineated for the 5' UT and 3'UT regions. Southern blot analysis of human genomic DNA digested with BamHI, EcoRI, or HindIII using cDNA probes specific for the 3' UT regions of each cDNA revealed either one or two hybridizing fragments, suggesting that FcRH1, FcRH2, and FcRH3 are encoded by single genes. Analysis of full-length cDNA sequences indicated that FcRH1, FcRH2, and FcRH3 have ORFs of 1,287 bp, 1,524 bp, and 2,202 bp, respectively, and encode type I transmembrane proteins of 429 aa, 508 aa, and 734 aa, respectively. Based on predicted consensus signal peptide cleavage sites (Von Heijne, G. (1986) Nucleic Acid Res. 14, 4683-4690; Nielsen, H. (1997) Protein Eng. 10, 1-6), the relative core peptide molecular masses were estimated as 45,158 for FcRH1, 53,407 for FcRH2, and 78,849 for FcRH3. These type I transmembrane proteins possess 3-6 extracellular C2 (Williams, A. F. & Barclay, A. N. (1988) Annu. Rev. Immunol. 6, 381-405;

Bork, P. et al. (1994) J. Mol. Biol. 242, 309-320; Vaughn, D. E. & Bjorkman, P. J. (1996) Neuron 16, 261-273) type Ig-like domains with 3-7 potential N-linked glycosylation sites, uncharged transmembrane segments, and relatively long cytoplasmic tails containing consensus motifs for ITIMs and/or ITAMs. See FIG. 2A.

Multiple alignment analysis of the translated cDNAs, using FcRH3 as the index sequence of comparison, indicates that FcRH1, FcRH2, and FcRH3 have highly conserved hydrophobic signal peptides and corresponding Ig-like extracellular domains (FIG. 2B). Their hydrophobic transmembrane (uncharged with the exception of FcRH1 which includes an acidic domain) domains (Sonnhammer, E. L. L. et al. (1998) in A Hidden Markov Model for Predicting Transmembrane Helices in Protein Sequences, eds. Glasgow, J., Littlejohn, T., Major, F., Lathrop, R., Sankoff, D. & Sensen, C. (Am. Assoc. for Artificial Intelligence, Menlo Park, Calif.), pp. 175-182) are also well conserved, but their cytoplasmic domains are not. FcRH1 has a long cytoplasmic tail containing three potential ITAMs, the first and third of which fit the consensus sequence (E/D)-X-X-Y-X-X-(L/I)-$X_{6-8}$-Y-X-X-(L/I) (SEQ ID NO:64, with six amino acid between the consensus sequences; SEQ ID NO:65, with seven amino acid residues between the consensus sequences; and SEQ ID NO:66, with eight amino acid residues between the consensus sequences), whereas, the second has only one tyrosine residue. The shorter cytoplasmic domain of FcRH2 contains one potential ITAM and two ITIM consensus sequences (I/V/L/S)-X-Y-X-X-(L/V) (SEQ ID NO:67) separated by 22 amino acids. FcRH3 has the longest cytoplasmic tail. It contains one potential ITAM, one ITIM, and another potential ITAM that also has a single tyrosine residue.

An RNA blot analysis with gene-specific probes was performed on 16 human tissues, including six primary or secondary lymphoid tissues. RNA blots were analyzed with discriminating $\alpha^{32}$P-dCTP-labeled probes generated from the respective FcRH cDNAs. The following probes were used: (Top) a PCR-generated, 257-bp probe specific to the 3' UT region of FcRH1; (Middle) a PCR-generated, 290-bp probe corresponding to the 3' UT region of FcRH2; and (Bottom) a 528-bp EcoRI-digested fragment of the 5' end of the FcRH3 cDNA corresponding to its 5' UT region, S1, S2, and EC1 domains. The relative mRNA abundance was indicated by β-actin probe. All three FcRH gene probes hybridized with transcripts in the secondary lymphoid organs, spleen and lymph node. An FcRH1-specific probe hybridized with spleen and lymph node transcripts of about 3.5 kb and about 6.0 kb. Additional hybridization bands of about 0.7 kb and about 1.5 kb were observed for heart, skeletal muscle, kidney, liver, and, in less abundance, placental tissue. Larger transcripts also were seen in skeletal muscle (about 6.0 kb) and in kidney and placenta (about 4.4 kb). An FcRH2-specific probe hybridized to about 3.0-kb, about 4.4-kb, and about 5.5-kb transcripts most abundantly in spleen and lymph node. A transcript of approximately 2.4-kb was notable in the kidney. An FcRH3 probe hybridized with about 3.5-kb, about 5.5-kb, and about 7.0-kb transcripts chiefly in spleen and lymph node. These also were seen, albeit in lesser abundance, in peripheral blood lymphocytes, thymus, and bone marrow samples. Additionally, a unique transcript of about 1.35 kb was evident in skeletal muscle. These results indicated expression of FcRH1, FcRH2, and FcRH3 in peripheral lymphoid organs, whereas tissue specific differences in alternative splicing or polyadenylation were suggested by the differential expression of transcripts with variable size in nonlymphoid tissues. RTPCR analysis to date of non-lymphoid tissue skeletal muscle, however, does not reveal transcripts despite the Northern analysis results.

When FcRH expression was examined by RT-PCR analysis of cell lines representing different hematopoietic lineages, FcRH1, FcRH2, and FcRH3 expression was found in every mature B cell line tested (Table 2). FcRH2 and FcRH3 expression was limited to the mature B cell lines and not seen in the other types of cells examined. In contrast, FcRH1 expression was seen in pro-B, T, and myeloid cell lines, although not in an erythroid cell line.

TABLE 2

Expression of FcRH transcripts in human B cell lines

| Cell Type | Cell line | FcRH1 | FcRH2 | FcRH3 |
|---|---|---|---|---|
| Pro-B | REH | + | − | − |
|  | Nalm 16 | + | − | − |
| Pre-B | 697 | − | − | − |
|  | 207 | − | − | − |
|  | OB5 | − | − | − |
| B | Ramos | + | + | + |
|  | Daudi | + | + | + |
|  | Raji | + | + | + |
| T | Jurkat | + | − | − |
| Monocytic | THP-1 | + | − | − |
| Myelomonocytic | U937 | + | − | − |
| Promyelocytic | HL-60 | + | − | − |
| Myelocytic | KG-1 | + | − | − |
| Erythroid | K562 | − | − | − |

FcRH1, FcRH2, and FcRH3 expression in cell lines was determined by RT-PCR.

RT-PCR analysis of sorted populations of peripheral blood cells indicated that FcRH1, FcRH2, FcRH3, and FcRH5 are expressed at relatively high levels in CD19+ B cells, whereas FcRH4 was expressed at only trace levels. FcRH3 expression was observed in CD3+ T cells whereas transcripts of FcRH1 were barely detectable. FcRH1 expression also was observed in circulating granulocytes.

To refine the analysis of FcRH expression in secondary lymphoid tissues, tonsillar lymphocyte subpopulations were isolated. The five discrete subpopulations of B lineage cells, which can be distinguished by their differential expression of cell surface IgD and CD38, represent different stages in B cell differentiation: follicular mantle (IgD+CD38), pre-GC (IgD+CD38+), GC (IgDCD38+), memory (IgDCD38), and mature plasma cells (CD38$^2$+) (Pascual, V. (1994) J. Exp. Med. 180: 329-339). RT-PCR analysis of FcRH1-5 expression in tonsillar B cell subpopulations was performed. Viable cells were magnetically sorted into CD19− non-B cells and CD19+ B cells. The latter were stained with anti-IgD and anti-CD38 mAbs, and the five subpopulations indicated (CD38−IgD−, CD38−IgD+, CD38+IgD+, CD38+IgD−, and CD38$^2$+) were sorted by flow cytometry. RT-PCR analysis of FcRH transcripts in non-B cells and the B cell subpopulations was also performed. After cDNA preparation, PCR amplification was performed on the equivalent template of approximately 10 k cells. Glyceraldehyde-3-phosphate dehydrogenase (GADPH) was amplified as a positive control.

RT-PCR analysis indicated little or no expression of FcRH transcripts in the non-B lineage CD19− cells, most of which are T cells. However, CD19+ subpopulations displayed coordinate expression of FcRH1, FcRH2, and FcRH3 transcripts in follicular mantle, naïve, GC, and memory B cell subpopulations, but yielded no evidence of FcRH transcripts in pre-GC B cells or plasma cells. In contrast, FcRH4 transcripts were restricted to the follicular mantle and memory B cells, whereas FcRH5 expression extended to mature plasma cells.

The relationship between the five FcRHs was examined by comparing their full-length, extracellular, and individual Ig-like domain amino acid sequences. This analysis, which included a recently identified mouse FcRH ortholog (moFcRH) and members of the FcR family, used the CLUSTAL method algorithm (Higgins, D. G. & Sharp, P. M. (1989) Comput. Appl. Biosci. 5, 151-153). Comparison of the full-length sequences of other FcRH family members with FcRH3 indicated 40-47% identity. By comparison, the degree of FcRH3 homology with the moFcRH was found to be 35% and 21-24% with FcR members residing on chromosome 1, FcγRI, FcγRII, FcγRIII, and FcεRI. A lower level of amino acid identity (14%) was observed for the chromosome 19 LRC member, FcαR. A slightly higher degree of extracellular homology was evident. Pairwise analysis of the individual Ig-like subunits indicated conservation in membrane-distal to membrane-proximal ordering of extracellular domain composition among family members. Although similar Ig domain subunits were shared among family members, the individual receptors were found to be composed of unique domain combinations. The extracellular domain configuration of the moFcRH most closely resembled that of FcRH2, with which it has 46% identity. The extended pairwise comparison of the FcRH family with known FcRs suggested the conservation of these Ig-like domains to some degree throughout the greater family. The resemblance is particularly evident in the FcRH3 membrane-distal domains that correspond to the three FcγRI domains and the two domains of FcγRII, FcγRIII, and the FcR γ-chain. This analysis suggests the ancestral occurrence of differential duplication and diversification of the individual Ig-like subunits in the respective FcRH family members. The data also indicate that the FcRHs are more similar to their FcR neighbors on chromosome 1 than to their FcR relative on chromosome 19.

The genomic sequence analysis of relevant chromosome 1q21 BAC clones indicated that the entire FcRH locus spans 300 kb. The FcRH genes lie in the same transcriptional orientation toward the centomere. Exon-intron boundaries were characterized by sequence comparison of their respective cDNA clones and the AG/GT rule. The FcRH1 gene consists of 11 exons and 10 introns spanning about 28 kb. The first exon, 5' UT/S1, encodes the 5' UT region, the ATG translation initiation codon, and the first half of a split signal peptide. S2, the second exon, is separated from 5' UT/S1 by a long intron of 12.9 kb and, like the neighboring FcRs, is 21 bp in length (van de Winkel, J. G. & Capel, P. J. (1993) Immunol. Today 14, 215-221; Kulczycki, A., Jr. et al. (1990) Proc. Natl. Acad. Sci. USA 87, 2856-2860; Pang, J. et al. (1994) J. Immunol. 151, 6166-6174.). The extracellular region is encoded by three closely clustered exons, EC1-EC3, that code for the three Ig-like domains. The membrane-proximal, transmembrane, and the proximal portion of the cytoplasmic domain are encoded by a single sixth exon, TM. The cytoplasmic tail is encoded by five exons, CY1-CY5, and the CY5 also encodes the beginning of the 3' UT region.

FcRH2 contains 12 exons and 11 introns that span 30 kb. It also contains two exons that encode a split signal peptide, the first of which, 5'UT/S1, includes the 5' UT region, the ATG translation initiation codon, and first half of the signal peptide. The second exon, S2, is 21 bp in length. Exons 3-6 encode the four extracellular domains, EC1-EC4. The seventh exon encodes the membrane-proximal, transmembrane, and the proximal portion of the cytoplasmic domain. The FcRH2 cytoplasmic tail is encoded by five exons, CY1-CY5, the last exon of which includes the termination of the ORF and beginning of the 3' UT region.

The FcRH3 gene consists of 16 exons and 15 introns that span about 24 kb. Unlike FcRH1 and FcRH2, its 5' UT region is encoded by two exons, 5' UT1 and a second, 5'UT2/S1, that also encodes the ATG translation initiation codon and the beginning of the split signal peptide. The third exon, S2, is also 21 bp in length. Extracellular domains encoded by six exons, EC1-EC6, are followed by exon 10 that encodes the membrane-proximal, transmembrane, and the proximal portion of the cytoplasmic domain. The cytoplasmic tail is encoded by five exons, CY1-CY5; the last contains the beginning of the 3' UT region.

EXAMPLE 2

Identification of HuFcRH6

FcRH6 is located in the midst of the classical FcRs at 1q21-23. Its genomic structure indicates, like the classical FcRs and FcRH1-5, a split hydrophobic signal peptide encoded by two exons the second of which is 21 bp.

FcRH6 was characterized using the methods described in Example 1. A composite analysis of Ig-like domains for relatedness with the other huFcRHs was performed. See Figure xxx. Sequence analysis of huFcRH6 indicates its type I transmembrane form contains a consensus motif for a single ITAM, or a single or two ITIM's.

Initial RT-PCR analysis of huFcRH6 in human tissues and cell lines (as described in Example 1) reveals transcript expression in normal tonsil and lymph nodes. In cell lines, expression of huFcRH6 was identified in myeloid cell lines THP-1 (monocytic), U937 (myelomonocytic), and KG-1 (myelocytic). Limited expression if any was identified in the 207 pre-B cell line and the Daudi B cell line.

EXAMPLE 3

Generation of Transfectants and Antibodies

Recombinant constructs for transfection and stable expression of huFcRH1-5 have been generated. The constructs have been ligated into a CMV driven mammalian expression vector with and without green fluorescent protein (GFP) fusion at the carboxyl terminus. Surface expression of huFcRH1 and huFcRH3 was detected for both GFP and non-GFP forms by staining with antibody supernatant. The antibody supernatant was derived from hybridomas generated by mice immunized with recombinant extracellular protein of the respective FcRH. The constructs for huFcRH2, 4, and 5 have been detected by green fluorescence as well as surface expression for FcRH4.

Monoclonal antibodies have been generated, including, for example, an antibody that binds FcRH1. The preliminary analysis of FACS staining for FcRH1 expression with monoclonal antibody 1-5A3 labeled with a FITC conjugate (mouse anti human FcRH1) in peripheral blood from normal volunteers indicates virtually all CD19+ B cells have huFcRH1 expression, as do CD14+ monocytes and CD13+ granulocytes. CD3+ T cells have limited to no expression of FcRH1. Staining of B-CLL samples from two different patient peripheral blood samples indicates that virtually all CD5+/CD19+ B-CLL cells are positive for the FcRH1-5A3 antigen. By western blot analysis of recombinant protein for FcRH1-5 extracellular regions 1-5A3 appears specific for FcRH1. 1-5A3 also stains B cell lines Daudi and Raji.

EXAMPLE 4

Identification of MoFcRH1-3

Figure 4:
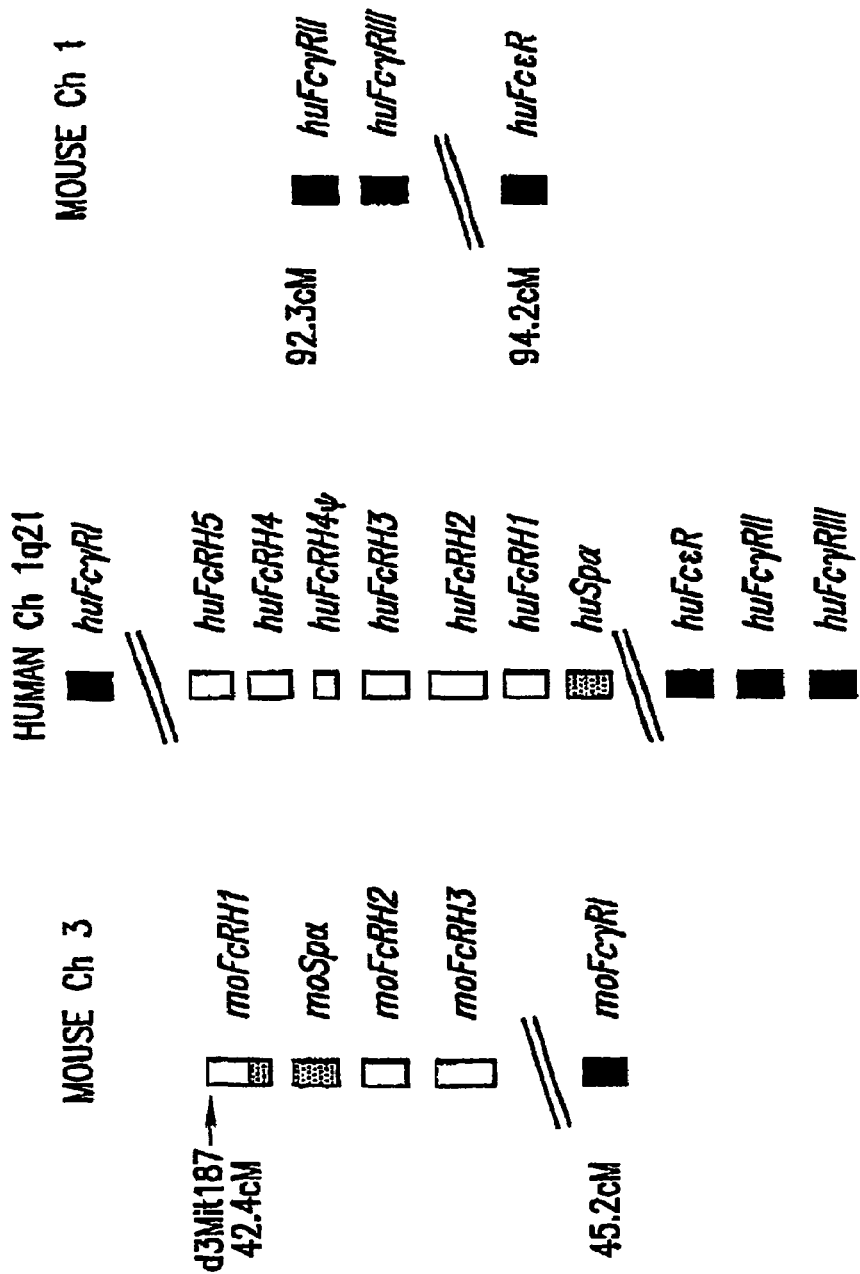
FIG. 4 shows the relative location of the mouse FcR family. Location is indicated in reference to the human FcR related genes at Ch 1q21-23 and their orthologous loci on mouse Ch 3 and Ch 1. The microsatellite marker d3Mit187 is located within moFcRH1.

A family of three mouse Fc Receptor Homologs (MoFCRHs) were identified and cloned. Amino acid sequences from the membrane proximal Ig like domains of huFcRH1-5 were used to identify putative mouse FcRH orthologs in the NCBI or Celera genomic, EST, and protein databases using the protein BLAST (BLASTP) and the translated nucleotide BLAST (TBLASTN) algorithms, respectively. The location of moFcR family is split between chromosomes 1 and 3 in regions syntenic with human chromosome 1q21-23. See FIG. 4. The mo FcRH are located on mouse 13. Approximate position were determined from Genbank, Celera, and Mouse Genome informatics databases, Contings of ESTs were generated to determine the putative cDNA sequences.

Genomic organization was determined by comparing cDNA clones generated from RACE PCR with GenBank and Celera genomic sequences, DNASTAR™ software DNAStar, MADISON, WI.) was used for analysis of exon-intron boundaries which were characterized by sequence comparison and the AG/GT rule. All three genes contain a split signal sequence with a 21 bp S2 exon (exon 2) which is found in all FcR and huFcRH genes on human chrumosone 1.

Figure 6:
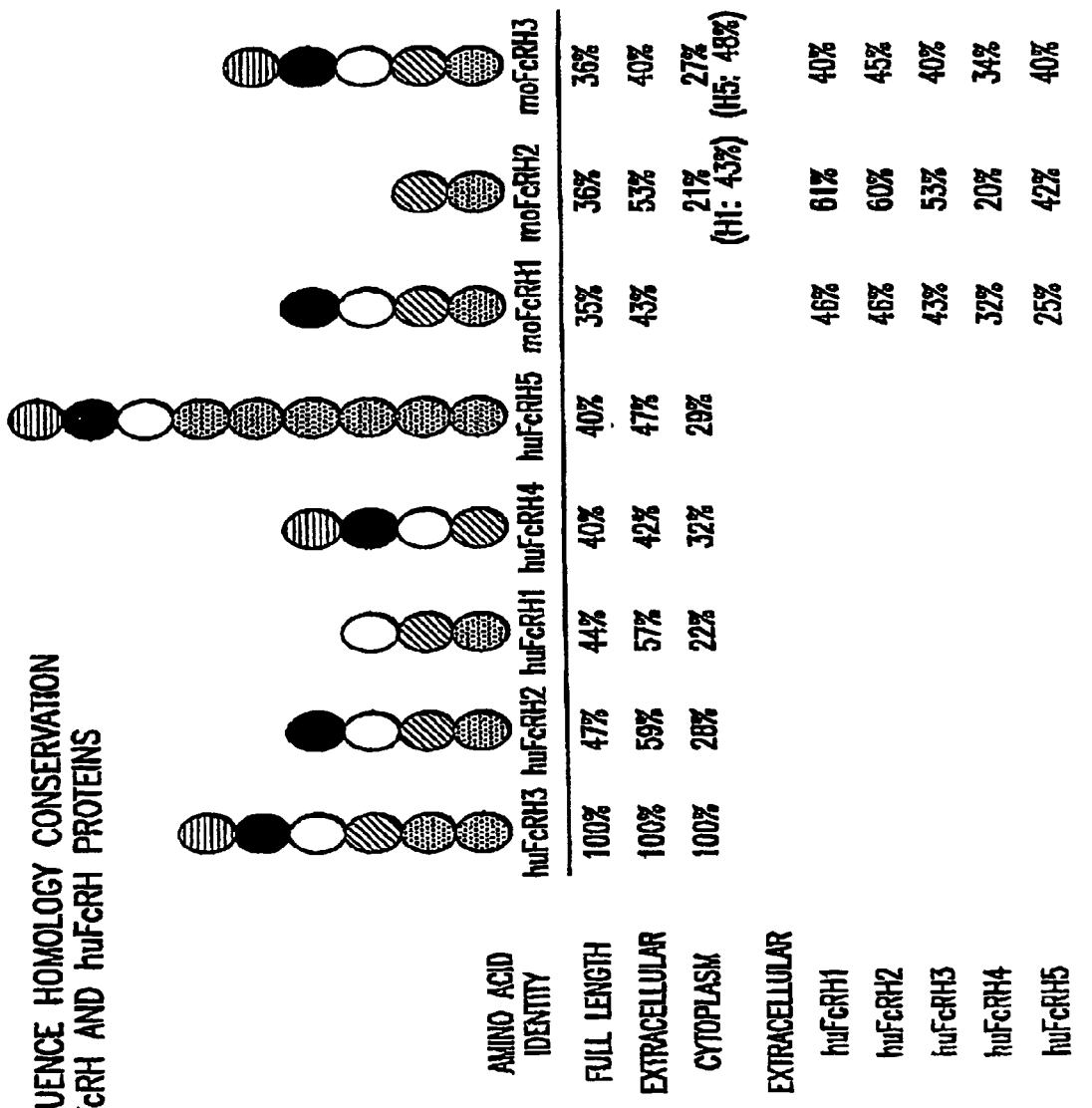
FIG. 6 shows domains marked to indicate relatedness of the Ig-like subunits. Ig-like domain homology was determined by generation of a phylogenetic tree using DNAStar software with the CLUSTAL program and assigning arbitrary colors to individual Ig-domains of a given branch. Amino acid identities for full length, extracellular and, cytoplasmic domain comparisons are based on huFcRH3. Closest cytoplasmic relatives are indicated in parentheses. Most identical extracellular comparisons between mouse and human relatives are highlighted in horizontal lines. Comparisons that are not applicable are left blank.
Figure 7:
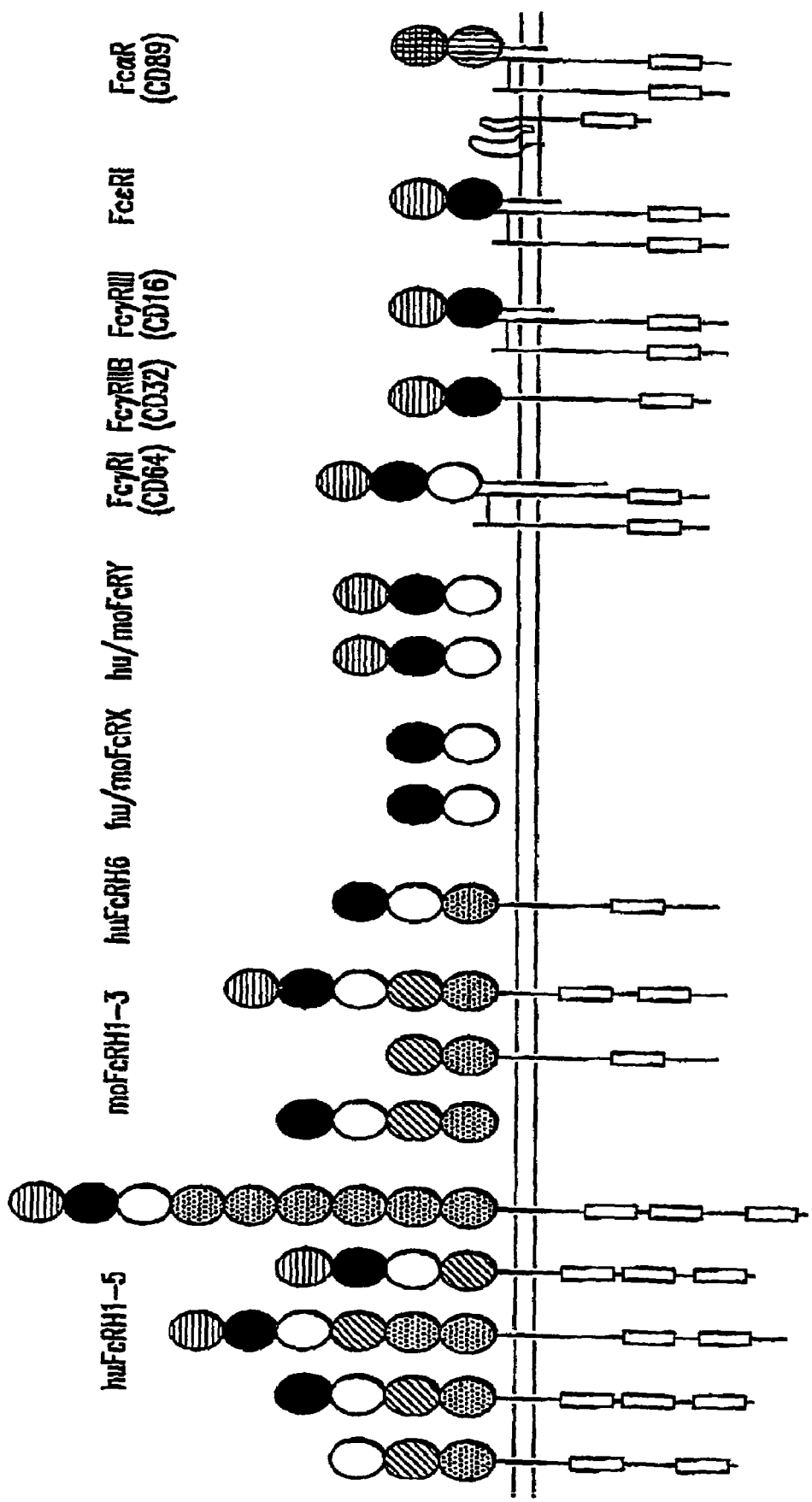
FIG. 7 shows the domains of huFcRH1-6, moFcRH1-3 and related proteins. Domains are colored to indicate relatedness of the Ig-like subunits. Ig-like domain homology was determined by generation of a phylogenetic tree using DNAStar software with the CLUSTAL program and assigning arbitrary colors to individual Ig-domains of a given branch. Amino acid identities for fill length, extracellular and, cytoplasmic domain comparisons are based on huFcRH3. Closest cytoplasmic relatives are indicated in parentheses. Most identical extracellular comparisons between mouse and human relatives are highlighted in red. Comparisons that are not applicable are left blank.

A comparison of tyrosine based motifs in FcRH cytoplasmic tails indicated homology with the huFcRH family. See FIG. 5. An analysis of sequence homology conservation is further shown in FIGS. 6 and 7.

Expression of the moFcRHs in tissue and cell lines was also characterized as described in Example 1. Briefly, RT-PCR was performed on mouse tissues and cell lines with gene specific primers. Viable tissue was placed in TRIZOL® reagent (Molecular Research Center Cinncinnati, OH) for RNA extraction. After cDNA preparation PCT amplification was performed on equivalent template amounts. Actin was amplified as a positive control. McFcRH3 appears to have preferential expression in cells of B lineage. The results are shown in Tables 3-4.

TABLE 3

Tissue Distribution of moFcRH Expression

| TISSUE | MoFcRH1 | MoFcRH2 | MoFcRH3 |
|---|---|---|---|
| Bone Marrow | + | + | + |
| Thymus | + | + | + |
| Spleen | + | + | + |
| Lymph Node | + | + | + |
| Peyer's Patches | + | + | + |
| Peripheral Blood | + | + | + |
| Brain | + | − | − |
| Liver | + | + | − |
| Heart | + | − | − |
| Muscle | + | − | − |
| Kidney | + | − | − |
| Lung | + | + | − |
| Intestine | + | + | + |
| Testes | + | − | − |

TABLE 4

Expression of moFcRH transcripts in cell lines

| Cell Type | Cell line | FcRH1 | FcRH2 | FcRH3 |
|---|---|---|---|---|
| Pro-B | SCID7 | + | +/− | + |
|  | Raw8.1 | + | + | − |
| Pre-B | 70Z/3 | + | + | + |
|  | BC76 | − | + | + |
|  | 18-81 | + | + | + |
| Imm. B | WEHI-231 | + | + | + |
|  | WEHI-279 | + | + | + |
| B | A20 | + | + | + |
|  | X16C8.5 | + | + | + |
| T | EL4 | + | +/− | −/+ |
| NKT | NKT | + | +/− | − |
| NKT | 2C12 | + | +/− | − |
| Myeloid | WEHI-3 | + | − | − |
| Lymphoid | YAC-1 | + | + | − |
| Fibroblast | 3T3 | + | +/− | − |

Expression in cell lines was determined by RT-PCR.

Figure 8:
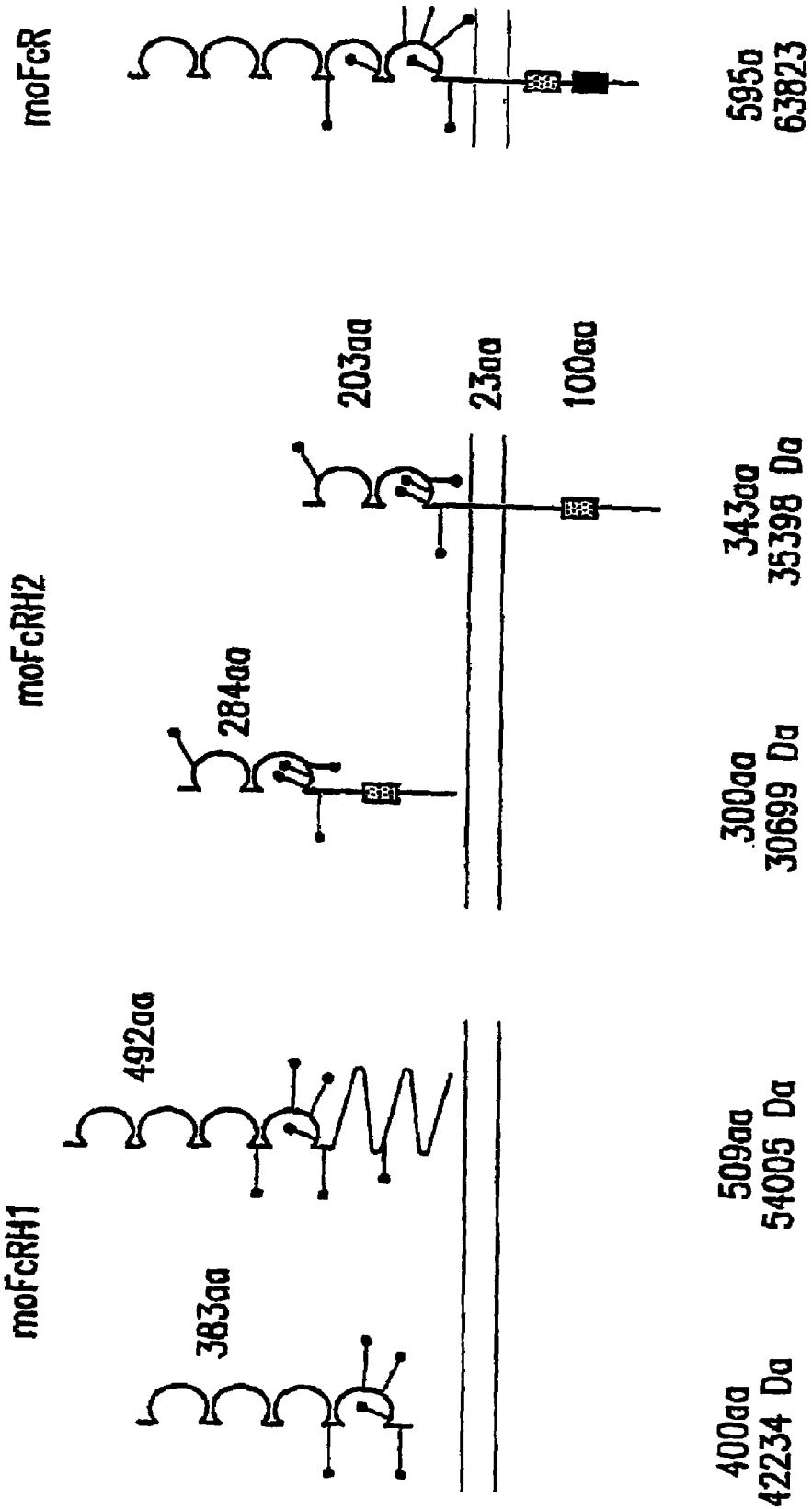
FIG. 8 shows the structural characteristics of the mouse FcRH isoforms.

The mouse FcReceptor Homologs include secreted or type I transmembrane isolfrms that have unique cytoplasmic tails with potential activation and inhibition motifs. Their chromosomal location, Ig domain homology, and genomic organization indicate the mouse FcReceptor Homologs are orthologs of the huFcRH that have evolved a significant level of diversity. moFcRH1, moFcRH2, and moFcRH3 are predicted to encode secreted or type I transmembrane proteins based on their amino acid sequences. moFcRH1 has two secreted isoforms both of which have extracellular (EC) regions of four Ig-like domains with five potential sites for N-linked glycosylation. One isoform is a fusion protein with a type B scavenger receptor domain containing 8 cysteines. moFcRH2 has secreted and type I isoforms containing two Ig-like domains with five N-linked glycosylation sites. The type I isoform has an uncharged transmembrane region which the secreted isoform lacks. Both isoforms contain the cytoplasmic portion which is long in the transmembrane form and contains five tyrosines including a consensus sequence for one potential immunoreceptor tyrosine-based activating motif. moFcRH3 contains five Ig-like domains with six potential sites of N-linked glycosylation. Its transmembrane domain is also uncharged and the cytoplasmic region contains one potential ITAM and one potential immunoreceptor tyrosine-based inhibitory motif. The amino acid (aa) length of individual regions and full length (FL) isoforms, as well as approximate molecular weight (MW) in Daltons (Da), is indicated in the structural diagram of FIG. 8.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated FcRH6 comprising the amino acid sequence of SEQ ID NO:28.

* * * * *

SEQUENCE LISTING

<160> NUMBER OF SEQ ID NOS: 102

<210> SEQ ID NO 1
<211> LENGTH: 99
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 1

Lys Arg Lys Ile Gly Arg Arg Ser Ala Arg Asp Pro Leu Arg Ser Leu
1               5                   10                  15

Pro Ser Pro Leu Pro Gln Glu Phe Thr Tyr Leu Asn Ser Pro Thr Pro
            20                  25                  30

Gly Gln Leu Gln Pro Ile Tyr Glu Asn Val Asn Val Val Ser Gly Asp
        35                  40                  45

Glu Val Tyr Ser Leu Ala Tyr Tyr Asn Gln Pro Glu Gln Glu Ser Val
50                  55                  60

Ala Ala Glu Thr Leu Gly Thr His Met Glu Asp Lys Val Ser Leu Asp
65                  70                  75                  80

Ile Tyr Ser Arg Leu Arg Lys Ala Asn Ile Thr Asp Val Asp Tyr Glu
                85                  90                  95

Asp Ala Met

<210> SEQ ID NO 2
<211> LENGTH: 413
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 2

Ala Glu Leu Phe Leu Ile Ala Ser Pro Ser His Pro Thr Glu Gly Ser
1               5                   10                  15

Pro Val Thr Leu Thr Cys Lys Met Pro Phe Leu Gln Ser Ser Asp Ala
            20                  25                  30

Gln Phe Gln Phe Cys Phe Phe Arg Asp Thr Arg Ala Leu Gly Pro Gly
        35                  40                  45

Trp Ser Ser Ser Pro Lys Leu Gln Ile Ala Ala Met Trp Lys Glu Asp
        50                  55                  60

Thr Gly Ser Tyr Trp Cys Glu Ala Gln Thr Met Ala Ser Lys Val Leu
65                  70                  75                  80

Arg Ser Arg Arg Ser Gln Ile Asn Val His Arg Val Pro Val Ala Asp
                85                  90                  95

Val Ser Leu Glu Thr Gln Pro Pro Gly Gly Gln Val Met Glu Gly Asp
            100                 105                 110

Arg Leu Val Leu Ile Cys Ser Val Ala Met Gly Thr Gly Asp Ile Thr
        115                 120                 125

Phe Leu Trp Tyr Lys Gly Ala Val Gly Leu Asn Leu Gln Ser Lys Thr
    130                 135                 140

Gln Arg Ser Leu Thr Ala Glu Tyr Glu Ile Pro Ser Val Arg Glu Ser
145                 150                 155                 160

Asp Ala Glu Gln Tyr Tyr Cys Val Ala Glu Asn Gly Tyr Gly Pro Ser
                165                 170                 175

```
Pro Ser Gly Leu Val Ser Ile Thr Val Arg Ile Pro Val Ser Arg Pro
            180                 185                 190

Ile Leu Met Leu Arg Ala Pro Arg Ala Gln Ala Ala Val Glu Asp Val
            195                 200                 205

Leu Glu Leu His Cys Glu Ala Leu Arg Gly Ser Pro Pro Ile Leu Tyr
            210                 215                 220

Trp Phe Tyr His Glu Asp Ile Thr Leu Gly Ser Arg Ser Ala Pro Ser
225                 230                 235                 240

Gly Gly Gly Ala Ser Phe Asn Leu Ser Leu Thr Glu His Ser Gly
            245                 250                 255

Asn Tyr Ser Cys Glu Ala Asn Asn Gly Leu Gly Ala Gln Arg Ser Glu
            260                 265                 270

Ala Val Thr Leu Asn Phe Thr Val Pro Thr Gly Ala Arg Ser Asn His
            275                 280                 285

Leu Thr Ser Gly Val Ile Glu Gly Leu Leu Ser Thr Leu Gly Pro Ala
            290                 295                 300

Thr Val Ala Leu Leu Phe Cys Tyr Gly Leu Lys Arg Lys Ile Gly Arg
305                 310                 315                 320

Arg Ser Ala Arg Asp Pro Leu Arg Ser Leu Pro Ser Pro Leu Pro Gln
            325                 330                 335

Glu Phe Thr Tyr Leu Asn Ser Pro Thr Pro Gly Gln Leu Gln Pro Ile
            340                 345                 350

Tyr Glu Asn Val Asn Val Val Ser Gly Asp Glu Val Tyr Ser Leu Ala
            355                 360                 365

Tyr Tyr Asn Gln Pro Glu Gln Glu Ser Val Ala Ala Glu Thr Leu Gly
            370                 375                 380

Thr His Met Glu Asp Lys Val Ser Leu Asp Ile Tyr Ser Arg Leu Arg
385                 390                 395                 400

Lys Ala Asn Ile Thr Asp Val Asp Tyr Glu Asp Ala Met
            405                 410

<210> SEQ ID NO 3
<211> LENGTH: 86
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 3

His Lys Ile Ser Gly Glu Ser Ser Ala Thr Asn Glu Pro Arg Gly Ala
1               5                   10                  15

Ser Arg Pro Asn Pro Gln Glu Phe Thr Tyr Ser Ser Pro Thr Pro Asp
            20                  25                  30

Met Glu Glu Leu Gln Pro Val Tyr Val Asn Val Gly Ser Val Asp Val
            35                  40                  45

Asp Val Val Tyr Ser Gln Val Trp Ser Met Gln Gln Pro Glu Ser Ser
    50                  55                  60

Ala Asn Ile Arg Thr Leu Leu Glu Asn Lys Asp Ser Gln Val Ile Tyr
65                  70                  75                  80

Ser Ser Val Lys Lys Ser
            85

<210> SEQ ID NO 4
<211> LENGTH: 489
<212> TYPE: PRT
```

<213> ORGANISM: Artificial Sequence
<220> FEATURE:
<223> OTHER INFORMATION: Description of Artificial Sequence:/note = synthetic construct

<400> SEQUENCE: 4

```
Leu Thr Leu Val Ala Pro Ser Ser Val Phe Glu Gly Asp Ser Ile Val
 1               5                  10                  15

Leu Lys Cys Gln Gly Glu Gln Asn Trp Lys Ile Gln Lys Met Ala Tyr
            20                  25                  30

His Lys Asp Asn Lys Glu Leu Ser Val Phe Lys Lys Phe Ser Asp Phe
        35                  40                  45

Leu Ile Gln Ser Ala Val Leu Ser Asp Ser Gly Asn Tyr Phe Cys Ser
 50                  55                  60

Thr Lys Gly Gln Leu Phe Leu Trp Asp Lys Thr Ser Asn Ile Val Lys
 65                  70                  75                  80

Ile Lys Val Gln Glu Leu Phe Gln Arg Pro Val Leu Thr Ala Ser Ser
                85                  90                  95

Phe Gln Pro Ile Glu Gly Gly Pro Val Ser Leu Lys Cys Glu Thr Arg
            100                 105                 110

Leu Ser Pro Gln Arg Leu Asp Val Gln Leu Gln Phe Cys Phe Phe Arg
        115                 120                 125

Glu Asn Gln Val Leu Gly Ser Gly Trp Ser Ser Pro Glu Leu Gln
    130                 135                 140

Ile Ser Ala Val Trp Ser Glu Asp Thr Gly Ser Tyr Trp Cys Lys Ala
145                 150                 155                 160

Glu Thr Val Thr His Arg Ile Arg Lys Gln Ser Leu Gln Ser Gln Ile
                165                 170                 175

His Val Gln Arg Ile Pro Ile Ser Asn Val Ser Leu Glu Ile Arg Ala
            180                 185                 190

Pro Gly Gly Gln Val Thr Glu Gly Gln Lys Leu Ile Leu Leu Cys Ser
        195                 200                 205

Val Ala Gly Gly Thr Gly Asn Val Thr Phe Ser Trp Tyr Arg Glu Ala
    210                 215                 220

Thr Gly Thr Ser Met Gly Lys Lys Thr Gln Arg Ser Leu Ser Ala Glu
225                 230                 235                 240

Leu Glu Ile Pro Ala Val Lys Glu Ser Asp Ala Gly Lys Tyr Tyr Cys
                245                 250                 255

Arg Ala Asp Asn Gly His Val Pro Ile Gln Ser Lys Val Val Asn Ile
            260                 265                 270

Pro Val Arg Ile Pro Val Ser Arg Pro Val Leu Thr Leu Arg Ser Pro
        275                 280                 285

Gly Ala Gln Ala Ala Val Gly Asp Leu Leu Glu Leu His Cys Glu Ala
    290                 295                 300

Leu Arg Gly Ser Pro Pro Ile Leu Tyr Gln Phe Tyr His Glu Asp Val
305                 310                 315                 320

Thr Leu Gly Asn Ser Ser Ala Pro Ser Gly Gly Ala Ser Phe Asn
                325                 330                 335

Leu Ser Leu Thr Ala Glu His Ser Gly Asn Tyr Ser Cys Glu Ala Asn
            340                 345                 350

Asn Gly Leu Gly Ala Gln Cys Ser Glu Ala Val Pro Val Ser Ile Ser
        355                 360                 365

Gly Pro Asp Gly Tyr Arg Arg Asp Leu Met Thr Ala Gly Val Leu Trp
    370                 375                 380
```

```
Gly Leu Phe Gly Val Leu Gly Phe Thr Gly Val Ala Leu Leu Leu Tyr
385                 390                 395                 400

Ala Leu Phe His Lys Ile Ser Gly Glu Ser Ser Ala Thr Asn Glu Pro
            405                 410                 415

Arg Gly Ala Ser Arg Pro Asn Pro Gln Glu Phe Thr Tyr Ser Ser Pro
        420                 425                 430

Thr Pro Asp Met Glu Glu Leu Gln Pro Val Tyr Val Asn Val Gly Ser
    435                 440                 445

Val Asp Val Asp Val Val Tyr Ser Gln Val Trp Ser Met Gln Gln Pro
    450                 455                 460

Glu Ser Ser Ala Asn Ile Arg Thr Leu Leu Glu Asn Lys Asp Ser Gln
465                 470                 475                 480

Val Ile Tyr Ser Ser Val Lys Lys Ser
                485

<210> SEQ ID NO 5
<211> LENGTH: 140
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 5

His Tyr Ala Arg Ala Arg Arg Lys Pro Gly Gly Leu Ser Ala Thr Gly
1               5                   10                  15

Thr Ser Ser His Ser Pro Ser Glu Cys Gln Glu Pro Ser Ser Ser Arg
            20                  25                  30

Pro Ser Arg Ile Asp Pro Gln Glu Pro Thr His Ser Lys Pro Leu Ala
        35                  40                  45

Pro Met Glu Leu Glu Pro Met Tyr Ser Asn Val Asn Pro Gly Asp Ser
    50                  55                  60

Asn Pro Ile Tyr Ser Gln Ile Trp Ser Ile Gln His Thr Lys Glu Asn
65                  70                  75                  80

Ser Ala Asn Cys Pro Met Met His Gln Glu His Glu Glu Leu Thr Val
                85                  90                  95

Leu Tyr Ser Glu Leu Lys Lys Thr His Pro Asp Asp Ser Ala Gly Glu
            100                 105                 110

Ala Ser Ser Arg Gly Arg Ala His Glu Glu Asp Asp Glu Glu Asn Tyr
        115                 120                 125

Glu Asn Val Pro Arg Val Leu Leu Ala Ser Asp His
    130                 135                 140

<210> SEQ ID NO 6
<211> LENGTH: 717
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 6

Gly Val Ala Pro Lys Ala Val Leu Leu Asn Pro Pro Trp Ser Thr
1               5                   10                  15

Ala Phe Lys Gly Glu Lys Val Ala Leu Ile Cys Ser Ser Ile Ser His
            20                  25                  30

Ser Leu Ala Gln Gly Asp Thr Tyr Trp Tyr His Asp Glu Lys Leu Leu
        35                  40                  45
```

```
Lys Ile Lys His Asp Lys Ile Gln Ile Thr Glu Pro Gly Asn Tyr Gln
    50              55                  60

Cys Lys Thr Arg Gly Ser Ser Leu Ser Asp Ala Val His Val Glu Phe
65                  70                  75                  80

Ser Pro Asp Trp Leu Ile Leu Gln Ala Leu His Pro Val Phe Glu Gly
                85                  90                  95

Asp Asn Val Ile Leu Arg Cys Gln Gly Lys Asp Asn Lys Asn Thr His
            100                 105                 110

Gln Lys Val Tyr Tyr Lys Asp Gly Lys Gln Leu Pro Asn Ser Tyr Asn
        115                 120                 125

Leu Glu Lys Ile Thr Val Asn Ser Val Ser Arg Asp Asn Ser Lys Tyr
    130                 135                 140

His Cys Thr Ala Tyr Arg Lys Phe Tyr Ile Leu Asp Ile Glu Val Thr
145                 150                 155                 160

Ser Lys Pro Leu Asn Ile Gln Val Gln Glu Leu Phe Leu His Pro Val
                165                 170                 175

Leu Arg Ala Ser Ser Ser Thr Pro Ile Glu Gly Ser Pro Met Thr Leu
            180                 185                 190

Thr Cys Glu Thr Gln Leu Ser Pro Gln Arg Pro Asp Val Gln Leu Gln
        195                 200                 205

Phe Ser Leu Phe Arg Asp Ser Gln Thr Leu Gly Leu Gly Trp Ser Arg
    210                 215                 220

Ser Pro Arg Leu Gln Ile Pro Ala Met Trp Thr Glu Asp Ser Gly Ser
225                 230                 235                 240

Tyr Trp Cys Glu Val Glu Thr Val Thr His Ser Ile Lys Lys Arg Ser
                245                 250                 255

Leu Arg Ser Gln Ile Arg Val Gln Arg Val Pro Val Ser Asn Val Asn
            260                 265                 270

Leu Glu Ile Arg Pro Thr Gly Gly Gln Leu Ile Glu Gly Glu Asn Met
        275                 280                 285

Val Leu Ile Cys Ser Val Ala Gln Gly Ser Gly Thr Val Thr Phe Ser
    290                 295                 300

Trp His Lys Glu Gly Arg Val Arg Ser Leu Gly Arg Lys Thr Gln Arg
305                 310                 315                 320

Ser Leu Leu Ala Glu Leu His Val Leu Thr Val Lys Glu Ser Asp Ala
                325                 330                 335

Gly Arg Tyr Tyr Cys Ala Ala Asp Asn Val His Ser Pro Ile Leu Ser
            340                 345                 350

Thr Trp Ile Arg Val Thr Val Arg Ile Pro Val Ser His Pro Val Leu
        355                 360                 365

Thr Phe Arg Ala Pro Arg Ala His Thr Val Val Gly Asp Leu Leu Glu
    370                 375                 380

Leu His Cys Glu Ser Leu Arg Gly Ser Pro Pro Ile Leu Tyr Arg Phe
385                 390                 395                 400

Tyr His Glu Asp Val Thr Leu Gly Asn Ser Ser Ala Pro Ser Gly Gly
                405                 410                 415

Gly Ala Ser Phe Asn Leu Ser Leu Thr Ala Glu His Ser Gly Asn Tyr
            420                 425                 430

Ser Cys Asp Ala Asp Asn Gly Leu Gly Ala Gln His Ser His Gly Val
        435                 440                 445

Ser Leu Arg Val Thr Val Pro Val Ser Arg Pro Val Leu Thr Leu Arg
    450                 455                 460

Ala Pro Gly Ala Gln Ala Val Val Gly Asp Leu Leu Glu Leu His Cys
```

```
                465                 470                 475                 480
Glu Ser Leu Arg Gly Ser Phe Pro Ile Leu Tyr Trp Phe Tyr His Glu
                    485                 490                 495

Asp Asp Thr Leu Gly Asn Ile Ser Ala His Ser Gly Gly Ala Ser
                500                 505                 510

Phe Asn Leu Ser Leu Thr Thr Glu His Ser Gly Asn Tyr Ser Cys Glu
                515                 520                 525

Ala Asp Asn Gly Leu Gly Ala Gln His Ser Lys Val Val Thr Leu Asn
            530                 535                 540

Val Thr Gly Thr Ser Arg Asn Arg Thr Gly Leu Thr Ala Ala Gly Ile
545                 550                 555                 560

Thr Gly Leu Val Leu Ser Ile Leu Val Leu Ala Ala Ala Ala Leu
                565                 570                 575

Leu His Tyr Ala Arg Ala Arg Arg Lys Pro Gly Gly Leu Ser Ala Thr
                580                 585                 590

Gly Thr Ser Ser His Ser Pro Ser Glu Cys Gln Glu Pro Ser Ser Ser
                595                 600                 605

Arg Pro Ser Arg Ile Asp Pro Gln Glu Pro Thr His Ser Lys Pro Leu
            610                 615                 620

Ala Pro Met Glu Leu Glu Pro Met Tyr Ser Asn Val Asn Pro Gly Asp
625                 630                 635                 640

Ser Asn Pro Ile Tyr Ser Gln Ile Trp Ser Ile Gln His Thr Lys Glu
                645                 650                 655

Asn Ser Ala Asn Cys Pro Met Met His Gln Glu His Glu Glu Leu Thr
                660                 665                 670

Val Leu Tyr Ser Glu Leu Lys Lys Thr His Pro Asp Asp Ser Ala Gly
                675                 680                 685

Glu Ala Ser Ser Arg Gly Arg Ala His Glu Glu Asp Asp Glu Glu Asn
            690                 695                 700

Tyr Glu Asn Val Pro Arg Val Leu Leu Ala Ser Asp His
705                 710                 715

<210> SEQ ID NO 7
<211> LENGTH: 300
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 7
aaaagaaaaa taggaagacg ttcagccagg gatccactca ggagccttcc cagccctcta      60
ccccaagagt tcacctacct caactcacct accccagggc agctacagcc tatatatgaa     120
aatgtgaatg ttgtaagtgg ggatgaggtt tattcactgg cgtactataa ccagccggag     180
caggaatcag tagcagcaga aaccctgggg acacatatgg aggacaaggt ttccttagac     240
atctattcca ggctgaggaa agcaaacatt acagatgtgg actatgaaga tgctatgtaa     300

<210> SEQ ID NO 8
<211> LENGTH: 2038
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 8
```

```
ctcgactctg aggtgcattc ttttttttgat gagaggcatc tctaggtacc atccctgacc    60
tggtcctcat gctgccgagg ctgttgctgt tgatctgtgc tccactctgt gaacctgccg   120
agctgttttt gatagccagc ccctcccatc ccacagaggg gagcccagtg accctgacgt   180
gtaagatgcc ctttctacag agttcagatg cccagttcca gttctgcttt ttcagagaca   240
cccgggcctt gggcccaggc tggagcagct cccccaagct ccagatcgct gccatgtgga   300
aagaagacac agggtcatac tggtgcgagg cacagacaat ggcgtccaaa gtcttgagga   360
gcaggagatc ccagataaat gtgcacaggg tccctgtcgc tgatgtgagc ttggagactc   420
agcccccagg aggacaggtg atggaggag acaggctggt cctcatctgc tcagttgcta   480
tgggcacagg agacatcacc ttcctttggt acaaggggc tgtaggttta aaccttcagt   540
caaagaccca gcgttcactg acagcagagt atgagattcc ttcagtgagg gagagtgatg   600
ctgagcaata ttactgtgta gctgaaaatg ctatggtcc cagccccagt gggctggtga   660
gcatcactgt cagaatcccg gtgtctcgcc caatcctcat gctcagggct cccagggccc   720
aggctgcagt ggaggatgtg ctggagcttc actgtgaggc cctgagaggc tctcctccaa   780
tcctgtactg gttttatcac gaggatatca ccctggggag caggtcggcc ccctctggag   840
gaggagcctc cttcaacctt tccctgactg aagaacattc tggaaactac tcctgtgagg   900
ccaacaatgg cctgggggcc cagcgcagtg aggcggtgac actcaacttc acagtgccta   960
ctggggccag aagcaatcat cttacctcag gagtcattga ggggctgctc agcaccttg  1020
gtccagccac cgtggcctta ttattttgct acggcctcaa aagaaaaata ggaagacgtt  1080
cagccaggga tccactcagg agccttccca gccctctacc ccaagagttc acctacctca  1140
actcacctac cccagggcag ctacagccta tatgaaaaa tgtgaatgtt gtaagtgggg  1200
atgaggttta ttcactggcg tactataacc agccggagca ggaatcagta gcagcagaaa  1260
ccctggggac acatatggag acaaggtttt ccttagacat ctattccagg ctgaggaaag  1320
caaacattac agatgtggac tatgaagatg ctatgtaagg ttatggaaga ttctgctctt  1380
tgaaaaccat ccatgacccc aagcctcagg cctgatatgt tcttcagaga tcctggggca  1440
ttagctttcc agtataccct ttctggatgc cattctccat ggcactattc cttcatctac  1500
tgtgaagtga agttggcgca gccctgaaga aactacctag gagaactaat agacacagga  1560
gtgacaggga ctttgttatc agaaccagat tcctgccggc tcctttgaaa acaggtcata  1620
ttgtgctctt ctgttttacaa gaggaaacaa gatggaataa aagaaattgg gatcttgggt  1680
tggagggaca gtgaagctta gagcacatga actcaaggtt agtgactctg caggacttca  1740
cagagagagc tgtgcccatc attcagtcca agtgctttct ctgcccagac agcacagaac  1800
tccagccccg ctacttacat ggatcatcga gtttccacct aaaatatgat tctatttatt  1860
ttgagtcact gttaccaaat tagaactaaa acaaagttac ataaaaagtt attgtgactc  1920
cacttaattt tagtgacgta ttttttgtata taggccaa cctataccac atccaaaatt  1980
atgtatctat tacagcccct agaagcttta taaatacagt gtgtcttctt ttattcac    2038
```

<210> SEQ ID NO 9
<211> LENGTH: 261
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 9

-continued

| | |
|---|---|
| cacaagatat caggagaaag ttctgccact aatgaaccca gagggcttc caggccaaat | 60 |
| cctcaagagt tcacctattc aagcccaacc ccagacatgg aggagctgca gccagtgtat | 120 |
| gtcaatgtgg gctctgtaga tgtggatgtg gtttattctc aggtctggag catgcagcag | 180 |
| ccagaaagct cagcaaacat caggacactt ctggagaaca aggactccca agtcatctac | 240 |
| tcttctgtga agaaatcata a | 261 |

<210> SEQ ID NO 10
<211> LENGTH: 2573
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 10

| | |
|---|---|
| ggtgaccaag agtacatctc ttttcaaata gctggattag gtcctcatgc tgctgtggtc | 60 |
| attgctggtc atctttgatg cagtcactga acaggcagat tcgctgaccc ttgtggcgcc | 120 |
| ctcttctgtc ttcgaaggag acagcatcgt tctgaaatgc cagggagaac agaactggaa | 180 |
| aattcagaag atggcttacc ataaggataa caaagagtta tctgttttca aaaaattctc | 240 |
| agatttcctt atccaaagtg cagttttaag tgacagtggt aactatttct gtagtaccaa | 300 |
| aggacaactc tttctctggg ataaaacttc aaatatagta aagataaaag tccaagagct | 360 |
| ctttcaacgt cctgtgctga ctgccagctc cttccagccc atcgaagggg gtccagtgag | 420 |
| cctgaaatgt gagacccggc tctctccaca gaggttggag gttcaactcc agttctgctt | 480 |
| cttcagagaa aaccaggtcc tggggtcagg ctggagcagc tctccggagc tccagatttc | 540 |
| tgccgtgtgg agtgaagaca cagggtctta ctggtgcaag gcagaaacgg tgactcacag | 600 |
| gatcagaaaa cagagcctcc aatcccagat tcacgtgcag agaatcccca tctctaatgt | 660 |
| aagcttggag atccgggccc ccgggggaca ggtgactgaa ggacaaaaac tgatcctgct | 720 |
| ctgctcagtg gctggggta caggaaatgt cacattctcc tggtacagag aggccacagg | 780 |
| aaccagtatg ggaaagaaaa cccagcgttc cctgtcagca gagctggaga tcccagctgt | 840 |
| gaaagagagt gatgccggca atattactg tagagctgac aacggccatg tgcctatcca | 900 |
| gagcaaggtg tgaatatcc ctgtgagaat tccagtgtct cgccctgtcc tcaccctcag | 960 |
| gtctcctggg gcccaggctg cagtggggga cctgctggag cttcactgtg aggccctgag | 1020 |
| aggctctccc ccaatcttgt accaattta tcatggaggat gtcacccttg gaacagctc | 1080 |
| ggcccctct ggaggagggg cctccttcaa cctctctttg actgcagaac attctggaaa | 1140 |
| ctactcctgt gaggccaaca acggcctggg ggcccagtgc agtgaggcag tgccagtctc | 1200 |
| catctcagga cctgatggct atagaagaga cctcatgaca gctggagttc tctggggact | 1260 |
| gtttggtgtc cttggtttca ctggtgttgc tttgctgttg tatgccttgt tccacaagat | 1320 |
| atcaggagaa agttctgcca ctaatgaacc cagagggct tccaggccaa atcctcaaga | 1380 |
| gttcacctat tcaagcccaa ccccagacat ggaggagctg cagccagtgt atgtcaatgt | 1440 |
| gggctctgta gatgtggatg tggtttattc tcaggtctgg agcatgcagc agccagaaag | 1500 |
| ctcagcaaac atcaggacac ttctggaaga caaggactcc caagtcatct actcttctgt | 1560 |
| gaagaaatca taacacttgg aggaatcaga agggaagatc aacagcaagg atggggcatc | 1620 |
| attaagactt gctataaaac cttatgaaaa tgcttgaggc ttatcacctg ccacagccag | 1680 |
| aacgtgcctc aggaggcacc tcctgtcatt tttgtcctga tgatgtttct tctccaatat | 1740 |

-continued

```
cttcttttac ctatcaatat tcattgaact gctgctacat ccagacactg tgcaaataaa    1800
ttatttctgc taccttctct taagcaatca gtgtgtaaag atttgaggga agaatgaata    1860
agagatacaa ggtctcacct tcatctactg tgaagtgatg agaacaggac ttgatagtgg    1920
tgtattaact tatttatgtg ctgctggata cagtttgcta atattttgtt gagaatttt     1980 gcaaatatgt tcattgggaa tattggcctg aaattttctt ttccactgtg tctctgccag    2040
aatgtttgta tcaggctgat gctggcttca tagaatgagt taggcaggag cccttcctcc    2100
ttgatttttt ggcatagttt cagcaggatt ggtaccagtt attctttctg catcttgtag    2160
aattcagcta tgaatccatc tggtctaggg cttttgtgtt ggttggtaag ttttttatta    2220
ctaattcaac ttcagcgctt gatattggtc taggaggggt ttctgtctct tcctggttca    2280
atcttgggag attgtgtgtt tccaggaatt tagccgtttc ctccagattt tcttctttat    2340
gtgcatcgac ttgagtgtaa acataactta tatgcactgg gaaaccaaaa aatctgtgtg    2400
acttgcttta ttgcagcatt tgttttattt tggtagtctg gaactgaacc tgcaatatca    2460
ccaaagtatg catatagttg caaaaatgtg attttttgaca tagtaaatat gagtatttgc    2520
aataaactat gatattactt ttgtaagtat atagaataaa atgtaaataa tct            2573

<210> SEQ ID NO 11
<211> LENGTH: 423
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 11
cattacgcca gggcccgaag gaaaccagga ggactttctg ccactggaac atctagtcac      60
agtcctagcg agtgtcagga gccttcctcg tccaggcctt ccaggataga ccctcaagag    120
cccactcact ctaaaccact agccccaatg gagctggagc caatgtacag caatgtaaat    180
cctggagata gcaacccgat ttattcccag atctggagca tccagcatac aaaagaaaac    240
tcagctaatt gtccaatgat gcatcaagag catgaggaac ttacagtcct ctattcagaa    300
ctgaagaaga cacacccaga cgactctgca ggggaggcta gcagcagagg cagggcccat    360
gaagaagatg atgaagaaaa ctatgagaat gtaccacgtg tattactggc ctcagaccac    420
tag                                                                  423

<210> SEQ ID NO 12
<211> LENGTH: 2416
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 12
gtctcatctg agtagcagct tcctgccctc cttcttggag ataagtcggg cttttggtga      60
gacagacttt cccaaccctc tgcccggccg gtgcccatgc ttctgtggct gctgctgctg    120
atcctgactc ctggaagaga acaatcaggg gtggccccaa agctgtact tctcctcaat     180 cctccatggt ccacagcctt caaggagaa aaagtggctc tcatatgcag cagcatatca    240
cattccctag cccagggaga cacatattgg tatcacgatg agaagttgtt gaaaataaaa    300
catgacaaga tccaaattac agagcctgga aattaccaat gtaagacccg aggatcctcc    360
ctcagtgatg ccgtgcatgt ggaattttca cccgactggc tgatcctgca ggctttacat    420
```

-continued

```
cctgtctttg aaggagacaa tgtcattctg agatgtcagg ggaaagacaa caaaaacact      480
catcaaaagg tttactacaa ggatggaaaa cagcttccta atagttataa tttagagaag      540
atcacagtga attcagtctc cagggataat agcaaatatc attgtactgc ttataggaag      600
ttttacatac ttgacattga agtaacttca aaacccctaa atatccaagt tcaagagctg      660 tttctcatc ctgtgctgag agccagctct tccacgccca tagaggggag tcccatgacc       720
ctgacctgtg agacccagct ctctccacag aggccagatg tccagctgca attctccctc      780
ttcagagata gccagaccct cggattgggc tggagcaggt cccccagact ccagatccct      840
gccatgtgga ctgaagactc agggtcttac tggtgtgagg tggagacagt gactcacagc      900
atcaaaaaaa ggagcctgag atctcagata cgtgtacaga gagtccctgt gtctaatgtg      960
aatctagaga tccggcccac cggagggcag ctgattgaag agaaaatat ggtccttatt      1020 tgctcagtag cccagggttc agggactgtc acattctcct ggcacaaaga aggaagagta     1080
agaagcctgg gtagaaagac ccagcgttcc ctgttggcag agctgcatgt tctcaccgtg      1140
aaggagagtg atgcagggag atactactgt gcagctgata cgttcacag ccccatcctc       1200 agcacgtgga ttcgagtcac cgtgagaatt ccggtatctc accctgtcct caccttcagg      1260
gctcccaggg cccacactgt ggtggggac ctgctggagc ttcactgtga gtccctgaga       1320
ggctctcccc cgatcctgta ccgattttat catgaggacg tcaccctggg gaacagctca      1380
gccccctctg gaggaggagc ctccttcaac ctctctctga ctgcagaaca ttctggaaac      1440
tactcctgtg atgcagacaa tggcctgggg gcccagcaca gtcatggagt gagtctcagg      1500
gtcacagttc cggtgtctcg ccccgtcctc accctcaggg ctcccggggc ccaggctgtg      1560 gtggggggacc tgctggagct tcactgtgag tccctgagag gctccttccc gatcctgtac      1620
tggttttatc acgaggatga caccttgggg aacatctcgg cccactctgg aggaggggca     1680
tccttcaacc tctctctgac tacagaacat tctggaaact actcatgtga ggctgacaat      1740
ggcctggggg cccagcacag taaagtggtg acactcaatg ttacaggaac ttccaggaac      1800
agaacaggcc ttaccgctgc gggaatcacg gggctggtgc tcagcatcct cgtccttgct      1860
gctgctgctg ctctgctgca ttacgccagg gcccgaagga aaccaggagg actttctgcc      1920
actggaacat ctagtcacag tcctagcgag tgtcaggagc cttcctcgtc caggccttcc      1980
aggatagacc ctcaagagcc cactcactct aaaccactag cccaatgga gctggagcca     2040 atgtacagca atgcaaatcc tggagatagc aacccgattt attcccagat ctggagcatc      2100
cagcatacaa agaaaactc agctaattgt ccaatgatgc atcaagagca tgaggaactt       2160
acagtcctct attcagaact gaagaagaca cacccagacg actctgcagg ggaggctagc      2220
agcagaggca gggcccatga agaagatgat gaagaaaact atgagaatgt accacgtgta      2280
ttactggcct cagaccacta gccccttacc cagagtggcc cacaggaaac agcctgcacc      2340 atttttttt ctgttctctc caaccacaca tcatccatct ctccagactc tgcctcctac       2400
gaggctgggc tgcagg                                                     2416
```

<210> SEQ ID NO 13
<211> LENGTH: 873
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 13

```
gagctgtttt tgatagccag cccctcccat cccacagagg ggagcccagt gaccctgacg      60
tgtaagatgc cctttctaca gagttcagat gcccagttcc agttctgctt tttcagagac     120
acccgggcct tgggcccagg ctggagcagc tcccccaagc tccagatcgc tgccatgtgg     180
aaagaagaca cagggtcata ctggtgcgag gcacagacaa tggcgtccaa agtcttgagg     240
agcaggagat cccagataaa tgtgcacagg gtccctgtcg ctgatgtgag cttggagact     300
cagcccccag gaggacaggt gatggaggga gacaggctgg tcctcatctg ctcagttgct     360
atgggcacag agacatcac cttcctttgg tacaaagggg ctgtaggttt aaaccttcag      420
tcaaagaccc agcgttcact gacagcagag tatgagattc cttcagtgag ggagagtgat     480
gctgagcaat attactgtgt agctgaaaat ggctatggtc ccagcccag tgggctggtg       540 agcatcactg tcagaatccc ggtgtctcgc ccaatcctca tgctcagggc tcccagggcc     600
caggctgcag tggaggatgt gctggagctt cactgtgagg ccctgagagg ctctcctcca     660
atcctgtact ggttttatca cgaggatatc accctgggga gcaggtcggc cccctctgga     720
ggaggagcct ccttcaacct ttccctgact gaagaacatt ctggaaacta ctcctgtgag     780
gccaacaatg gcctgggggc ccagcgcagt gaggcggtga cactcaactt cacagtgcct     840
actggggcca gaagcaatca tcttacctca gga                                  873

<210> SEQ ID NO 14
<211> LENGTH: 1137
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 14
acccttgtgg cgccctcttc tgtcttcgaa ggagacagca tcgttctgaa atgccaggga    60
gaacagaact ggaaaattca agatggct taccataagg ataacaaaga gttatctgtt      120
ttcaaaaaat tctcagattt ccttatccaa agtgcagttt aagtgacag tggtaactat      180 ttctgtagta ccaaaggaca actctttctc tgggataaaa cttcaaatat agtaaagata    240
aaagtccaag agctctttca acgtcctgtg ctgactgcca gctccttcca gcccatcgaa    300
gggggtccag tgagcctgaa atgtgagacc cggctctctc cacagaggtt ggatgttcaa    360
ctccagttct gcttcttcag agaaaaccag gtcctgggt caggctggag cagctctccg    420
gagctccaga tttctgccgt gtggagtgaa gacacagggc cttactggtg caaggcagaa    480
acggtgactc acaggatcag aaaacagagc ctccaatccc agattcacgt gcagagaatc    540
cccatctcta atgtaagctt ggagatccgg gccccggggg gacaggtgac tgaaggacaa    600
aaactgatcc tgctctgctc agtggctggg ggtacaggaa atgtcacatt ctcctggtac    660
agagaggcca caggaaccag tatgggaaag aaaacccagc gttccctgtc agcagagctg    720
gagatcccag ctgtgaaaga gagtgatgcc ggcaaatatt actgtagagc tgacaacggc    780
catgtgccta tccagagcaa ggtggtgaat atccctgtga aattccagt gtctcgccct     840 gtcctcaccc tcaggtctcc tgggggccag gctgcagtgg gggacctgct ggagcttcac    900
tgtgaggccc tgagggctc tccccaatc ttgtaccaat tttatcatga ggatgtcacc      960
cttgggaaca gctcggcccc ctctggagga ggggcctcct tcaacctctc tttgactgca    1020
gaacattctg gaaactactc ctgtgaggcc aacaacggcc tggggcccca gtgcagtgag   1080
gcagtgccag tctccatctc aggacctgat ggctatagaa gagacctcat gacagct       1137
```

<210> SEQ ID NO 15
<211> LENGTH: 1659
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 15

```
gtggccccaa aagctgtact tctcctcaat cctccatggt ccacagcctt caaaggagaa      60
aaagtggctc tcatatgcag cagcatatca cattccctag cccagggaga cacatattgg     120
tatcacgatg agaagttgtt gaaaataaaa catgacaaga tccaaattac agagcctgga     180
aattaccaat gtaagacccg aggatcctcc ctcagtgatg ccgtgcatgt ggaattttca     240
cccgactggc tgatcctgca ggctttacat cctgtctttg aaggagacaa tgtcattctg     300
agatgtcagg ggaaagacaa caaaaacact catcaaaagg tttactacaa ggatggaaaa     360
cagcttccta atagttataa tttagagaag atcacagtga attcagtctc cagggataat     420
agcaaatatc attgtactgc ttataggaag ttttacatac ttgacattga agtaacttca     480
aaaccctaa atatccaagt tcaagagctg tttctacatc ctgtgctgag agccagctct     540
tccacgccca tagaggggag tcccatgacc ctgacctgtg agaccagct ctctccacag     600
aggccagatg tccagctgca attctccctc ttcagagata gccagaccct cggattgggc     660
tggagcaggt cccccagact ccagatccct gccatgtgga ctgaagactc agggtcttac     720
tggtgtgagg tggagacagt gactcacagc atcaaaaaaa ggagcctgag atctcagata     780
cgtgtacaga gagtccctgt gtctaatgtg aatctagaga tccggcccac cggagggcag     840
ctgattgaag gagaaaatat ggtccttatt tgctcagtag cccagggttc agggactgtc     900
acattctcct ggcacaaaga aggaagagta agaagcctgg gtagaaagac ccagcgttcc     960
ctgttggcag agctgcatgt tctcaccgtg aaggagagtg atgcagggag atactactgt    1020
gcagctgata cgttcacag ccccatcctc agcacgtgga ttcgagtcac cgtgagaatt    1080
ccggtatctc accctgtcct caccttcagg gctcccaggg cccacactgt ggtggggggac    1140
ctgctggagc ttcactgtga gtccctgaga ggctctcccc cgatcctgta ccgatttat    1200
catgaggacg tcaccctggg gaacagctca gcccctctg gaggaggagc ctccttcaac    1260
ctctctctga ctgcagaaca ttctggaaac tactcctgtg atgcagacaa tggcctgggg    1320
gcccagcaca gtcatggagt gagtctcagg gtcacagttc cggtgtctcg ccccgtcctc    1380
accctcaggg ctcccgggc ccaggctgtg gtgggggacc tgctggagct tcactgtgag    1440
tccctgagag gctccttccc gatcctgtac tggtttatc acgaggatga cccttgggg    1500
aacatctcgg cccactctgg aggaggggca tccttcaacc tctctctgac tacagaacat    1560
tctggaaact actcatgtga ggctgacaat ggcctggggg cccagcacag taaagtggtg    1620
acactcaatg ttacaggaac ttccaggaac agaacaggc                         1659
```

<210> SEQ ID NO 16
<211> LENGTH: 423
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 16

```
cattacgcca gggcccgaag gaaaccagga ggactttctg ccactggaac atctagtcac    60
agtcctagcg agtgtcagga gccttcctcg tccaggcctt ccaggataga ccctcaagag   120
cccactcact ctaaaccact agccccaatg gagctggagc caatgtacag caatgcaaat   180
cctggagata gcaacccgat ttattcccag atctggagca tccagcatac aaaagaaaac   240
tcagctaatt gtccaatgat gcatcaagag catgaggaac ttacagtcct ctattcagaa   300
ctgaagaaga cacacccaga cgactctgca ggggaggcta gcagcagagg cagggcccat   360
gaagaagatg atgaagaaaa ctatgagaat gtaccacgtg tattactggc ctcagaccac   420
tag                                                                 423

<210> SEQ ID NO 17
<211> LENGTH: 2151
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 17
gtggccccaa aagctgtact tctcctcaat cctccatggt ccacagcctt caaaggagaa    60
aaagtggctc tcatatgcag cagcatatca cattccctag cccagggaga cacatattgg   120
tatcacgatg agaagttgtt gaaaataaaa catgacaaga tccaaattac agagcctgga   180
aattaccaat gtaagacccg aggatcctcc ctcagtgatg ccgtgcatgt ggaattttca   240
cccgactggc tgatcctgca ggctttacat cctgtctttg aaggagacaa tgtcattctg   300
agatgtcagg ggaaagacaa caaaaacact catcaaaagg tttactacaa ggatggaaaa   360
cagcttccta atagttataa tttagagaag atcacagtga attcagtctc cagggataat   420
agcaaatatc attgtactgc ttataggaag ttttacatac ttgacattga agtaacttca   480 aaaccccctaa atatccaagt tcaagagctg tttctcacatc ctgtgctgag agccagctct   540
tccacgccca tagaggggag tcccatgacc ctgacctgtg agacccagct ctctccacag   600
aggccagatg tccagctgca attctccctc ttcagagata gccagaccct cggattgggc   660
tggagcaggt cccccagact ccagatccct gccatgtgga ctgaagactc agggtcttac   720
tggtgtgagg tggagacagt gactcacagc atcaaaaaaa ggagcctgag atctcagata   780
cgtgtacaga gagtccctgt gtctaatgtg aatctagaga tccggcccac cggagggcag   840
ctgattgaag agaaaatat ggtccttatt tgctcagtag cccagggttc agggactgtc   900
acattctcct ggcacaaaga aggaagagta agaagcctgg gtagaaagac ccagcgttcc   960
ctgttggcag agctgcatgt tctcaccgtg aaggagagtg atgcagggag atactactgt  1020
gcagctgata cgttcacag ccccatcctc agcacgtgga ttcgagtcac cgtgagaatt  1080
ccggtatctc accctgtcct caccttcagg gctcccaggg cccacactgt ggtggggac  1140 ctgctggagc ttcactgtga gtccctgaga ggctctcccc cgatcctgta ccgattttat  1200
catgaggacg tcaccctggg gaacagctca gcccccctctg gaggaggagc ctccttcaac  1260
ctctctctga ctgcagaaca ttctggaaac tactcctgtg atgcagacaa tggcctgggg  1320
gcccagcaca gtcatggagt gagtctcagg gtcacagttc cggtgtctcg ccccgtcctc  1380
accctcaggg ctcccggggc ccaggctgtg gtggggggacc tgctggagct tcactgtgag  1440
tccctgagag gctccttccc gatcctgtac tggttttatc acgaggatga cccttgggg  1500 aacatctcgg cccactctgg aggagggca tccttcaacc tctctctgac tacagaacat  1560
```

```
tctgaaaact actcatgtga ggctgacaat ggcctggggg cccagcacag taaagtggtg    1620
acactcaatg ttacaggaac ttccaggaac agaacaggcc ttaccgctgc gggaatcacg    1680
gggctggtgc tcagcatcct cgtccttgct gctgctgctg ctctgctgca ttacgccagg    1740
gcccgaagga aaccaggagg actttctgcc actggaacat ctagtcacag tcctagcgag    1800
tgtcaggagc cttcctcgtc caggccttcc aggatagacc ctcaagagcc cactcactct    1860
aaaccactag ccccaatgga gctggagcca atgtacagca atgcaaatcc tggagatagc    1920
aacccgattt attcccagat ctggagcatc cagcatacaa agaaaactc agctaattgt    1980 ccaatgatgc atcaagagca tgaggaactt acagtcctct attcagaact gaagaagaca    2040
cacccagacg actctgcagg ggaggctagc agcagaggca gggcccatga agaagatgat    2100
gaagaaaact atgagaatgt accacgtgta ttactggcct cagaccacta g             2151

<210> SEQ ID NO 18
<211> LENGTH: 315
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 18
agatcctgga gaaaagctgg gccccttcca tcccagatac cacccacagc tccaggtgga     60
gagcagtgcc cactatatgc caacgtgcat caccagaaag ggaaagatga aggtgttgtc    120
tactctgtgg tgcatagaac ctcaaagagg agtgaagcca gtctgctga gttcaccgtg    180 gggagaaagg acagttctat catctgtgcg gaggtgagat gcctgcagcc cagtgaggtt    240
tcatccacgg aggtgaatat gagaagcagg actctccaag aacccttag cgactgtgag    300 gaggttctct gctag                                                    315

<210> SEQ ID NO 19
<211> LENGTH: 870
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 19
actgtctggc tgtacctcca agcctggcca aaccctgtgt ttgaaggaga tgccctgact     60
ctgcgatgtc aggatggaa gaatacacca ctgtctcagg tgaagttcta cagagatgga    120
aaattccttc atttctctaa ggaaaaccag actctgtcca tgggagcagc aacagtgcag    180
agccgtggcc agtacagctg ctctgggcag gtgatgtata ttccacagac attcacacaa    240
acttcagaga ctgccatggt tcaagtccaa gagctgtttc cacctcctgt gctgagtgcc    300
atcccctctc ctgagccccg agagggtagc ctggtgaccc tgagatgtca gacaaagctg    360 cacccccctga ggtcagcctt gaggctcctt ttctccttcc acaaggacgg ccacaccttg    420
caggacaggg gccctcaccc agaactctgc atccgggag ccaaggaggg agactctggg    480 cttttactggt gtgaggtggc ccctgagggt ggccaggtcc agaagcagag ccccagctg    540 gaggtcagag tgcaggctcc tgtatcccgt cctgtgctca ctctgcacca cgggcctgct    600
gaccctgctg tggggacat ggtgcagctc ctctgtgagg cacagagggg ctcccctccg    660
atcctgtatt ccttctacct tgatgagaag attgtgggga accactcagc tcctgtggt    720 ggaaccacct ccctcctctt cccagtgaag tcagaacagg atgctgggaa ctactcctgc    780
```

```
gaggctgaga acagtgtctc cagagagagg agtgagccca agaagctgtc tctgaagggt      840
tctcaagtct tgttcactcc cgccagcaac                                       870
```

<210> SEQ ID NO 20
<211> LENGTH: 1257
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 20

```
actgtctggc tgtacctcca agcctggcca aaccctgtgt ttgaaggaga tgccctgact       60
ctgcgatgtc agggatggaa gaatacacca ctgtctcagg tgaagttcta cagagatgga     120
aaattccttc atttctctaa ggaaaaccag actctgtcca tgggagcagc aacagtgcag     180
agccgtggcc agtacagctg ctctgggcag gtgatgtata ttccacagac attcacacaa     240
acttcagaga ctgccatggt tcaagtccaa gagctgtttc cacctcctgt gctgagtgcc     300
atcccctctc ctgagccccg agagggtagc ctggtgaccc tgagatgtca gacaaagctg     360
caccccctga ggtcagcctt gaggctcctt ttctccttcc acaaggacgg ccacaccttg     420
caggacaggg gccctcaccc agaactctgc atcccgggag ccaaggaggg agactctggg     480
ctttactggt gtgaggtggc ccctgagggt ggccaggtcc agaagcagag cccccagctg     540
gaggtcagag tgcaggctcc tgtatcccgt cctgtgctca ctctgcacca cgggcctgct     600
gaccctgctg tggggacat ggtgcagctc ctctgtgagg cacagagggg ctcccctccg      660
atcctgtatt ccttctacct tgatgagaag attgtgggga accactcagc tccctgtggt     720
ggaaccacct ccctcctctt cccagtgaag tcagaacagg atgctgggaa ctactcctgc     780
gaggctgaga acagtgtctc cagagagagg agtgagccca agaagctgtc tctgaagggt     840
tctcaagtct tgttcactcc cgccagcaac tggctggttc cttggcttcc tgcgagcctg     900
cttggcctga tggttattgc tgctgcactt ctggtttatg tgagatcctg agaaaagct     960
gggccccttc catcccagat accacccaca gctccaggtg gagagcagtg cccactatat    1020
gccaacgtgc atcaccagaa agggaaagat gaaggtgttg tctactctgt ggtgcataga    1080
acctcaaaga ggagtgaagc caggtctgct gagttcaccg tggggagaaa ggacagttct    1140
atcatctgtg cggaggtgag atgcctgcag cccagtgagg tttcatccac ggaggtgaat    1200
atgagaagca ggactctcca agaacccctt agcgactgtg aggaggttct ctgctag       1257
```

<210> SEQ ID NO 21
<211> LENGTH: 292
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 21

```
Ala Glu Leu Phe Leu Ile Ala Ser Pro Ser His Pro Thr Glu Gly Ser
 1               5                  10                  15

Pro Val Thr Leu Thr Cys Lys Met Pro Phe Leu Gln Ser Ser Asp Ala
            20                  25                  30

Gln Phe Gln Phe Cys Phe Phe Arg Asp Thr Arg Ala Leu Gly Pro Gly
        35                  40                  45

Trp Ser Ser Ser Pro Lys Leu Gln Ile Ala Ala Met Trp Lys Glu Asp
```

```
                50                  55                  60
Thr Gly Ser Tyr Trp Cys Glu Ala Gln Thr Met Ala Ser Lys Val Leu
 65                  70                  75                  80

Arg Ser Arg Arg Ser Gln Ile Asn Val His Arg Val Pro Val Ala Asp
                 85                  90                  95

Val Ser Leu Glu Thr Gln Pro Pro Gly Gly Gln Val Met Glu Gly Asp
                100                 105                 110

Arg Leu Val Leu Ile Cys Ser Val Ala Met Gly Thr Gly Asp Ile Thr
            115                 120                 125

Phe Leu Trp Tyr Lys Gly Ala Val Gly Leu Asn Leu Gln Ser Lys Thr
            130                 135                 140

Gln Arg Ser Leu Thr Ala Glu Tyr Glu Ile Pro Ser Val Arg Glu Ser
145                 150                 155                 160

Asp Ala Glu Gln Tyr Tyr Cys Val Ala Glu Asn Gly Tyr Gly Pro Ser
                165                 170                 175

Pro Ser Gly Leu Val Ser Ile Thr Val Arg Ile Pro Val Ser Arg Pro
            180                 185                 190

Ile Leu Met Leu Arg Ala Pro Arg Ala Gln Ala Ala Val Glu Asp Val
            195                 200                 205

Leu Glu Leu His Cys Glu Ala Leu Arg Gly Ser Pro Pro Ile Leu Tyr
210                 215                 220

Trp Phe Tyr His Glu Asp Ile Thr Leu Gly Ser Arg Ser Ala Pro Ser
225                 230                 235                 240

Gly Gly Gly Ala Ser Phe Asn Leu Ser Leu Thr Glu Glu His Ser Gly
                245                 250                 255

Asn Tyr Ser Cys Glu Ala Asn Asn Gly Leu Gly Ala Gln Arg Ser Glu
                260                 265                 270

Ala Val Thr Leu Asn Phe Thr Val Pro Thr Gly Ala Arg Ser Asn His
            275                 280                 285

Leu Thr Ser Gly
        290

<210> SEQ ID NO 22
<211> LENGTH: 380
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 22

Leu Thr Leu Val Ala Pro Ser Ser Val Phe Glu Gly Asp Ser Ile Val
 1               5                  10                  15

Leu Lys Cys Gln Gly Glu Gln Asn Trp Lys Ile Gln Lys Met Ala Tyr
             20                  25                  30

His Lys Asp Asn Lys Glu Leu Ser Val Phe Lys Phe Ser Asp Phe
             35                  40                  45

Leu Ile Gln Ser Ala Val Leu Ser Asp Ser Gly Asn Tyr Phe Cys Ser
 50                  55                  60

Thr Lys Gly Gln Leu Phe Leu Trp Asp Lys Thr Ser Asn Ile Val Lys
 65                  70                  75                  80

Ile Lys Val Gln Glu Leu Phe Gln Arg Pro Val Leu Thr Ala Ser Ser
             85                  90                  95

Phe Gln Pro Ile Glu Gly Gly Pro Val Ser Leu Lys Cys Glu Thr Arg
            100                 105                 110
```

-continued

Leu Ser Pro Gln Arg Leu Asp Val Gln Leu Gln Phe Cys Phe Phe Arg
        115                 120                 125

Glu Asn Gln Val Leu Gly Ser Gly Trp Ser Ser Pro Glu Leu Gln
    130                 135                 140

Ile Ser Ala Val Trp Ser Glu Asp Thr Gly Ser Tyr Trp Cys Lys Ala
145                 150                 155                 160

Glu Thr Val Thr His Arg Ile Arg Lys Gln Ser Leu Gln Ser Gln Ile
                165                 170                 175

His Val Gln Arg Ile Pro Ile Ser Asn Val Ser Leu Glu Ile Arg Ala
            180                 185                 190

Pro Gly Gly Gln Val Thr Glu Gly Gln Lys Leu Ile Leu Leu Cys Ser
        195                 200                 205

Val Ala Gly Gly Thr Gly Asn Val Thr Phe Ser Trp Tyr Arg Glu Ala
    210                 215                 220

Thr Gly Thr Ser Met Gly Lys Lys Thr Gln Arg Ser Leu Ser Ala Glu
225                 230                 235                 240

Leu Glu Ile Pro Ala Val Lys Glu Ser Asp Ala Gly Lys Tyr Tyr Cys
                245                 250                 255

Arg Ala Asp Asn Gly His Val Pro Ile Gln Ser Lys Val Val Asn Ile
            260                 265                 270

Pro Val Arg Ile Pro Val Ser Arg Pro Val Leu Thr Leu Arg Ser Pro
        275                 280                 285

Gly Ala Gln Ala Ala Val Gly Asp Leu Leu Glu Leu His Cys Glu Ala
    290                 295                 300

Leu Arg Gly Ser Pro Pro Ile Leu Tyr Gln Phe Tyr His Glu Asp Val
305                 310                 315                 320

Thr Leu Gly Asn Ser Ser Ala Pro Ser Gly Gly Gly Ala Ser Phe Asn
                325                 330                 335

Leu Ser Leu Thr Ala Glu His Ser Gly Asn Tyr Ser Cys Glu Ala Asn
            340                 345                 350

Asn Gly Leu Gly Ala Gln Cys Ser Glu Ala Val Pro Val Ser Ile Ser
        355                 360                 365

Gly Pro Asp Gly Tyr Arg Arg Asp Leu Met Thr Ala
    370                 375                 380

<210> SEQ ID NO 23
<211> LENGTH: 140
<212> TYPE: PRT
<213> ORGANISM: Artificial Sequence
<220> FEATURE:
<223> OTHER INFORMATION: Description of Artificial Sequence:/note =
    synthetic construct

<400> SEQUENCE: 23

His Tyr Ala Arg Ala Arg Arg Lys Pro Gly Gly Leu Ser Ala Thr Gly
 1               5                  10                  15

Thr Ser Ser His Ser Pro Ser Glu Cys Gln Glu Pro Ser Ser Ser Arg
                20                  25                  30

Pro Ser Arg Ile Asp Pro Gln Glu Pro Thr His Ser Lys Pro Leu Ala
            35                  40                  45

Pro Met Glu Leu Glu Pro Met Tyr Ser Asn Ala Asn Pro Gly Asp Ser
        50                  55                  60

Asn Pro Ile Tyr Ser Gln Ile Trp Ser Ile Gln His Thr Lys Glu Asn
65                  70                  75                  80

Ser Ala Asn Cys Pro Met Met His Gln Glu His Glu Glu Leu Thr Val
                85                  90                  95

Leu Tyr Ser Glu Leu Lys Lys Thr His Pro Asp Asp Ser Ala Gly Glu
            100                 105                 110

Ala Ser Ser Arg Gly Arg Ala His Glu Glu Asp Glu Glu Asn Tyr
        115                 120                 125

Glu Asn Val Pro Arg Val Leu Leu Ala Ser Asp His
    130                 135                 140

<210> SEQ ID NO 24
<211> LENGTH: 554
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 24

Gly Val Ala Pro Lys Ala Val Leu Leu Asn Pro Pro Trp Ser Thr
1               5                   10                  15

Ala Phe Lys Gly Glu Lys Val Ala Leu Ile Cys Ser Ser Ile Ser His
            20                  25                  30

Ser Leu Ala Gln Gly Asp Thr Tyr Trp Tyr His Asp Glu Lys Leu Leu
        35                  40                  45

Lys Ile Lys His Asp Lys Ile Gln Ile Thr Glu Pro Gly Asn Tyr Gln
    50                  55                  60

Cys Lys Thr Arg Gly Ser Ser Leu Ser Asp Ala Val His Val Glu Phe
65                  70                  75                  80

Ser Pro Asp Trp Leu Ile Leu Gln Ala Leu His Pro Val Phe Glu Gly
                85                  90                  95

Asp Asn Val Ile Leu Arg Cys Gln Gly Lys Asp Asn Lys Asn Thr His
            100                 105                 110

Gln Lys Val Tyr Tyr Lys Asp Gly Lys Gln Leu Pro Asn Ser Tyr Asn
        115                 120                 125

Leu Glu Lys Ile Thr Val Asn Ser Val Ser Arg Asp Asn Ser Lys Tyr
    130                 135                 140

His Cys Thr Ala Tyr Arg Lys Phe Tyr Ile Leu Asp Ile Glu Val Thr
145                 150                 155                 160

Ser Lys Pro Leu Asn Ile Gln Val Gln Glu Leu Phe Leu His Pro Val
                165                 170                 175

Leu Arg Ala Ser Ser Thr Pro Ile Glu Gly Ser Pro Met Thr Leu
            180                 185                 190

Thr Cys Glu Thr Gln Leu Ser Pro Gln Arg Pro Asp Val Gln Leu Gln
        195                 200                 205

Phe Ser Leu Phe Arg Asp Ser Gln Thr Leu Gly Leu Gly Trp Ser Arg
    210                 215                 220

Ser Pro Arg Leu Gln Ile Pro Ala Met Trp Thr Glu Asp Ser Gly Ser
225                 230                 235                 240

Tyr Trp Cys Glu Val Glu Thr Val Thr His Ser Ile Lys Lys Arg Ser
                245                 250                 255

Leu Arg Ser Gln Ile Arg Val Gln Arg Val Pro Val Ser Asn Val Asn
            260                 265                 270

Leu Glu Ile Arg Pro Thr Gly Gly Gln Leu Ile Glu Gly Glu Asn Met
        275                 280                 285

Val Leu Ile Cys Ser Val Ala Gln Gly Ser Gly Thr Val Thr Phe Ser
    290                 295                 300

Trp His Lys Glu Gly Arg Val Arg Ser Leu Gly Arg Lys Thr Gln Arg

```
                305                 310                 315                 320
Ser Leu Leu Ala Glu Leu His Val Leu Thr Val Lys Glu Ser Asp Ala
                325                 330                 335

Gly Arg Tyr Tyr Cys Ala Ala Asp Asn Val His Ser Pro Ile Leu Ser
            340                 345                 350

Thr Trp Ile Arg Val Thr Val Arg Ile Pro Val Ser His Pro Val Leu
        355                 360                 365

Thr Phe Arg Ala Pro Arg Ala His Thr Val Val Gly Asp Leu Leu Glu
    370                 375                 380

Leu His Cys Glu Ser Leu Arg Gly Ser Pro Pro Ile Leu Tyr Arg Phe
385                 390                 395                 400

Tyr His Glu Asp Val Thr Leu Gly Asn Ser Ser Ala Pro Ser Gly Gly
                405                 410                 415

Gly Ala Ser Phe Asn Leu Ser Leu Thr Ala Glu His Ser Gly Asn Tyr
            420                 425                 430

Ser Cys Asp Ala Asp Asn Gly Leu Gly Ala Gln His Ser His Gly Val
        435                 440                 445

Ser Leu Arg Val Thr Val Pro Val Ser Arg Pro Val Leu Thr Leu Arg
    450                 455                 460

Ala Pro Gly Ala Gln Ala Val Val Gly Asp Leu Leu Glu Leu His Cys
465                 470                 475                 480

Glu Ser Leu Arg Gly Ser Phe Pro Ile Leu Tyr Trp Phe Tyr His Glu
                485                 490                 495

Asp Asp Thr Leu Gly Asn Ile Ser Ala His Ser Gly Gly Gly Ala Ser
            500                 505                 510

Phe Asn Leu Ser Leu Thr Thr Glu His Ser Gly Asn Tyr Ser Cys Glu
        515                 520                 525

Ala Asp Asn Gly Leu Gly Ala Gln His Ser Lys Val Val Thr Leu Asn
    530                 535                 540

Val Thr Gly Thr Ser Arg Asn Arg Thr Gly
545                 550

<210> SEQ ID NO 25
<211> LENGTH: 717
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 25

Gly Val Ala Pro Lys Ala Val Leu Leu Leu Asn Pro Pro Trp Ser Thr
1               5                   10                  15

Ala Phe Lys Gly Glu Lys Val Ala Leu Ile Cys Ser Ser Ile Ser His
                20                  25                  30

Ser Leu Ala Gln Gly Asp Thr Tyr Trp Tyr His Asp Glu Lys Leu Leu
            35                  40                  45

Lys Ile Lys His Asp Lys Ile Gln Ile Thr Glu Pro Gly Asn Tyr Gln
        50                  55                  60

Cys Lys Thr Arg Gly Ser Ser Leu Ser Asp Ala Val His Val Glu Phe
65                  70                  75                  80

Ser Pro Asp Trp Leu Ile Leu Gln Ala Leu His Pro Val Phe Glu Gly
                85                  90                  95

Asp Asn Val Ile Leu Arg Cys Gln Gly Lys Asp Asn Lys Asn Thr His
            100                 105                 110
```

```
Gln Lys Val Tyr Tyr Lys Asp Gly Lys Gln Leu Pro Asn Ser Tyr Asn
        115                 120                 125
Leu Glu Lys Ile Thr Val Asn Ser Val Ser Arg Asp Asn Ser Lys Tyr
130                 135                 140
His Cys Thr Ala Tyr Arg Lys Phe Tyr Ile Leu Asp Ile Glu Val Thr
145                 150                 155                 160
Ser Lys Pro Leu Asn Ile Gln Val Gln Glu Leu Phe Leu His Pro Val
                165                 170                 175
Leu Arg Ala Ser Ser Ser Thr Pro Ile Glu Gly Ser Pro Met Thr Leu
                180                 185                 190
Thr Cys Glu Thr Gln Leu Ser Pro Gln Arg Pro Asp Val Gln Leu Gln
            195                 200                 205
Phe Ser Leu Phe Arg Asp Ser Gln Thr Leu Gly Leu Gly Trp Ser Arg
        210                 215                 220
Ser Pro Arg Leu Gln Ile Pro Ala Met Trp Thr Glu Asp Ser Gly Ser
225                 230                 235                 240
Tyr Trp Cys Glu Val Glu Thr Val Thr His Ser Ile Lys Lys Arg Ser
                245                 250                 255
Leu Arg Ser Gln Ile Arg Val Gln Arg Val Pro Val Ser Asn Val Asn
            260                 265                 270
Leu Glu Ile Arg Pro Thr Gly Gly Gln Leu Ile Glu Gly Glu Asn Met
        275                 280                 285
Val Leu Ile Cys Ser Val Ala Gln Gly Ser Gly Thr Val Thr Phe Ser
    290                 295                 300
Trp His Lys Glu Gly Arg Val Arg Ser Leu Gly Arg Lys Thr Gln Arg
305                 310                 315                 320
Ser Leu Leu Ala Glu Leu His Val Leu Thr Val Lys Glu Ser Asp Ala
                325                 330                 335
Gly Arg Tyr Tyr Cys Ala Ala Asp Asn Val His Ser Pro Ile Leu Ser
            340                 345                 350
Thr Trp Ile Arg Val Thr Val Arg Ile Pro Val Ser His Pro Val Leu
        355                 360                 365
Thr Phe Arg Ala Pro Arg Ala His Thr Val Val Gly Asp Leu Leu Glu
    370                 375                 380
Leu His Cys Glu Ser Leu Arg Gly Ser Pro Pro Ile Leu Tyr Arg Phe
385                 390                 395                 400
Tyr His Glu Asp Val Thr Leu Gly Asn Ser Ser Ala Pro Ser Gly Gly
                405                 410                 415
Gly Ala Ser Phe Asn Leu Ser Leu Thr Ala Glu His Ser Gly Asn Tyr
            420                 425                 430
Ser Cys Asp Ala Asp Asn Gly Leu Gly Ala Gln His Ser His Gly Val
        435                 440                 445
Ser Leu Arg Val Thr Val Pro Val Ser Arg Pro Val Leu Thr Leu Arg
    450                 455                 460
Ala Pro Gly Ala Gln Ala Val Val Gly Asp Leu Leu Glu Leu His Cys
465                 470                 475                 480
Glu Ser Leu Arg Gly Ser Phe Pro Ile Leu Tyr Trp Phe Tyr His Glu
                485                 490                 495
Asp Asp Thr Leu Gly Asn Ile Ser Ala His Ser Gly Gly Gly Ala Ser
            500                 505                 510
Phe Asn Leu Ser Leu Thr Thr Glu His Ser Gly Asn Tyr Ser Cys Glu
        515                 520                 525
Ala Asp Asn Gly Leu Gly Ala Gln His Ser Lys Val Val Thr Leu Asn
```

-continued

```
                    530                 535                 540
Val Thr Gly Thr Ser Arg Asn Arg Thr Gly Leu Thr Ala Ala Gly Ile
545                 550                 555                 560

Thr Gly Leu Val Leu Ser Ile Leu Val Leu Ala Ala Ala Ala Leu
                565                 570                 575

Leu His Tyr Ala Arg Ala Arg Lys Pro Gly Gly Leu Ser Ala Thr
                580                 585                 590

Gly Thr Ser Ser His Ser Pro Ser Glu Cys Gln Pro Ser Ser Ser
                595                 600                 605

Arg Pro Ser Arg Ile Asp Pro Gln Glu Pro Thr His Ser Lys Pro Leu
                610                 615                 620

Ala Pro Met Glu Leu Glu Pro Met Tyr Ser Asn Ala Asn Pro Gly Asp
625                 630                 635                 640

Ser Asn Pro Ile Tyr Ser Gln Ile Trp Ser Ile Gln His Thr Lys Glu
                645                 650                 655

Asn Ser Ala Asn Cys Pro Met Met His Gln Glu His Glu Glu Leu Thr
                660                 665                 670

Val Leu Tyr Ser Glu Leu Lys Lys Thr His Pro Asp Asp Ser Ala Gly
                675                 680                 685

Glu Ala Ser Ser Arg Gly Arg Ala His Glu Glu Asp Asp Glu Glu Asn
                690                 695                 700

Tyr Glu Asn Val Pro Arg Val Leu Leu Ala Ser Asp His
705                 710                 715

<210> SEQ ID NO 26
<211> LENGTH: 104
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 26

Arg Ser Trp Arg Lys Ala Gly Pro Leu Pro Ser Gln Ile Pro Pro Thr
1               5                   10                  15

Ala Pro Gly Gly Glu Gln Cys Pro Leu Tyr Ala Asn Val His His Gln
                20                  25                  30

Lys Gly Lys Asp Glu Gly Val Val Tyr Ser Val Val His Arg Thr Ser
            35                  40                  45

Lys Arg Ser Glu Ala Arg Ser Ala Glu Phe Thr Val Gly Arg Lys Asp
        50                  55                  60

Ser Ser Ile Ile Cys Ala Glu Val Arg Cys Leu Gln Pro Ser Glu Val
65                  70                  75                  80

Ser Ser Thr Glu Val Asn Met Arg Ser Arg Thr Leu Gln Glu Pro Leu
                85                  90                  95

Ser Asp Cys Glu Glu Val Leu Cys
            100

<210> SEQ ID NO 27
<211> LENGTH: 291
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 27

Lys Thr Val Trp Leu Tyr Leu Gln Ala Trp Pro Asn Pro Val Phe Glu
```

```
                1               5                  10                  15
            Gly Asp Ala Leu Thr Leu Arg Cys Gln Gly Trp Lys Asn Thr Pro Leu
                        20                  25                  30

Ser Gln Val Lys Phe Tyr Arg Asp Gly Lys Phe Leu His Phe Ser Lys
                        35                  40                  45

Glu Asn Gln Thr Leu Ser Met Gly Ala Ala Thr Val Gln Ser Arg Gly
                    50                  55                  60

Gln Tyr Ser Cys Ser Gly Gln Val Met Tyr Ile Pro Gln Thr Phe Thr
             65                  70                  75                  80

Gln Thr Ser Glu Thr Ala Met Val Gln Val Gln Glu Leu Phe Pro Pro
                                85                  90                  95

Pro Val Leu Ser Ala Ile Pro Ser Pro Glu Pro Arg Glu Gly Ser Leu
                            100                 105                 110

Val Thr Leu Arg Cys Gln Thr Lys Leu His Pro Leu Arg Ser Ala Leu
                            115                 120                 125

Arg Leu Leu Phe Ser Phe His Lys Asp Gly His Thr Leu Gln Asp Arg
                    130                 135                 140

Gly Pro His Pro Glu Leu Cys Ile Pro Gly Ala Lys Glu Gly Asp Ser
             145                 150                 155                 160

Gly Leu Tyr Trp Cys Glu Val Ala Pro Glu Gly Gly Gln Val Gln Lys
                                165                 170                 175

Gln Ser Pro Gln Leu Glu Val Arg Val Gln Ala Pro Val Ser Arg Pro
                            180                 185                 190

Val Leu Thr Leu His His Gly Pro Ala Asp Pro Ala Val Gly Asp Met
                            195                 200                 205

Val Gln Leu Leu Cys Glu Ala Gln Arg Gly Ser Pro Pro Ile Leu Tyr
                    210                 215                 220

Ser Phe Tyr Leu Asp Glu Lys Ile Val Gly Asn His Ser Ala Pro Cys
             225                 230                 235                 240

Gly Gly Thr Thr Ser Leu Leu Phe Pro Val Lys Ser Glu Gln Asp Ala
                                245                 250                 255

Gly Asn Tyr Ser Cys Glu Ala Glu Asn Ser Val Ser Arg Glu Arg Ser
                            260                 265                 270

Glu Pro Lys Lys Leu Ser Leu Lys Gly Ser Gln Val Leu Phe Thr Pro
                            275                 280                 285

Ala Ser Asn
                    290

<210> SEQ ID NO 28
<211> LENGTH: 419
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 28

Lys Thr Val Trp Leu Tyr Leu Gln Ala Trp Pro Asn Pro Val Phe Glu
             1                   5                  10                  15

Gly Asp Ala Leu Thr Leu Arg Cys Gln Gly Trp Lys Asn Thr Pro Leu
                            20                  25                  30

Ser Gln Val Lys Phe Tyr Arg Asp Gly Lys Phe Leu His Phe Ser Lys
                        35                  40                  45

Glu Asn Gln Thr Leu Ser Met Gly Ala Ala Thr Val Gln Ser Arg Gly
                    50                  55                  60
```

-continued

```
Gln Tyr Ser Cys Ser Gly Gln Val Met Tyr Ile Pro Gln Thr Phe Thr
 65                  70                  75                  80

Gln Thr Ser Glu Thr Ala Met Val Gln Val Gln Glu Leu Phe Pro Pro
                 85                  90                  95

Pro Val Leu Ser Ala Ile Pro Ser Pro Glu Pro Arg Glu Gly Ser Leu
            100                 105                 110

Val Thr Leu Arg Cys Gln Thr Lys Leu His Pro Leu Arg Ser Ala Leu
            115                 120                 125

Arg Leu Leu Phe Ser Phe His Lys Asp Gly His Thr Leu Gln Asp Arg
        130                 135                 140

Gly Pro His Pro Glu Leu Cys Ile Pro Gly Ala Lys Glu Gly Asp Ser
145                 150                 155                 160

Gly Leu Tyr Trp Cys Glu Val Ala Pro Glu Gly Gly Gln Val Gln Lys
                165                 170                 175

Gln Ser Pro Gln Leu Glu Val Arg Val Gln Ala Pro Val Ser Arg Pro
            180                 185                 190

Val Leu Thr Leu His His Gly Pro Ala Asp Pro Ala Val Gly Asp Met
            195                 200                 205

Val Gln Leu Leu Cys Glu Ala Gln Arg Gly Ser Pro Pro Ile Leu Tyr
        210                 215                 220

Ser Phe Tyr Leu Asp Glu Lys Ile Val Gly Asn His Ser Ala Pro Cys
225                 230                 235                 240

Gly Gly Thr Thr Ser Leu Leu Phe Pro Val Lys Ser Glu Gln Asp Ala
                245                 250                 255

Gly Asn Tyr Ser Cys Glu Ala Glu Asn Ser Val Ser Arg Glu Arg Ser
            260                 265                 270

Glu Pro Lys Lys Leu Ser Leu Lys Gly Ser Gln Val Leu Phe Thr Pro
            275                 280                 285

Ala Ser Asn Trp Leu Val Pro Trp Leu Pro Ala Ser Leu Leu Gly Leu
        290                 295                 300

Met Val Ile Ala Ala Ala Leu Leu Val Tyr Val Arg Ser Trp Arg Lys
305                 310                 315                 320

Ala Gly Pro Leu Pro Ser Gln Ile Pro Pro Thr Ala Pro Gly Gly Glu
                325                 330                 335

Gln Cys Pro Leu Tyr Ala Asn Val His His Gln Lys Gly Lys Asp Glu
            340                 345                 350

Gly Val Val Tyr Ser Val Val His Arg Thr Ser Lys Arg Ser Glu Ala
            355                 360                 365

Arg Ser Ala Glu Phe Thr Val Gly Arg Lys Asp Ser Ser Ile Ile Cys
        370                 375                 380

Ala Glu Val Arg Cys Leu Gln Pro Ser Glu Val Ser Ser Thr Glu Val
385                 390                 395                 400

Asn Met Arg Ser Arg Thr Leu Gln Glu Pro Leu Ser Asp Cys Glu Glu
                405                 410                 415

Val Leu Cys

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 29
```

```
Met Leu Pro Arg Leu Leu Leu Leu Ile Cys Ala Pro Leu Cys Glu Pro
  1               5                  10                  15
```

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 30

```
Met Leu Leu Trp Ser Leu Leu Val Ile Phe Asp Ala Val Thr Glu Gln
  1               5                  10                  15

Ala Asp Ser
```

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 31

```
Met Leu Leu Trp Leu Leu Leu Ile Leu Thr Pro Gly Arg Glu Gln
  1               5                  10                  15

Ser
```

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 32

```
Met Leu Leu Trp Thr Ala Val Leu Leu Phe Val Pro Cys Val Gly
  1               5                  10                  15
```

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 33

```
atgctgccga ggctgttgct gttgatctgt gctccactct gtgaacctgc c            51
```

<210> SEQ ID NO 34
<211> LENGTH: 1236
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 34

```
gagctgtttt tgatagccag cccctcccat cccacagagg ggagcccagt gaccctgacg    60
tgtaagatgc cctttctaca gagttcagat gcccagttcc agttctgctt tttcagagac   120
acccgggcct tgggcccagg ctggagcagc tcccccaagc tccagatcgc tgccatgtgg   180
```

```
aaagaagaca caggqtcata ctggtgcgag gcacagacaa tggcgtccaa agtcttgagg      240
agcaggagat cccagataaa tgtgcacagg gtccctgtcg ctgatgtgag cttggagact      300
cagcccccag gaggacaggt gatggaggga cacaggctgg tcctcatctg ctcagttgct      360
atgggcacag gagacatcac cttcctttgg tacaaggggc tgtaggtttt aaaccttcag      420
tcaaagaccc agcgttcact gacagcagag tatgagattc cttcagtgag ggagagtgat      480
gctgagcaat attactgtgt agctgaaaat ggctatggtc ccagcccag tgggctggtg       540 agcatcactg tcagaatccc ggtgtctcgc ccaatcctca tgctcagggc tcccagggcc      600
caggctgcag tggaggatgt gctggagctt cactgtgagg ccctgagagg ctctcctcca      660
atcctgtact ggttttatca cgaggatatc accctgggga gcaggtcggc cccctctgga      720
ggaggagcct ccttcaacct ttccctgact gaagaacatt ctggaaacta ctcctgtgag      780
gccaacaatg gcctgggggc ccagcgcagt gaggcggtga cactcaactt cacagtgcct      840
actgggccca gaagcaatca tcttacctca ggagtcattg aggggctgct cagcacccett     900 ggtccagcca ccgtggcctt attattttgc tacggcctca aaagaaaaat aggaagacgt      960
tcagccaggg atccactcag gagccttccc agccctctac cccaagagtt cacctacctc     1020
aactcaccta ccccagggca gctacagcct atatatgaaa atgtgaatgt tgtaagtggg     1080
gatgaggttt attcactggc gtactataac cagccggagc aggaatcagt agcagcagaa     1140
accctgggga cacatatgga ggacaaggtt tccttagaca tctattccag gctgaggaaa     1200
gcaaacatta cagatgtgga ctatgaagat gctatg                               1236

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 35
atgctgctgt ggtcattgct ggtcatcttt gatgcagtca ctgaacaggc agattcgctg       60

<210> SEQ ID NO 36
<211> LENGTH: 1464
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 36
acccttgtgg cgccctcttc tgtcttcgaa ggagacagca tcgttctgaa atgccaggga       60
gaacagaact ggaaaattca gaagatggct taccataagg ataacaaaga gttatctgtt      120
ttcaaaaaat tctcagattt ccttatccaa agtgcagttt aagtgacag tggtaactat       180 ttctgtagta ccaaaggaca actctttctc tgggataaaa cttcaaatat agtaaagata      240
aaagtccaag agctctttca acgtcctgtg ctgactgcca gctccttcca gcccatcgaa      300
gggggtccag tgagcctgaa atgtgagacc cggctctctc cacagaggtt ggatgttcaa      360
ctccagttct gcttcttcag agaaaaccag gtcctgggt caggctggag cagctctccg      420
gagctccaga tttctgccgt gtggagtgaa gacacagggt cttactggtg caaggcagaa      480
acggtgactc acaggatcag aaaacagagc ctccaatccc agattcacgt gcagagaatc      540
cccatctcta atgtaagctt ggagatccgg gccccgggg acaggtgac tgaaggacaa        600
```

```
aaactgatcc tgctctgctc agtggctggg ggtacaggaa atgtcacatt ctcctggtac    660
agagaggcca caggaaccag tatgggaaag aaaacccagc gttccctgtc agcagagctg    720
gagatcccag ctgtgaaaga gagtgatgcc ggcaaatatt actgtagagc tgacaacggc    780
catgtgccta tccagagcaa ggtggtgaat atccctgtga aattccagt gtctcgccct     840 gtcctcaccc tcaggtctcc tggggcccag gctgcagtgg gggacctgct ggagcttcac    900
tgtgaggccc tgagaggctc tcccccaatc ttgtaccaat tttatcatga ggatgtcacc    960
cttgggaaca gctcggcccc ctctggagga ggggcctcct tcaacctctc tttgactgca    1020
gaacattctg gaaactactc ctgtgaggcc aacaacggcc tggggcccca gtgcagtgag    1080
gcagtgccag tctccatctc aggacctgat ggctatagaa gagacctcat gacagctgga    1140
gttctctggg gactgtttgg tgtccttggt ttcactggtg ttgctttgct gttgtatgcc    1200
ttgttccaca agatatcagg agaaagttct gccactaatg aacccagagg ggcttccagg    1260
ccaaatcctc aagagttcac ctattcaagc ccaaccccag acatggagga gctgcagcca    1320
gtgtatgtca atgtgggctc tgtagatgtg gatgtggttt attctcaggt ctggagcatg    1380
cagcagccag aaagctcagc aaacatcagg acacttctgg agaacaagga ctcccaagtc    1440
atctactctt ctgtgaagaa atca                                           1464
```

<210> SEQ ID NO 37
<211> LENGTH: 54
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 37

```
atgcttctgt ggctgctgct gctgatcctg actcctggaa gagaacaatc aggg          54
```

<210> SEQ ID NO 38
<211> LENGTH: 2148
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 38

```
gtggccccaa aagctgtact tctcctcaat cctccatggt ccacagcctt caaaggagaa    60
aaagtggctc tcatatgcag cagcatatca cattccctag cccagggaga cacatattgg    120
tatcacgatg agaagttgtt gaaaataaaa catgacaaga tccaaattac agagcctgga    180
aattaccaat gtaagacccg aggatcctcc ctcagtgatg ccgtgcatgt ggaattttca    240
cccgactggc tgatcctgca ggctttacat cctgtctttg aaggagacaa tgtcattctg    300
agatgtcagg ggaaagacaa caaaaacact catcaaaagg tttactacaa ggatggaaaa    360
cagcttccta atagttataa tttagagaag atcacagtga attcagtctc agggataat    420 agcaaatatc attgtactgc ttataggaag ttttacatac ttgacattga agtaacttca    480
aaacccctaa atatccaagt tcaagagctg tttctacatc ctgtgctgag agccagctct    540
tccacgccca tagaggggag tcccatgacc ctgacctgtg agacccagct ctctccacag    600
aggccagatg tccagctgca attctccctc ttcagagata gccagaccct cggattgggc    660
tggagcaggt cccccagact ccagatccct gccatgtgga ctgaagactc aggtcttac    720
```

```
tggtgtgagg tggagacagt gactcacagc atcaaaaaaa ggagcctgag atctcagata        780
cgtgtacaga gagtccctgt gtctaatgtg aatctagaga tccggcccac cggagggcag        840
ctgattgaag gagaaaatat ggtccttatt tgctcagtag cccagggttc agggactgtc        900
acattctcct ggcacaaaga aggaagagta agaagcctgg gtagaaagac ccagcgttcc        960
ctgttggcag agctgcatgt tctcaccgtg aaggagagtg atgcaggag atactactgt       1020 gcagctgata acgttcacag ccccatcctc agcacgtgga ttcgagtcac cgtgagaatt      1080
ccggtatctc accctgtcct caccttcagg gctcccaggg cccacactgt ggtgggggac      1140
ctgctggagc ttcactgtga gtccctgaga ggctctcccc cgatcctgta ccgattttat      1200
catgaggacg tcaccctggg gaacagctca gcccctctg gaggaggagc ctccttcaac       1260
ctctctctga ctgcagaaca ttctggaaac tactcctgtg atgcagacaa tggcctgggg      1320
gcccagcaca gtcatggagt gagtctcagg gtcacagttc cggtgtctcg ccccgtcctc      1380
accctcaggc ctcccggggc ccaggctgtg gtgggggacc tgctggagct tcactgtgag      1440
tccctgagag gctccttccc gatcctgtac tggttttatc acgaggatga caccttgggg      1500
aacatctcgg cccactctgg aggagggca tccttcaacc tctctctgac tacagaacat       1560
tctggaaact actcatgtga ggctgacaat ggcctggggg cccagcacag taaagtggtg      1620
acactcaatg ttacaggaac ttccaggaac agaacaggcc ttaccgctgc gggaatcacg      1680
gggctggtgc tcagcatcct cgtccttgct gctgctgctg ctctgctgca ttacgccagg      1740
gcccgaagga aaccaggagg actttctgcc actggaacat ctagtcacag tcctagcgag      1800
tgtcaggagc cttcctcgtc caggccttcc aggatagacc ctcaagagcc cactcactct      1860
aaaccactag ccccaatgga gctggagcca atgtacagca atgcaaatcc tggagatagc      1920
aacccgattt attcccagat ctggagcatc cagcatacaa aagaaaactc agctaattgt      1980
ccaatgatgc atcaagagca tgaggaactt acagtcctct attcagaact gaagaagaca      2040
cacccagacg actctgcagg ggaggctagc agcagaggca gggcccatga agaagatgat      2100
gaagaaaact atgagaatgt accacgtgta ttactggcct cagaccac                   2148
```

<210> SEQ ID NO 39
<211> LENGTH: 48
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 39

```
atgctgctct ggacggctgt gctgctcttt gttccctgtg ttgggaaa                     48
```

<210> SEQ ID NO 40
<211> LENGTH: 2003
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 40

```
aggtctggtt gctctctgcc ggcttcgccc tgacctgttt ctgacctgtg ttccctccgc         60
tgtgccagaa caggccccat gctgctctgg acggctgtgc tgctctttgt tccctgtgtt        120
gggaaaactg tctggctgta cctccaagcc tggccaaacc ctgtgtttga aggagatgcc        180
ctgactctgc gatgtcaggg atggaagaat acaccactgt ctcaggtgaa gttctacaga        240
```

```
gatggaaaat tccttcattt ctctaaggaa aaccagactc tgtccatggg agcagcaaca    300
gtgcagagcc gtggccagta cagctgctct gggcaggtga tgtatattcc acagacattc    360
acacaaactt cagagactgc catggttcaa gtccaagagc tgtttccacc tcctgtgctg    420
agtgccatcc cctctcctga gccccgagag gtagcctgg tgaccctgag atgtcagaca     480
aagctgcacc ccctgaggtc agccttgagg ctccttttct ccttccacaa ggacggccac    540
accttgcagg acaggggccc tcacccagaa ctctgcatcc cgggagccaa ggagggagac    600
tctgggcttt actggtgtga ggtggcccct gagggtggcc aggtccagaa gcagagcccc    660
cagctggagg tcagagtgca ggctcctgta tcccgtcctg tgctcactct gcaccacggg    720
cctgctgacc ctgctgtggg ggacatggtg cagctcctct gtgaggcaca gagggctcc     780 cctccgatcc tgtattcctt ctaccttgat gagaagattg tggggaacca ctcagctccc    840
tgtggtggaa ccacctccct cctcttccca gtgaagtcag aacaggatgc tgggaactac    900
tcctgcgagg ctgagaacag tgtctccaga gagaggagtg agcccaagaa gctgtctctg    960
aagggttctc aagtcttgtt cactcccgcc agcaactggc tggttccttg gcttcctgcg    1020
agcctgcttg gcctgatggt tattgctgct gcacttctgg tttatgtgag atcctggaga    1080
aaagctgggc cccttccatc ccagatacca cccacagctc caggtggaga gcagtgccca    1140
ctatatgcca acgtgcatca ccagaaaggg aaagatgaag tgttgtcta ctctgtggtg     1200 catagaacct caaagaggag tgaagccagg tctgctgagt tcaccgtggg gagaaaggac    1260
agttctatca tctgtgcgga ggtgagatgc ctgcagccca gtgaggtttc atccacggag    1320
gtgaatatga aagcaggac tctccaagaa cccttagcg actgtgagga ggttctctgc      1380
tagtgatggt gttctcctat caacacacgc ccaccccag tctccagtgc tcctcaggaa     1440
gacagtgggg tcctcaactc tttctgtggg tccttcagtt cccaagccca gcatcacaga    1500 gcccctgag cccttgtcct ggtcaggagc acctgaaccc tgggttcttt tcttagcaga     1560
agaccaacca atggaatggg aagggagatg ctcccaccaa cacacacact taggttcaat    1620
cagtgacact ggacacataa gccacagatg tcttcttcc atacaagcat gttagttcgc     1680
cccaatatac atatatatat gaaatagtca tgtgccgcat aacaacatt cagtcagtga     1740 tagactgcat acacaacagt ggtcccataa gactgtaatg gagtttaaaa attcctactg    1800
cctagtgata tcatagttgc cttaacatca taacacaaca catttctcac gcgtttgtgg    1860
tgatgctggt acaaacaagc tacagcgccg ctagtcatat acaaatatag cacatacaat    1920
tatgtacagt acactatact tgataatgat aataaacaac tatgttactg gtctaaaaaa    1980
aaaaaaaaaa aaaaaaaaaa aaa                                            2003
```

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 41

```
tgagtctcag ggtcacagtt ccg                                             23
```

<210> SEQ ID NO 42
<211> LENGTH: 26
<212> TYPE: DNA
<213> ORGANISM: Artificial Sequence

```
<220> FEATURE:
<223> OTHER INFORMATION: Description of Artificial Sequence:/note =
      synthetic construct

<400> SEQUENCE: 42
gctcttgaac ttggatattt agggt                                          26

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 43
ccagtgtatg tcaatgtggg ctctg                                          25

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 44
cgttgaaaga gctcttggac ttttatc                                        27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 45
gcctcaaaag aaaaatagga agacgtt                                        27

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 46
aagctcacat cagcgacagg gac                                            23

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 47
tcttggagat aagtcgggct tt                                             22

<210> SEQ ID NO 48
<211> LENGTH: 25
<212> TYPE: DNA
<213> ORGANISM: Artificial Sequence
<220> FEATURE:
```

<223> OTHER INFORMATION: Description of Artificial Sequence:/note =
      synthetic construct

<400> SEQUENCE: 48
atcctgcagc ccagcctcgt aggag                                      25

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 49
ggtcctcatg ctgctgtggt catt                                       24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 50
gctgttgatc ttcccttctg attc                                       24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 51
atgctgccga ggctgttgct gttg                                       24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 52
catagcatct tcatagtcca catc                                       24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 53
ctcaacttca cagtgcctac tggg                                       24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 54
tcctgcagag tcactaacct tgag                                        24

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 55
ccagtgtatg tcaatgtggg ctctg                                       25

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 56
cattcttccc tcaaatcttt acac                                        24

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 57
cagcacgtgg attcgagtca c                                           21

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 58
cagatctggg aataaatcgg gttg                                        24

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 59
tcttcagaga tggcgaggtc a                                           21

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence:/note =
      synthetic construct

```
<400> SEQUENCE: 60
ttttggggtg tacatcaaca tacaag                                      26

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 61
tgttgccctg tttcttccaa taca                                        24

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 62
cagagttggc cgacctacgc                                             20

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence:/note =
      synthetic construct
<220> FEATURE:
<221> NAME/KEY: VARIANT
<222> LOCATION: 5, 15, 17, 22, 28
<223> OTHER INFORMATION: X can be any amino acid

<400> SEQUENCE: 63

Gly Glu Pro Ile Xaa Leu Arg Cys His Ser Trp Lys Asp Lys Xaa Leu
 1               5                  10                  15

Xaa Lys Val Thr Tyr Xaa Gln Asn Gly Lys Ala Xaa Lys Phe Phe His
             20                  25                  30

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence:/note =
      synthetic construct
<220> FEATURE:
<221> NAME/KEY: VARIANT
<222> LOCATION: 1
<223> OTHER INFORMATION: Xaa can be either Glu or Asp
<220> FEATURE:
<221> NAME/KEY: VARIANT
<222> LOCATION: 7
<223> OTHER INFORMATION: Xaa can be either Leu or Ile
<220> FEATURE:
<221> NAME/KEY: VARIANT
<222> LOCATION: 17
<223> OTHER INFORMATION: Xaa can be either Leu or Ile
<220> FEATURE:
<221> NAME/KEY: VARIANT
<222> LOCATION: 2, 3, 5, 6, 8-13, 15-16
<223> OTHER INFORMATION: Xaa can be any amino acid

<400> SEQUENCE: 64
```

```
Xaa Xaa Xaa Tyr Xaa Xaa Xaa Xaa Xaa Xaa Xaa Xaa Xaa Xaa Tyr Xaa
1               5                   10                  15

Xaa
```

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence:/note =
      synthetic construct
<220> FEATURE:
<221> NAME/KEY: VARIANT
<222> LOCATION: 1
<223> OTHER INFORMATION: Xaa can be either Glu or Asp
<220> FEATURE:
<221> NAME/KEY: VARIANT
<222> LOCATION: 7
<223> OTHER INFORMATION: Xaa can be either Leu or Ile
<220> FEATURE:
<221> NAME/KEY: VARIANT
<222> LOCATION: 18
<223> OTHER INFORMATION: Xaa can be either Leu or Ile
<220> FEATURE:
<221> NAME/KEY: VARIANT
<222> LOCATION: 2, 3, 5, 6, 8-14, 16-17
<223> OTHER INFORMATION: Xaa can be any amino acid

<400> SEQUENCE: 65

```
Xaa Xaa Xaa Tyr Xaa Xaa Xaa Xaa Xaa Xaa Xaa Xaa Xaa Xaa Xaa Tyr
1               5                   10                  15

Xaa Xaa
```

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence:/note =
      synthetic construct
<220> FEATURE:
<221> NAME/KEY: VARIANT
<222> LOCATION: 1
<223> OTHER INFORMATION: Xaa can be either Glu or Asp
<220> FEATURE:
<221> NAME/KEY: VARIANT
<222> LOCATION: 7
<223> OTHER INFORMATION: Xaa can be either Leu or Ile
<220> FEATURE:
<221> NAME/KEY: VARIANT
<222> LOCATION: 19
<223> OTHER INFORMATION: Xaa can be either Leu or Ile
<220> FEATURE:
<221> NAME/KEY: VARIANT
<222> LOCATION: 2, 3, 5, 6, 8-16, 18
<223> OTHER INFORMATION: Xaa can be any amino acid

<400> SEQUENCE: 66

```
Xaa Xaa Xaa Tyr Xaa Xaa Xaa Xaa Xaa Xaa Xaa Xaa Xaa Xaa Xaa Xaa
1               5                   10                  15

Tyr Xaa Xaa
```

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence:/note =
      synthetic construct
<220> FEATURE:
<221> NAME/KEY: VARIANT
<222> LOCATION: 1
<223> OTHER INFORMATION: Xaa can be either Ile orVal or Leu or Ser
<220> FEATURE:
<221> NAME/KEY: VARIANT
<222> LOCATION: 2, 4, 5
<223> OTHER INFORMATION: Xaa can be any amino acid
<220> FEATURE:
<221> NAME/KEY: VARIANT
<222> LOCATION: 6
<223> OTHER INFORMATION: Xaa can be Leu or Val

<400> SEQUENCE: 67

Xaa Xaa Tyr Xaa Xaa Xaa
 1               5

<210> SEQ ID NO 68
<211> LENGTH: 492
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 68

Asp Trp Leu Ser Ile Ser Leu Pro His Arg Ser Tyr Glu Gly Asp Gln
 1               5                  10                  15

Val Val Ile Ser Cys Thr Gly Lys Asn Asn Gly Asp Ile Lys Arg Leu
            20                  25                  30

Lys Tyr Phe Lys Asp Gly Tyr His Ile Glu Thr Tyr Ser Ser Ala Ser
        35                  40                  45

Ser Tyr Thr Ile Arg Asn Ala Arg Arg Gly Asp Ser Gly Ser Tyr Ser
    50                  55                  60

Cys Lys Ala Asp Arg Lys Phe Phe Leu Phe Ile Asp Thr Thr Glu Glu
65                  70                  75                  80

Thr Gly Ser Lys Trp Leu Asn Val Gln Glu Leu Phe Pro Ala Pro Gly
                85                  90                  95

Leu Thr Ala Ser Pro Leu Gln Pro Val Glu Gly Ser Ser Val Thr Leu
            100                 105                 110

Ser Cys Asn Thr Trp Leu Pro Ser Asp Arg Ala Thr Thr Gln Leu Arg
        115                 120                 125

Tyr Ser Phe Phe Lys Asp Gly His Thr Leu Gln Ser Gly Trp Thr Ser
    130                 135                 140

Ser Lys Phe Thr Ile Ser Ala Ile Ser Lys Glu Asp Ser Gly Asn Tyr
145                 150                 155                 160

Trp Cys Glu Ala Met Thr Ala Ser Arg Ser Val Ser Lys Gln Ser His
                165                 170                 175

Arg Ser Tyr Ile Asp Val Glu Arg Ile Pro Val Ser Gln Val Thr Met
            180                 185                 190

Glu Ile Gln Pro Ser Arg Gly Trp Gly Val Glu Gly Glu Pro Leu Val
        195                 200                 205

Val Glu Gly Glu Pro Leu Val Leu Ala Cys Ser Val Ala Lys Gly Thr
    210                 215                 220

Gly Leu Ile Thr Phe Ser Trp His Arg Gln Thr Lys Glu Ser Val
225                 230                 235                 240

Gly Lys Lys Ser Gln Arg Ser Gln Arg Val Glu Leu Glu Ile Pro Thr
                245                 250                 255

Ile Arg Glu Ser His Ala Gly Gly Tyr Tyr Cys Thr Ala Asp Asn Asn
            260                 265                 270

Tyr Gly Leu Ile Gln Ser Ala Ile Val Asn Ile Thr Val Lys Ile Pro

```
                275                 280                 285
Val Leu Asn Pro Leu Leu Ser Ile Ser Val Pro Gly Val Leu Pro Phe
        290                 295                 300

Ile Gly Asp Val Ala Glu Leu His Cys Glu Asp Lys Arg Ala Ser Pro
305                 310                 315                 320

Pro Val Leu Tyr Trp Phe Tyr His Glu Asn Ile Thr Leu Ala Asn Thr
                325                 330                 335

Ser Ala Pro Phe Gly Gly Lys Ala Ser Phe Lys Leu Ser Leu Thr Ala
            340                 345                 350

Gly His Ser Gly Asn Tyr Ser Cys Glu Ala Glu Asn Ala Trp Gly Thr
        355                 360                 365

Lys Arg Ser Glu Val Val Thr Leu Asn Val Thr Glu Pro Pro Pro Lys
370                 375                 380

Val Arg Leu Val Asn Gly Pro His His Cys Glu Gly Arg Val Glu Val
385                 390                 395                 400

Glu Gln Glu Gly Arg Trp Gly Thr Val Cys Asp Asp Gly Trp Asp Met
                405                 410                 415

Arg Asp Val Ala Val Val Cys Arg Glu Leu Gly Cys Gly Ala Ala Gln
            420                 425                 430

His Thr Pro Ile Ala Met Leu Tyr Pro Pro Ala Val Asp Glu Ala Leu
        435                 440                 445

Pro Val Leu Ile Gln Val Ala Leu Cys Asn Gly Thr Glu Lys Thr Leu
    450                 455                 460

Ala Glu Cys Asp Gln Val Glu Ala Phe Asp Cys Gly His Asp Glu Asp
465                 470                 475                 480

Ala Gly Ala Val Cys Glu Val Leu Pro Ser Thr Phe
                485                 490

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 69

Met Pro Leu Cys Leu Leu Leu Leu Val Phe Ala Pro Val Gly Val Gln
1               5                   10                  15

Ser

<210> SEQ ID NO 70
<211> LENGTH: 383
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 70

Asp Trp Leu Ser Ile Ser Leu Pro His Arg Ser Tyr Glu Gly Asp Gln
1               5                   10                  15

Val Val Ile Ser Cys Thr Gly Lys Asn Asn Gly Asp Ile Lys Arg Leu
            20                  25                  30

Lys Tyr Phe Lys Asp Gly Tyr His Ile Glu Thr Tyr Ser Ser Ala Ser
        35                  40                  45

Ser Tyr Thr Ile Arg Asn Ala Arg Arg Gly Asp Ser Gly Ser Tyr Ser
    50                  55                  60
```

-continued

Cys Lys Ala Asp Arg Lys Phe Phe Leu Phe Ile Asp Thr Thr Glu Glu
65                  70                  75                  80

Thr Gly Ser Lys Trp Leu Asn Val Gln Glu Leu Phe Pro Ala Pro Gly
            85                  90                  95

Leu Thr Ala Ser Pro Leu Gln Pro Val Glu Gly Ser Ser Val Thr Leu
            100                 105                 110

Ser Cys Asn Thr Trp Leu Pro Ser Asp Arg Ala Thr Thr Gln Leu Arg
            115                 120                 125

Tyr Ser Phe Phe Lys Asp Gly His Thr Leu Gln Ser Gly Trp Thr Ser
        130                 135                 140

Ser Lys Phe Thr Ile Ser Ala Ile Ser Lys Glu Asp Ser Gly Asn Tyr
145                 150                 155                 160

Trp Cys Glu Ala Met Thr Ala Ser Arg Ser Val Ser Lys Gln Ser His
                165                 170                 175

Arg Ser Tyr Ile Asp Val Glu Arg Ile Pro Val Ser Gln Val Thr Met
            180                 185                 190

Glu Ile Gln Pro Ser Arg Gly Trp Gly Val Glu Gly Glu Pro Leu Val
        195                 200                 205

Val Glu Gly Glu Pro Leu Val Leu Ala Cys Ser Val Ala Lys Gly Thr
210                 215                 220

Gly Leu Ile Thr Phe Ser Trp His Arg Gln Asp Thr Lys Glu Ser Val
225                 230                 235                 240

Gly Lys Lys Ser Gln Arg Ser Gln Arg Val Glu Leu Glu Ile Pro Thr
            245                 250                 255

Ile Arg Glu Gly His Ala Gly Gly Tyr Tyr Cys Thr Ala Asp Asn Asn
            260                 265                 270

Tyr Gly Leu Ile Gln Ser Ala Ile Val Asn Ile Thr Val Lys Ile Pro
        275                 280                 285

Val Leu Asn Pro Leu Leu Ser Ile Ser Val Pro Gly Val Leu Pro Phe
290                 295                 300

Ile Gly Asp Val Ala Glu Leu His Cys Glu Asp Lys Arg Ala Ser Pro
305                 310                 315                 320

Pro Val Leu Tyr Trp Phe Tyr His Glu Asn Ile Thr Leu Ala Asn Thr
            325                 330                 335

Ser Ala Pro Phe Gly Lys Ala Ser Phe Lys Leu Ser Leu Thr Ala
        340                 345                 350

Gly His Ser Gly Asn Tyr Ser Cys Glu Ala Glu Asn Ala Trp Gly Thr
        355                 360                 365

Lys Arg Ser Glu Val Val Thr Leu Asn Val Thr Gly Arg Thr Ile
370                 375                 380

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 71

Met Pro Leu Cys Leu Leu Leu Leu Val Phe Ala Pro Val Gly Val Gln
1               5                   10                  15

Ser

<210> SEQ ID NO 72

```
<211> LENGTH: 17
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 72

Met Leu Pro Trp Leu Leu Leu Ile Cys Ala Leu Pro Cys Glu Pro
 1               5                  10                  15

Ala

<210> SEQ ID NO 73
<211> LENGTH: 326
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 73

Gly Ile Ser Asp Val Ser Leu Lys Thr Arg Pro Pro Gly Gly Trp Val
 1               5                  10                  15

Met Glu Gly Asp Lys Leu Val Leu Ile Cys Ser Val Asp Arg Val Thr
             20                  25                  30

Gly Asn Ile Thr Tyr Phe Trp Tyr Arg Gly Ala Leu Gly Phe Gln Leu
         35                  40                  45

Glu Thr Lys Thr Gln Pro Ser Leu Thr Ala Glu Phe Glu Ile Ser Asp
     50                  55                  60

Met Lys Gln Ser Asp Ala Asp Gln Tyr Tyr Cys Ala Ala Asn Asp Gly
 65                  70                  75                  80

His Asp Pro Ile Ala Ser Glu Leu Val Ser Ile His Val Arg Val Pro
                 85                  90                  95

Val Ser Arg Pro Val Leu Thr Phe Gly Asp Ser Gly Thr Gln Ala Val
            100                 105                 110

Leu Gly Asp Leu Val Glu Leu His Cys Lys Ala Leu Arg Gly Ser Pro
        115                 120                 125

Pro Ile Phe Tyr Gln Phe Tyr His Glu Ser Ile Ile Leu Gly Asn Ser
    130                 135                 140

Ser Ala Pro Ser Gly Gly Gly Ala Ser Phe Asn Phe Ser Leu Thr Ala
145                 150                 155                 160

Glu His Ser Gly Asn Phe Ser Cys Glu Ala Ser Asn Gly Gln Gly Ala
                165                 170                 175

Gln Arg Ser Glu Val Val Ala Leu Asn Leu Thr Gly Leu Ser Leu Val
            180                 185                 190

Pro Thr Glu Asn Gly Ile Ser His Leu Ser Leu Gly Leu Thr Gly Trp
        195                 200                 205

Leu Leu Gly Cys Leu Ser Pro Ile Thr Met Ala Leu Ile Phe Cys Tyr
    210                 215                 220

Trp Leu Lys Arg Lys Ile Gly Arg Gln Ser Glu Asp Pro Val Arg Ser
225                 230                 235                 240

Pro Pro Gln Thr Val Leu Gln Gly Ser Thr Tyr Pro Lys Ser Pro Asp
                245                 250                 255

Ser Arg Gln Pro Glu Pro Leu Tyr Glu Asn Val Asn Val Val Ser Gly
            260                 265                 270

Asn Glu Val Tyr Ser Leu Val Tyr His Thr Pro Gln Val Leu Glu Pro
        275                 280                 285
```

```
Ala Ala Ala Gln His Val Arg Thr His Gly Val Ser Glu Ser Phe Gln
    290                 295                 300

Val Ser Ser Gly Leu Tyr Ser Lys Pro Arg Ile Asn Ile Ala His Met
305                 310                 315                 320

Asp Tyr Glu Asp Ala Met
                325

<210> SEQ ID NO 74
<211> LENGTH: 203
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 74

Gly Ile Ser Asp Val Ser Leu Lys Thr Arg Pro Gly Gly Trp Val
1               5                   10                  15

Met Glu Gly Asp Lys Leu Val Leu Ile Cys Ser Val Asp Arg Val Thr
                20                  25                  30

Gly Asn Ile Thr Tyr Phe Trp Tyr Arg Gly Ala Leu Gly Phe Gln Leu
            35                  40                  45

Glu Thr Lys Thr Gln Pro Ser Leu Thr Ala Glu Phe Glu Ile Ser Asp
    50                  55                  60

Met Lys Gln Ser Asp Ala Asp Gln Tyr Tyr Cys Ala Ala Asn Asp Gly
65                  70                  75                  80

His Asp Pro Ile Ala Ser Glu Leu Val Ser Ile His Val Arg Val Pro
                85                  90                  95

Val Ser Arg Pro Val Leu Thr Phe Gly Asp Ser Gly Thr Gln Ala Val
            100                 105                 110

Leu Gly Asp Leu Val Glu Leu His Cys Lys Ala Leu Arg Gly Ser Pro
        115                 120                 125

Pro Ile Phe Tyr Gln Phe Tyr His Glu Ser Ile Ile Leu Gly Asn Ser
    130                 135                 140

Ser Ala Pro Ser Gly Gly Ala Ser Phe Asn Phe Ser Leu Thr Ala
145                 150                 155                 160

Glu His Ser Gly Asn Phe Ser Cys Glu Ala Ser Asn Gly Gln Gly Ala
                165                 170                 175

Gln Arg Ser Glu Val Val Ala Leu Asn Leu Thr Gly Leu Ser Leu Val
            180                 185                 190

Pro Thr Glu Asn Gly Ile Ser His Leu Ser Leu
        195                 200

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 75

Met Leu Pro Trp Leu Leu Leu Leu Ile Cys Ala Leu Pro Cys Glu Pro
1               5                   10                  15

Ala

<210> SEQ ID NO 76
<211> LENGTH: 100
<212> TYPE: PRT
```

```
<213> ORGANISM: Artificial Sequence
<220> FEATURE:
<223> OTHER INFORMATION: Description of Artificial Sequence:/note =
      synthetic construct

<400> SEQUENCE: 76

Lys Arg Lys Ile Gly Arg Gln Ser Glu Asp Pro Val Arg Ser Pro Pro
 1               5                  10                  15

Gln Thr Val Leu Gln Gly Ser Thr Tyr Pro Lys Ser Pro Asp Ser Arg
            20                  25                  30

Gln Pro Glu Pro Leu Tyr Glu Asn Val Asn Val Val Ser Gly Asn Glu
        35                  40                  45

Val Tyr Ser Leu Val Tyr His Thr Pro Gln Val Leu Glu Pro Ala Ala
    50                  55                  60

Ala Gln His Val Arg Thr His Gly Val Ser Glu Ser Phe Gln Val Ser
65                  70                  75                  80

Ser Gly Leu Tyr Ser Lys Pro Arg Ile Asn Ile Ala His Met Asp Tyr
                85                  90                  95

Glu Asp Ala Met
            100

<210> SEQ ID NO 77
<211> LENGTH: 283
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 77

Gly Ile Ser Asp Val Ser Leu Lys Thr Arg Pro Pro Gly Gly Trp Val
 1               5                  10                  15

Met Glu Gly Asp Lys Leu Val Leu Ile Cys Ser Val Asp Arg Val Thr
            20                  25                  30

Gly Asn Ile Thr Tyr Phe Trp Tyr Arg Gly Ala Leu Gly Phe Gln Leu
        35                  40                  45

Glu Thr Lys Thr Gln Pro Ser Leu Thr Ala Glu Phe Glu Ile Ser Asp
    50                  55                  60

Met Lys Gln Ser Asp Ala Asp Gln Tyr Tyr Cys Ala Ala Asn Asp Gly
65                  70                  75                  80

His Asp Pro Ile Ala Ser Glu Leu Val Ser Ile His Val Arg Val Pro
                85                  90                  95

Val Ser Arg Pro Val Leu Thr Phe Gly Asp Ser Gly Thr Gln Ala Val
            100                 105                 110

Leu Gly Asp Leu Val Glu Leu His Cys Lys Ala Leu Arg Gly Ser Pro
        115                 120                 125

Pro Ile Phe Tyr Gln Phe Tyr His Glu Ser Ile Ile Leu Gly Asn Ser
    130                 135                 140

Ser Ala Pro Ser Gly Gly Ala Ser Phe Asn Phe Ser Leu Thr Ala
145                 150                 155                 160

Glu His Ser Gly Asn Phe Ser Cys Glu Ala Ser Asn Gly Gln Gly Ala
                165                 170                 175

Gln Arg Ser Glu Val Val Ala Leu Asn Leu Thr Gly Arg Gln Ser Glu
            180                 185                 190

Asp Pro Val Arg Ser Pro Gln Thr Val Leu Gln Gly Ser Thr Tyr
        195                 200                 205

Pro Lys Ser Pro Asp Ser Arg Gln Pro Glu Pro Leu Tyr Glu Asn Val
```

```
                    210                 215                 220
Asn Val Val Ser Gly Asn Glu Val Tyr Ser Leu Val Tyr His Thr Pro
225                 230                 235                 240

Gln Val Leu Glu Pro Ala Ala Gln His Val Arg Thr His Gly Val
                245                 250                 255

Ser Glu Ser Phe Gln Val Ser Ser Gly Leu Tyr Ser Lys Pro Arg Ile
                260                 265                 270

Asn Ile Ala His Met Asp Tyr Glu Asp Ala Met
                275                 280

<210> SEQ ID NO 78
<211> LENGTH: 570
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 78

Gly Gln His Glu Ala Ala Gln Gln Ser Val Val Ser Leu Gln Pro Pro
1               5                   10                  15

Trp Thr Thr Phe Phe Arg Gly Glu Val Val Thr Leu Thr Cys Tyr Arg
                20                  25                  30

Phe Gly Phe Ser Val Pro Gln Lys Thr Lys Trp Tyr Gln Lys Arg Lys
                35                  40                  45

Thr Val Lys Gln Thr Pro Gly Ala Leu Val Ile Lys Ala His Thr Leu
            50                  55                  60

Lys Val His Glu Ser Gly Glu Tyr Trp Cys Gln Ala Asp Ser Leu Leu
65                  70                  75                  80

Pro Ser Met His Val Asn Val Glu Phe Ser Glu Asp Phe Leu Val Leu
                85                  90                  95

Gln Ala Pro Pro Ala Val Phe Glu Gly Asp Ser Val Val Leu Arg Cys
                100                 105                 110

Tyr Ala Lys Lys Gly Ile Glu Ala Glu Thr Leu Thr Phe Tyr Lys Asp
                115                 120                 125

Gly Lys Ala Leu Thr Leu His His Gln Ser Glu Leu Ser Ile His His
            130                 135                 140

Ala Asn Leu Lys Asp Asn Gly Gln Tyr Lys Cys Thr Ser Lys Lys Lys
145                 150                 155                 160

Trp Ser Phe Gly Ser Leu Tyr Thr Ser Asn Thr Val Gly Val Gln Val
                165                 170                 175

Gln Glu Leu Phe Pro Arg Pro Val Leu Arg Ala Arg Pro Ser His Pro
                180                 185                 190

Ile Asp Gly Ser Pro Val Thr Leu Thr Cys Gln Thr Gln Leu Ser Ala
            195                 200                 205

Gln Lys Ser Asp Ala Arg Leu Gln Phe Cys Phe Phe Arg Asn Leu Gln
            210                 215                 220

Leu Leu Gly Ser Gly Cys Ser Arg Ser Ser Glu Phe His Ile Pro Ala
225                 230                 235                 240

Ile Trp Thr Glu Glu Ser Arg Arg Tyr Gln Cys Lys Ala Glu Thr Val
                245                 250                 255

Asn Ser Gln Val Arg Lys Gln Ser Thr Ala Phe Ile Ile Pro Val Gln
                260                 265                 270

Arg Ala Ser Ala Arg Phe Gln Thr His Ile Ile Pro Ala Ser Lys Leu
                275                 280                 285
```

```
Val Phe Glu Gly Gln Leu Leu Leu Asn Cys Ser Val Lys Gly Val
    290                 295                 300
Pro Gly Pro Leu Lys Phe Ser Trp Tyr Lys Lys Asp Met Leu Asn Glu
305                 310                 315                 320
Glu Thr Lys Ile Leu Lys Ser Ser Asn Ala Glu Phe Lys Ile Ser Gln
                325                 330                 335
Val Asn Ile Ser Asp Ala Gly Glu Tyr His Cys Glu Ala Thr Asn Ser
            340                 345                 350
Arg Arg Ser Phe Val Ser Arg Ala Phe Pro Ile Thr Ile Lys Val Pro
        355                 360                 365
Val Ser Gln Pro Val Leu Thr Leu Ser Thr Gly Lys Thr Gln Ala Leu
    370                 375                 380
Glu Gly Asp Leu Met Thr Leu His Cys Gln Ser Gln Arg Gly Ser Pro
385                 390                 395                 400
Cys Ile Leu Tyr Glu Phe Phe Tyr Glu Asn Val Ser Leu Gly Asn Ser
                405                 410                 415
Ser Ile Leu Ser Gly Gly Gly Ala Tyr Phe Asn Phe Ser Met Ser Thr
            420                 425                 430
Glu Arg Ser Gly Asn Tyr Tyr Cys Thr Ala Asp Asn Gly Leu Gly Ala
        435                 440                 445
Gln Cys Ser Glu Ala Ile Arg Ile Ser Ile Phe Asp Met Thr Lys Asn
    450                 455                 460
Arg Ser Val Pro Met Ala Ala Gly Ile Thr Val Gly Leu Leu Ile Met
465                 470                 475                 480
Ala Val Gly Val Phe Leu Phe Tyr Cys Trp Phe Ser Arg Lys Ala Gly
                485                 490                 495
Gly Lys Pro Thr Ser Asp Asp Ser Arg Asn Pro Ser Asp Ser Glu Pro
            500                 505                 510
Gln Glu Pro Thr Tyr Tyr Asn Val Pro Ala Cys Ile Glu Leu Gln Pro
        515                 520                 525
Val Tyr Ser Asn Glu Pro Glu Glu Asn Val Ile Tyr Thr Glu Val Arg
    530                 535                 540
Arg Thr Gln Pro Arg Gln Lys His Ala Asp Gln Glu Ser Glu Ser Pro
545                 550                 555                 560
Arg Ser Arg Cys Gln Met Ala Glu Lys Lys
                565                 570

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 79

Met Ser Gly Ser Phe Ser Pro Cys Val Val Phe Thr Gln Met Trp Leu
1               5                   10                  15
Thr Leu Leu Val Val Thr Pro Val Asn
            20                  25

<210> SEQ ID NO 80
<211> LENGTH: 468
<212> TYPE: PRT
<213> ORGANISM: Artificial Sequence
<220> FEATURE:
<223> OTHER INFORMATION: Description of Artificial Sequence:/note =
      synthetic construct
```

```
<400> SEQUENCE: 80

Gly Gln His Glu Ala Ala Gln Gln Ser Val Val Ser Leu Gln Pro Pro
 1               5                  10                  15
Trp Thr Thr Phe Phe Arg Gly Glu Val Val Thr Leu Thr Cys Tyr Arg
            20                  25                  30
Phe Gly Phe Ser Val Pro Gln Lys Thr Lys Trp Tyr Gln Lys Arg Lys
        35                  40                  45
Thr Val Lys Gln Thr Pro Gly Ala Leu Val Ile Lys Ala His Thr Leu
    50                  55                  60
Lys Val His Glu Ser Gly Glu Tyr Trp Cys Gln Ala Asp Ser Leu Leu
65                  70                  75                  80
Pro Ser Met His Val Asn Val Glu Phe Ser Glu Asp Phe Leu Val Leu
                85                  90                  95
Gln Ala Pro Pro Ala Val Phe Glu Gly Asp Ser Val Val Leu Arg Cys
            100                 105                 110
Tyr Ala Lys Lys Gly Ile Glu Ala Glu Thr Leu Thr Phe Tyr Lys Asp
        115                 120                 125
Gly Lys Ala Leu Thr Leu His His Gln Ser Glu Leu Ser Ile His His
    130                 135                 140
Ala Asn Leu Lys Asp Asn Gly Gln Tyr Lys Cys Thr Ser Lys Lys Lys
145                 150                 155                 160
Trp Ser Phe Gly Ser Leu Tyr Thr Ser Asn Thr Val Gly Val Gln Val
                165                 170                 175
Gln Glu Leu Phe Pro Arg Pro Val Leu Arg Ala Arg Pro Ser His Pro
            180                 185                 190
Ile Asp Gly Ser Pro Val Thr Leu Thr Cys Gln Thr Gln Leu Ser Ala
        195                 200                 205
Gln Lys Ser Asp Ala Arg Leu Gln Phe Cys Phe Phe Arg Asn Leu Gln
    210                 215                 220
Leu Leu Gly Ser Gly Cys Ser Arg Ser Ser Glu Phe His Ile Pro Ala
225                 230                 235                 240
Ile Trp Thr Glu Glu Ser Arg Arg Tyr Gln Cys Lys Ala Glu Thr Val
                245                 250                 255
Asn Ser Gln Val Arg Lys Gln Ser Thr Ala Phe Ile Ile Pro Val Gln
            260                 265                 270
Arg Ala Ser Ala Arg Phe Gln Thr His Ile Ile Pro Ala Ser Lys Leu
        275                 280                 285
Val Phe Glu Gly Gln Leu Leu Leu Asn Cys Ser Val Lys Gly Val
    290                 295                 300
Pro Gly Pro Leu Lys Phe Ser Trp Tyr Lys Lys Asp Met Leu Asn Glu
305                 310                 315                 320
Glu Thr Lys Ile Leu Lys Ser Ser Asn Ala Glu Phe Lys Ile Ser Gln
                325                 330                 335
Val Asn Ile Ser Asp Ala Gly Glu Tyr His Cys Glu Ala Thr Asn Ser
            340                 345                 350
Arg Arg Ser Phe Val Ser Arg Ala Phe Pro Ile Thr Ile Lys Val Pro
        355                 360                 365
Val Ser Gln Pro Val Leu Thr Leu Ser Thr Gly Lys Thr Gln Ala Leu
    370                 375                 380
Glu Gly Asp Leu Met Thr Leu His Cys Gln Ser Gln Arg Gly Ser Pro
385                 390                 395                 400
Cys Ile Leu Tyr Glu Phe Phe Tyr Glu Asn Val Ser Leu Gly Asn Ser
```

```
                405                 410                 415
Ser Ile Leu Ser Gly Gly Gly Ala Tyr Phe Asn Phe Ser Met Ser Thr
            420                 425                 430

Glu Arg Ser Gly Asn Tyr Tyr Cys Thr Ala Asp Asn Gly Leu Gly Ala
        435                 440                 445

Gln Cys Ser Glu Ala Ile Arg Ile Ser Ile Phe Asp Met Thr Lys Asn
    450                 455                 460

Arg Ser Val Pro
465

<210> SEQ ID NO 81
<211> LENGTH: 79
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 81

Ser Arg Lys Ala Gly Gly Lys Pro Thr Ser Asp Asp Ser Arg Asn Pro
1               5                   10                  15

Ser Asp Ser Glu Pro Gln Glu Pro Thr Tyr Tyr Asn Val Pro Ala Cys
            20                  25                  30

Ile Glu Leu Gln Pro Val Tyr Ser Asn Glu Pro Glu Asn Val Ile
        35                  40                  45

Tyr Thr Glu Val Arg Arg Thr Gln Pro Arg Gln Lys His Ala Asp Gln
    50                  55                  60

Glu Ser Glu Ser Pro Arg Ser Arg Cys Gln Met Ala Glu Lys Lys
65                  70                  75

<210> SEQ ID NO 82
<211> LENGTH: 1973
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 82
ccacagtgtt ctatcccaga tccgtggtcc atctgcccta aggacttgag ctgcacctgt      60
ctcaaaggga gctacttgcc tctagtctca tgcctctgtg cttgctgctt ctggtcttcg     120
ctcctgtcgg agtccagtcc gactggttga gcatcagcct tccacaccgt tcttatgaag    180
gagaccaagt agttataagc tgcacaggaa aaaataatgg tgacataaag agactgaagt    240
acttcaagga tggatatcac atagaaactt acagcagtgc ttcaagctac accattagga    300
atgcaagacg tggtgacagt ggctcctatt cctgtaaggc agataggaaa ttttttcctat   360 ttatagacac aacagaagaa acaggatcta agtggctgaa tgtccaagag ctgtttccag    420
cacctgggct gacagccagc cccctgcagc ccgtagaggg gagttcagtg accctgtcct    480
gcaacacctg gctcccttca gatagggcaa cgacccagct acgctattcc ttcttcaaag    540
atggccacac tttgcaatcg ggctggacct catcaaaatt taccatctca gcaatatcga    600
aggaagactc aggaaattac tggtgtgaag caatgactgc ctctcgcagt gtctcaaagc    660
agagtcaccg gtcctacata gatgtagaga ggatccctgt atctcaagtc accatggaaa    720 tccagcctte aaggggctgg ggagttgaag gggagccact ggtcgttgaa ggggagcccc    780
tggtcctggc ttgttctgtg gctaaaggca ccgggctaat cacgttctcc tggcataggc    840
```

-continued

| | |
|---|---|
| aggacactaa ggaaagtgtg gggaagaaaa gtcagcgttc ccagagagtg gagctggaga | 900 |
| tccctactat cagggaaggc catgctgggg ggtactactg cacagcagac aacaactacg | 960 |
| gcctgatcca gagcgcaatc gtgaacatca ccgtgaaaat tccagtgttg aacccgctcc | 1020 |
| tctccatcag tgttcctggg gtcttgccct tcatcggaga tgtggcggag cttcactgtg | 1080 |
| aagacaagag agcatctcct ccggttctct actggtttta tcatgaaaat atcactctgg | 1140 |
| ctaacacctc ggcaccttt ggaggaaagg catcctttaa gctctctctg actgcagggc | 1200 |
| attctgggaa ctactcttgt gaggctgaaa cgcctgggg taccaagcgc agtgaggtgg | 1260 |
| taacgctcaa tgtcacagag ccccaccca aagtgcgttt ggtgaatggc ccccaccact | 1320 |
| gtgaaggacg cgtagaggtg gagcaggaag gtcgctgggg cactgtatgt gatgatggct | 1380 |
| gggacatgag ggatgtggct gtggtgtgcc gagagctggg ctgtggagca gcccaacaca | 1440 |
| cacctatagc catgctgtat ccaccagcag ttgatgaagc tctgcctgtg ctcattcagg | 1500 |
| tagccctgtg caatggcaca gaaaagaccc tggctgaatg tgaccaggtt gaggcctttg | 1560 |
| attgtggaca tgatgaggat gctggagctg tgtgtgaagt cttacccagc actttctgaa | 1620 |
| gatctagaga ccagagacca tcagacctcc tactttctgc actgggcctc acagccctca | 1680 |
| cggtctgcag ctcccagtgg acttccagac ttcagctgtg gcttatcctt caagaggact | 1740 |
| cgaaactata ttaatctgct ctgagataat gttccaacag ctccaaagaa agcccgagtc | 1800 |
| ccttgtcccc agaggccaag cttggaaaaa ttgttcccct gtccaggttc cctgcctttc | 1860 |
| tagttccttc ttgctatctc cttgggcaga tgcagaggtg gcacaagtaa ggatcacata | 1920 |
| catgtgcctg ggcttccatc tggtagaatg tggtctaaca aagcacatac aac | 1973 |

<210> SEQ ID NO 83
<211> LENGTH: 1530
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 83

| | |
|---|---|
| atgcctctgt gcttgctgct tctggtcttc gctcctgtcg gagtccagtc cgactggttg | 60 |
| agcatcagcc ttccacaccg ttcttatgaa ggagaccaag tagttataag ctgcacagga | 120 |
| aaaaataatg gtgacataaa gagactgaag tacttcaagg atggatatca catagaaact | 180 |
| tacagcagtg cttcaagcta caccattagg aatgcaagac gtggtgacag tggctcctat | 240 |
| tcctgtaagg cagataggaa atttttccta tttatagaca caacagaaga aacaggatct | 300 |
| aagtggctga atgtccaaga gctgtttcca gcacctgggc tgcagccag cccctgcag | 360 |
| cccgtagagg ggagttcagt gaccctgtcc tgcaacacct ggctcccttc agatagggca | 420 |
| acgacccagc tacgctattc cttcttcaaa gatggccaca ctttgcaatc gggctggacc | 480 |
| tcatcaaaat ttaccatctc agcaatatcg aaggaagact caggaaatta ctggtgtgaa | 540 |
| gcaatgactg cctctcgcag tgtctcaaag cagagtcacc ggtcctacat agatgtagag | 600 |
| aggatccctg tatctcaagt caccatggaa atccagcctt caaggggctg ggagttgaa | 660 |
| ggggagccac tggtcgttga aggggagccc ctggtcctgg cttgttctgt ggctaaaggc | 720 |
| accgggctaa tcacgttctc ctggcatagg caggacacta aggaaagtgt gggaagaaa | 780 |
| agtcagcgtt cccagagagt ggagctggag atccctacta tcaggaagg ccatgctggg | 840 |
| ggtactact gcacagcaga caacaactac ggcctgatcc agagcgcaat cgtgaacatc | 900 |

-continued

| | |
|---|---|
| accgtgaaaa ttccagtgtt gaacccgctc tctccatca gtgttcctgg ggtcttgccc | 960 |
| ttcatcggag atgtggcgga gcttcactgt gaagacaaga gagcatctcc tccggttctc | 1020 |
| tactggtttt atcatgaaaa tatcactctg gctaacacct cggcaccttt tggaggaaag | 1080 |
| gcatccttta agctctctct gactgcaggg cattctggga actactcttg tgaggctgaa | 1140 |
| aacgcctggg gtaccaagcg cagtgaggtg gtaacgctca atgtcacaga gcccccaccc | 1200 |
| aaagtgcgtt tggtgaatgg ccccaccac tgtgaaggac gctagaggt ggagcaggaa | 1260 |
| ggtcgctggg gcactgtatg tgatgatggc tgggacatga gggatgtggc tgtggtgtgc | 1320 |
| cgagagctgg gctgtggagc agcccaacac acacctatag ccatgctgta tccaccagca | 1380 |
| gttgatgaag ctctgcctgt gctcattcag gtagccctgt gcaatggcac agaaaagacc | 1440 |
| ctggctgaat gtgaccaggt tgaggccttt gattgtggac atgatgagga tgctggagct | 1500 |
| gtgtgtgaag tcttacccag cactttctga | 1530 |

<210> SEQ ID NO 84
<211> LENGTH: 1371
<212> TYPE: DNA
<213> ORGANISM: Artificial Sequence
<220> FEATURE:
<223> OTHER INFORMATION: Description of Artificial Sequence:/note =
    synthetic construct

<400> SEQUENCE: 84

| | |
|---|---|
| ccacagtgtt ctatcccaga tccgtggtcc atctgcccta aggacttgag ctgcacctgt | 60 |
| ctcaaaggga gctacttgcc tctagtctca tgcctctgtg cttgctgctt ctggtcttcg | 120 |
| ctcctgtcgg agtccagtcc gactggttga gcatcagcct tccacaccgt tcttatgaag | 180 |
| gagaccaagt agttataagc tgcacaggaa aaaataatgg tgcataaag agactgaagt | 240 |
| acttcaagga tggatatcac atagaaactt acagcagtgc ttcaagctac accattagga | 300 |
| atgcaagacg tggtgacagt ggctcctatt cctgtaaggc agataggaaa tttttcctat | 360 |
| ttatagacac aacagaagaa acaggatcta agtggctgaa tgtccaagag ctgtttccag | 420 |
| cacctgggct gacagccagc cccctgcagc ccgtagaggg gagttcagtg accctgtcct | 480 |
| gcaacacctg gctcccttca gatagggcaa cgacccagct acgctattcc ttcttcaaag | 540 |
| atggccacac tttgcaatcg ggctggacct catcaaaatt taccatctca gcaatatcga | 600 |
| aggaagactc aggaaattac tggtgtgaag caatgactgc ctctcgcagt gtctcaaagc | 660 |
| agagtcaccg gtcctacata gatgtagaga ggatccctgt atctcaagtc accatggaaa | 720 |
| tccagccttc aaggggctgg ggagttgaag gggagccact ggtcgttgaa ggggagcccc | 780 |
| tggtcctggc ttgttctgtg gctaaaggca ccgggctaat cacgttctcc tggcataggc | 840 |
| aggacactaa ggaaagtgtg gggaagaaaa gtcagcgttc ccagagagtg gagctggaga | 900 |
| tccctactat cagggaaggc catgctgggg ggtactactg cacagcagac aacaactacg | 960 |
| gcctgatcca gagcgcaatc gtgaacatca ccgtgaaaat tccagtgttg aacccgctcc | 1020 |
| tctccatcag tgttcctggg gtcttgccct catcggaga tgtggcggag cttcactgtg | 1080 |
| aagacaagag agcatctcct ccggttctct actggtttta tcatgaaaat atcactctgg | 1140 |
| ctaacacctc ggcacctttt ggaggaaagg catcctttaa gctctctctg actgcagggc | 1200 |
| attctgggaa ctactcttgt gaggctgaaa acgcctgggg taccaagcgc agtgaggtgg | 1260 |
| taacgctcaa tgtcacaggt aggacaattt aatgatccat tccagggtgc aacttgcctt | 1320 |
| ctggccatgc ccttcttctc tcccttgcac ctgtacctct tggtctttga a | 1371 |

<210> SEQ ID NO 85
<211> LENGTH: 1203
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 85

```
atgcctctgt gcttgctgct tctggtcttc gctcctgtcg gagtccagtc cgactggttg      60
agcatcagcc ttccacaccg ttcttatgaa ggagaccaag tagttataag ctgcacagga     120
aaaaataatg gtgacataaa gagactgaag tacttcaagg atggatatca catagaaact     180
tacagcagtg cttcaagcta caccattagg aatgcaagac gtggtgacag tggctcctat     240
tcctgtaagg cagataggaa attttttccta tttatagaca acagaagaa aacaggatct     300
aagtggctga atgtccaaga gctgtttcca gcacctgggc tgacagccag ccccctgcag     360
cccgtagagg ggagttcagt gaccctgtcc tgcaacacct ggctcccttc agatagggca     420
acgacccagc tacgctattc cttcttcaaa gatggccaca cttttgcaatc gggctggacc     480
tcatcaaaat ttaccatctc agcaatatcg aaggaagact caggaaatta ctggtgtgaa     540
gcaatgactg cctctcgcag tgtctcaaag cagagtcacc ggtcctacat agatgtagag     600
aggatccctg tatctcaagt caccatggaa atccagcctt caaggggctg gggagttgaa     660
ggggagccac tggtcgttga aggggagccc ctggtcctgg cttgttctgt ggctaaaggc     720
accgggctaa tcacgttctc ctggcatagg caggacacta aggaaagtgt ggggaagaaa     780
agtcagcgtt cccagagagt ggagctggag atccctacta tcagggaagg ccatgctggg     840
gggtactact gcacagcaga caacaactac ggcctgatcc agagcgcaat cgtgaacatc     900
accgtgaaaa ttccagtgtt gaacccgctc ctctccatca gtgttcctgg ggtcttgccc     960
ttcatcggag atgtggcgga gcttcactgt gaagacaaga gagcatctcc tccggttctc    1020
tactggtttt atcatgaaaa tatcactctg gctaacacct cggcaccttt tggaggaaag    1080
gcatccttta gctctctctct gactgcaggg cattctggga actactcttg tgaggctgaa    1140
aacgcctggg gtaccaagcg cagtgaggtg gtaacgctca atgtcacagg taggacaatt    1200
taa                                                                  1203
```

<210> SEQ ID NO 86
<211> LENGTH: 1479
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 86

```
gactggttga gcatcagcct tccacaccgt tcttatgaag gagaccaagt agttataagc      60
tgcacaggaa aaaataatgg tgacataaag agactgaagt acttcaagga tggatatcac     120
atagaaactt acagcagtgc ttcaagctac accattagga atgcaagacg tggtgacagt     180
ggctcctatt cctgtaaggc agataggaaa ttttttcctat ttatagacac aacagaagaa     240
acaggatcta agtggctgaa tgtccaagag ctgtttccag cacctgggct gacagccagc     300
cccctgcagc ccgtagaggg gagttcagtg accctgtcct gcaacacctg gctcccttca     360
gatagggcaa cgacccagct acgctattcc ttcttcaaag atggccacac tttgcaatcg     420
ggctggacct catcaaaatt taccatctca gcaatatcga aggaagactc aggaaattac     480
```

```
tggtgtgaag caatgactgc ctctcgcagt gtctcaaagc agagtcaccg gtcctacata      540
gatgtagaga ggatccctgt atctcaagtc accatggaaa tccagccttc aaggggctgg      600
ggagttgaag gggagccact ggtcgttgaa ggggagcccc tggtcctggc ttgttctgtg      660
gctaaaggca ccgggctaat cacgttctcc tggcataggc aggacactaa ggaaagtgtg      720
gggaagaaaa gtcagcgttc ccagagagtg gagctggaga tccctactat cagggaaggc      780
catgctgggg ggtactactg cacagcagac aacaactacg gcctgatcca gagcgcaatc      840
gtgaacatca ccgtgaaaat tccagtgttg aacccgctcc tctccatcag tgttcctggg      900
gtcttgccct tcatcggaga tgtggcggag cttcactgtg aagacaagag agcatctcct      960
ccggttctct actggtttta tcatgaaaat atcactctgg ctaacacctc ggcacctttt     1020
ggaggaaagg catcctttaa gctctctctg actgcagggc attctgggaa ctactcttgt     1080
gaggctgaaa acgcctgggg taccaagcgc agtgaggtgg taacgctcaa tgtcacagag     1140
cccccaccca aagtgcgttt ggtgaatggc ccccaccact gtgaaggacg cgtagaggtg     1200
gagcaggaag gtcgctgggg cactgtatgt gatgatggct gggacatgag ggatgtggct     1260
gtggtgtgcc gagagctggg ctgtggagca gcccaacaca cacctatagc catgctgtat     1320
ccaccagcag ttgatgaagc tctgcctgtg ctcattcagg tagccctgtg caatggcaca     1380
gaaaagaccc tggctgaatg tgaccaggtt gaggcctttg attgtggaca tgatgaggat     1440
gctggagctg tgtgtgaagt cttacccagc actttctga                           1479

<210> SEQ ID NO 87
<211> LENGTH: 1152
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 87
gactggttga gcatcagcct tccacaccgt tcttatgaag agaccaagt agttataagc        60 tgcacaggaa aaataatgg tgacataaag agactgaagt acttcaagga tggatatcac      120
atagaaactt acagcagtgc ttcaagctac accattagga atgcaagacg tggtgacagt      180
ggctcctatt cctgtaaggc agataggaaa ttttttccta tttatagacac aacagaagaa      240 acaggatcta agtggctgaa tgtccaagag ctgttccag cacctgggct gacagccagc       300
cccctgcagc ccgtagaggg gagttcagtg accctgtcct gcaacacctg gctcccttca      360
gatagggcaa cgacccagct acgctattcc ttcttcaaag atggccacac tttgcaatcg      420
ggctggacct catcaaaatt taccatctca gcaatatcga aggaagactc aggaaattac      480
tggtgtgaag caatgactgc ctctcgcagt gtctcaaagc agagtcaccg gtcctacata      540
gatgtagaga ggatccctgt atctcaagtc accatggaaa tccagccttc aaggggctgg      600
ggagttgaag gggagccact ggtcgttgaa ggggagcccc tggtcctggc ttgttctgtg      660
gctaaaggca ccgggctaat cacgttctcc tggcataggc aggacactaa ggaaagtgtg      720
gggaagaaaa gtcagcgttc ccagagagtg gagctggaga tccctactat cagggaaggc      780
catgctgggg ggtactactg cacagcagac aacaactacg gcctgatcca gagcgcaatc      840
gtgaacatca ccgtgaaaat tccagtgttg aacccgctcc tctccatcag tgttcctggg      900
gtcttgccct tcatcggaga tgtggcggag cttcactgtg aagacaagag agcatctcct      960
ccggttctct actggtttta tcatgaaaat atcactctgg ctaacacctc ggcacctttt     1020
```

```
ggaggaaagg catcctttaa gctctctctg actgcagggc attctgggaa ctactcttgt    1080
gaggctgaaa acgcctgggg taccaagcgc agtgaggtgg taacgctcaa tgtcacaggt    1140
aggacaattt aa                                                        1152

<210> SEQ ID NO 88
<211> LENGTH: 1567
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 88
tgagtagtct ggttttgctt ttttttcttt tggtgagagg taccttcaag ttaccatccc      60
cagcctggtc ctcatgctac cttggctcct gctactgatc tgtgctctac cgtgtgaacc    120
tgctggaatc tctgatgtga gcttgaagac acggccccca ggaggatggg tgatggaggg    180
agacaagctg gtcctcatct gctcggttga tagagtcact gggaatataa cttacttctg    240
gtacagaggg gccctgggtt ccaactggaa acaaagaca caaccttcac taacagcaga    300
gtttgagatc agtgacatga agcagagcga tgctgatcaa tattactgtg cggctaacga    360
tggccacgac cctatcgcca gtgagctggt gagcatccac gtcagagttc agtgtctcg    420 ccctgtcctt acgtttgggg actctggaac ccaggctgtg ctaggggacc tggtggagct    480
tcactgtaag gccctgagag gctcaccccc aatcttctac cagttttatc atgagagcat    540
catcctgggg aacagttcag caccctctgg aggaggagca tccttcaact ctccctgac    600 tgcagaacat tctggaaact tcctcctgtga ggccagcaat ggacagggtg cccaacgaag    660
tgaggtggtg gctctcaact taacaggtct ctccttagtg cctactgaga atggaatcag    720
ccatctctcc ttaggactca ctgggtggct gcttggctgt cttagcccca tcaccatggc    780
cttaatattt tgctactggc tcaagagaaa aataggaaga cagtcagagg atccagtcag    840
gagccctcct cagactgtgc tccaaggatc cacgtacccc aaatcccccg actcaaggca    900
gccagagccc ctgtatgaga acgtgaacgt tgtaagtggc aatgaagtgt actctctggt    960
gtaccacacc ccgcaggtgc tggaaccagc agcagctcag catgtgagga cacacggagt   1020
aagtgagtcc tttcaggtct cctctggact ctattctaag ccaaggataa acattgcaca   1080
tatggactat gaagacgcca tgtagaatta tgtaaacagc aactatggag tgctacatac   1140
aagcccaagg cctgatgtgg cctccaagga tactgggac agggatagct tgccagccca   1200
atttccccac acactgcggt tcattagatg agtccttcac ctaccctgtg tgaagctgga   1260
gcaagtcctg cagaaaccac ccaggaaaac caacttagac ggagaagcca gaagcatttg   1320
catctggttg ttgcccattc atgttggcac acgaactttt atttacagga ggaaaatggt   1380
gtgatgaaag caactaaggt cttacagcag agggacaatg cgactcagag agcacaaagc   1440
cgagatcaat ggctttgcag gtctgctgtg gagacagagc catgcttcct ctgtgcacat   1500 acccctagagt acttctgagt cactgccatc aacttagaat taaacacagt tgcataaaat   1560
gtactgt                                                             1567

<210> SEQ ID NO 89
<211> LENGTH: 1032
<212> TYPE: DNA
<213> ORGANISM: Artificial Sequence
<220> FEATURE:
<223> OTHER INFORMATION: Description of Artificial Sequence:/note =
```

<400> SEQUENCE: 89

| | |
|---|---|
| atgctacctt ggctcctgct actgatctgt gctctaccgt gtgaacctgc tggaatctct | 60 |
| gatgtgagct tgaagacacg ccccccagga ggatgggtga tggagggaga caagctggtc | 120 |
| ctcatctgct cggttgatag agtcactggg aatataactt acttctggta cagaggggcc | 180 |
| ctgggtttcc aactggaaac aaagacacaa ccttcactaa cagcagagtt tgagatcagt | 240 |
| gacatgaagc agagcgatgc tgatcaatat tactgtgcgg ctaacgatgg ccacgaccct | 300 |
| atcgccagtg agctggtgag catccacgtc agagttccag tgtctcgccc tgtccttacg | 360 |
| tttggggact ctggaaccca ggctgtgcta ggggacctgg tggagcttca ctgtaaggcc | 420 |
| ctgagaggct caccccccaat cttctaccag ttttatcatg agagcatcat cctggggaac | 480 |
| agttcagcac cctctggagg aggagcatcc ttcaacttct ccctgactgc agaacattct | 540 |
| ggaaacttct cctgtgaggc agcaatgga cagggtgccc aacgaagtga ggtggtggct | 600 |
| ctcaacttaa caggtctctc cttagtgcct actgagaatg gaatcagcca tctctcctta | 660 |
| ggactcactg ggtggctgct ggctgtgtctt agccccatca ccatggcctt aatattttgc | 720 |
| tactggctca agagaaaaat aggaagacag tcagaggatc cagtcaggag ccctcctcag | 780 |
| actgtgctcc aaggatccac gtaccccaaa tccccgact caaggcagcc agagcccctg | 840 |
| tatgagaacg tgaacgttgt aagtggcaat gaagtgtact ctctggtgta ccacaccccg | 900 |
| caggtgctgg aaccagcagc agctcagcat gtgaggacac acggagtaag tgagtccttt | 960 |
| caggtctcct ctggactcta ttctaagcca aggataaaca ttgcacatat ggactatgaa | 1020 |
| gacgccatgt ag | 1032 |

<210> SEQ ID NO 90
<211> LENGTH: 981
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 90

| | |
|---|---|
| ggaatctctg atgtgagctt gaagacacgg ccccaggag gatgggtgat ggagggagac | 60 |
| aagctggtcc tcatctgctc ggttgataga gtcactggga atataactta cttctggtac | 120 |
| agaggggccc tgggtttcca actggaaaca aagacacaac cttcactaac agcagagttt | 180 |
| gagatcagtg acatgaagca gagcgatgct gatcaatatt actgtgcggc taacgatggc | 240 |
| cacgacccta tcgccagtga gctggtgagc atccacgtca gagttccagt gtctcgccct | 300 |
| gtccttacgt ttggggactc tggaacccag gctgtgctag gggacctggt ggagcttcac | 360 |
| tgtaaggccc tgagaggctc accccaatc ttctaccagt tttatcatga gagcatcatc | 420 |
| ctggggaaca gttcagcacc ctctggagga ggagcatcct tcaacttctc cctgactgca | 480 |
| gaacattctg gaaacttctc ctgtgaggcc agcaatggac agggtgccca acgaagtgag | 540 |
| gtggtggctc tcaacttaac aggtctctcc ttagtgccta ctgagaatgg aatcagccat | 600 |
| ctctccttag gactcactgg gtggctgctt ggctgtctta gccccatcac catggcctta | 660 |
| atattttgct actggctcaa gagaaaaata ggaagacagt cagaggatcc agtcaggagc | 720 |
| cctcctcaga ctgtgctcca aggatccacg taccccaaat ccccgactc aaggcagcca | 780 |
| gagcccctgt atgagaacgt gaacgttgta agtggcaatg aagtgtactc tctggtgtac | 840 |

```
cacaccccgc aggtgctgga accagcagca gctcagcatg tgaggacaca cggagtaagt      900
gagtcctttc aggtctcctc tggactctat tctaagccaa ggataaacat tgcacatatg      960
gactatgaag acgccatgta g                                                981
```

<210> SEQ ID NO 91
<211> LENGTH: 660
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 91

```
atgctacctt ggctcctgct actgatctgt gctctaccgt gtgaacctgc tggaatctct       60
gatgtgagct tgaagacacg gccccccagga ggatgggtga tggagggaga caagctggtc     120
ctcatctgct cggttgatag agtcactggg aatataactt acttctggta cagaggggcc     180
ctgggtttcc aactggaaac aaagacacaa ccttcactaa cagcagagtt tgagatcagt     240
gacatgaagc agagcgatgc tgatcaatat tactgtgcgg ctaacgatgg ccacgaccct     300
atcgccagtg agctggtgag catccacgtc agagttccag tgtctcgccc tgtccttacg     360
tttggggact ctggaaccca ggctgtgcta ggggacctgg tggagcttca ctgtaaggcc     420
ctgagaggct caccccccaat cttctaccag ttttatcatg agagcatcat cctggggaac     480
agttcagcac cctctggagg aggagcatcc ttcaacttct ccctgactgc agaacattct     540
ggaaacttct cctgtgaggc agcaatggac agggtgccc aacgaagtga ggtggtggct     600
ctcaacttaa caggtctctcc cttagtgcct actgagaatg gaatcagcca tctctcctta     660
```

<210> SEQ ID NO 92
<211> LENGTH: 609
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 92

```
ggaatctctg atgtgagctt gaagacacgg ccccccaggag gatgggtgat ggagggagac      60
aagctggtcc tcatctgctc ggttgataga gtcactggga atataactta cttctggtac     120 agagggggccc tgggtttcca actggaaaca aagacacaac cttcactaac agcagagttt     180
gagatcagtg acatgaagca gagcgatgct gatcaatatt actgtgcggc taacgatggc     240
cacgacccta tcgccagtga gctggtgagc atccacgtca gagttccagt gtctcgccct     300
gtccttacgt ttggggactc tggaacccag gctgtgctag gggacctggt ggagcttcac     360
tgtaaggccc tgagaggctc acccccaatc ttctaccagt tttatcatga gagcatcatc     420
ctggggaaca gttcagcacc ctctggagga ggagcatcct tcaacttctc cctgactgca     480
gaacattctg gaaacttctc ctgtgaggcc agcaatggac agggtgccca acgaagtgag     540
gtggtggctc tcaacttaac aggtctctcc ttagtgccta ctgagaatgg aatcagccat     600
ctctcctta                                                              609
```

<210> SEQ ID NO 93
<211> LENGTH: 303
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 93

| | | | | | |
|---|---|---|---|---|---|
| aagagaaaaa | taggaagaca | gtcagaggat | ccagtcagga | gccctcctca | gactgtgctc | 60 |
| caaggatcca | cgtaccccaa | atcccccgac | tcaaggcagc | cagagcccct | gtatgagaac | 120 |
| gtgaacgttg | taagtggcaa | tgaagtgtac | tctctggtgt | accacacccc | gcaggtgctg | 180 |
| gaaccagcag | cagctcagca | tgtgaggaca | cacggagtaa | gtgagtcctt | tcaggtctcc | 240 |
| tctggactct | attctaagcc | aaggataaac | attgcacata | tggactatga | agacgccatg | 300 |
| tag | | | | | | 303 |

<210> SEQ ID NO 94
<211> LENGTH: 1567
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 94

| | | | | | |
|---|---|---|---|---|---|
| tgagtagtct | ggttttgctt | ttttttcttt | tggtgagagg | taccttcaag | ttaccatccc | 60 |
| cagcctggtc | ctcatgctac | cttggctcct | gctactgatc | tgtgctctac | cgtgtgaacc | 120 |
| tgctggaatc | tctgatgtga | gcttgaagac | acggccccca | ggaggatggg | tgatggaggg | 180 |
| agacaagctg | gtcctcatct | gctcggttga | tagagtcact | gggaatataa | cttacttctg | 240 |
| gtacagaggg | gccctgggtt | tccaactgga | acaaagaca | caaccttcac | taacagcaga | 300 |
| gtttgagatc | agtgacatga | agcagagcga | tgctgatcaa | tattactgtg | cggctaacga | 360 |
| tggccacgac | cctatcgcca | gtgagctggt | gagcatccac | gtcagagttc | cagtgtctcg | 420 |
| ccctgtcctt | acgtttgggg | actctggaac | ccaggctgtg | ctaggggacc | tggtggagct | 480 |
| tcactgtaag | gccctgagag | gctcacccc | aatcttctac | cagttttatc | atgagagcat | 540 |
| catcctgggg | aacagttcag | caccctctgg | aggaggagca | tccttcaact | tctccctgac | 600 |
| tgcagaacat | tctggaaact | tctcctgtga | ggccagcaat | ggacagggtg | cccaacgaag | 660 |
| tgaggtggtg | gctctcaact | taacaggtct | ctccttagtg | cctactgaga | atggaatcag | 720 |
| ccatctctcc | ttaggactca | ctgggtggct | gcttggctgt | cttagcccca | tcaccatggc | 780 |
| cttaatattt | tgctactggc | tcaagagaaa | aataggaaga | cagtcagagg | atccagtcag | 840 |
| gagccctcct | cagactgtgc | tccaaggatc | cacgtacccc | aaatcccccg | actcaaggca | 900 |
| gccagagccc | ctgtatgaga | acgtgaacgt | tgtaagtggc | aatgaagtgt | actctctggt | 960 |
| gtaccacacc | ccgcaggtgc | tggaaccagc | agcagctcag | catgtgagga | cacacggagt | 1020 |
| aagtgagtcc | tttcaggtct | cctctggact | ctattctaag | ccaaggataa | acattgcaca | 1080 |
| tatggactat | gaagacgcca | tgtagaatta | tgtaaacagc | aactatggag | tgctacatac | 1140 |
| aagcccaagg | cctgatgtgg | cctccaagga | tactgggac | agggatagct | tgccagccca | 1200 |
| atttccccac | acactgcggt | tcattagatg | agtccttcac | ctaccctgtg | tgaagctgga | 1260 |
| gcaagtcctg | cagaaaccac | ccaggaaaac | caacttagac | ggagaagcca | gaagcatttg | 1320 |
| catctggttg | ttgcccattc | atgttggcac | acgaactttt | atttacagga | ggaaaatggt | 1380 |
| gtgatgaaag | caactaaggt | cttacagcag | agggacaatg | cgactcagag | agcacaaagc | 1440 |
| cgagatcaat | ggctttgcag | gtctgctgtg | gagacagagc | catgcttcct | ctgtgcacat | 1500 |
| accctagagt | acttctgagt | cactgccatc | aacttagaat | taaacacagt | tgcataaaat | 1560 |

-continued

| | |
|---|---|
| gtactgt | 1567 |

<210> SEQ ID NO 95
<211> LENGTH: 903
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 95

| | |
|---|---|
| atgctacctt ggctcctgct actgatctgt gctctaccgt gtgaacctgc tggaatctct | 60 |
| gatgtgagct tgaagacacg gcccccagga ggatgggtga tggagggaga caagctggtc | 120 |
| ctcatctgct cggttgatag agtcactggg aatataactt acttctggta cagaggggcc | 180 |
| ctgggtttcc aactggaaac aaagacacaa ccttcactaa cagcagagtt tgagatcagt | 240 |
| gacatgaagc agagcgatgc tgatcaatat tactgtgcgg ctaacgatgg ccacgaccct | 300 |
| atcgccagtg agctggtgag catccacgtc agagttccag tgtctcgccc tgtccttacg | 360 |
| tttggggact ctggaaccca ggctgtgcta ggggacctgg tggagcttca ctgtaaggcc | 420 |
| ctgagaggct cacccccaat cttctaccag ttttatcatg agagcatcat cctggggaac | 480 |
| agttcagcac cctctggagg aggagcatcc ttcaacttct ccctgactgc agaacattct | 540 |
| ggaaacttct cctgtgaggc agcaatgga cagggtgccc aacgaagtga ggtggtggct | 600 |
| ctcaacttaa caggaagaca gtcagaggat ccagtcagga gccctcctca gactgtgctc | 660 |
| caaggatcca cgtaccccaa atcccccgac tcaaggcagc cagagcccct gtatgagaac | 720 |
| gtgaacgttg taagtggcaa tgaagtgtac tctctggtgt accacacccc gcaggtgctg | 780 |
| gaaccagcag cagctcagca tgtgaggaca cacggagtaa gtgagtcctt tcaggtctcc | 840 |
| tctggactct attctaagcc aaggataaac attgcacata tggactatga agacgccatg | 900 |
| tag | 903 |

<210> SEQ ID NO 96
<211> LENGTH: 852
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 96

| | |
|---|---|
| ggaatctctg atgtgagctt gaagacacgg cccccaggag gatgggtgat ggagggagac | 60 |
| aagctggtcc tcatctgctc ggttgataga gtcactggga atataactta cttctggtac | 120 |
| agaggggccc tgggtttcca actggaaaca aagacacaac cttcactaac agcagagttt | 180 |
| gagatcagtg acatgaagca gagcgatgct gatcaatatt actgtgcggc taacgatggc | 240 |
| cacgacccta tcgccagtga gctggtgagc atccacgtca gagttccagt gtctcgccct | 300 |
| gtccttacgt ttggggactc tggaacccag gctgtgctag ggacctggt ggagcttcac | 360 |
| tgtaaggccc tgagaggctc accccccaatc ttctaccagt tttatcatga gagcatcatc | 420 |
| ctggggaaca gttcagcacc ctctggagga ggagcatcct tcaacttctc cctgactgca | 480 |
| gaacattctg gaaacttctc ctgtgaggcc agcaatggac agggtgccca acgaagtgag | 540 |
| gtggtggctc tcaacttaac aggaagacag tcagaggatc cagtcaggag ccctcctcag | 600 |
| actgtgctcc aaggatccac gtaccccaaa tcccccgact caaggcagcc agagcccctg | 660 |
| tatgagaacg tgaacgttgt aagtggcaat gaagtgtact ctctggtgta ccacaccccg | 720 |

```
caggtgctgg aaccagcagc agctcagcat gtgaggacac acggagtaag tgagtcerttt    780 caggtctcct ctggactcta ttctaagcca aggataaaca ttgcacatat ggactatgaa    840
gacgccatgt ag                                                        852
```

<210> SEQ ID NO 97
<211> LENGTH: 2447
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 97

```
attcaagtta cactcaactg ttttagaaga gcagttcccc agatttctcc ttggagctgt     60
gagtgactac cattgcgagc aagagcaaga ggaaagcact acctgtgagc agatgtctgg    120
ttcattctca ccctgtgtgg tgttcacaca gatgtggctg actctactgg ttgtgactcc    180
tgtcaatgga cagcatgaag ctgcacagca gtctgtggtt tcccttcagc ctccatggac    240
cactttcttt cgaggagagg tcgtcacact gacttgttat agattcggct tctccgtacc    300
ccagaaaaca aaatggtacc agaaaagaaa aacagtgaag caaaccccag gtgctttggt    360
aattaaagca cataccttaa aggtccatga gtccggagag tattggtgcc aagccgacag    420
cttacttccg agcatgcacg tgaacgtaga gttttctgaa gattttctgg tgctgcaagc    480
tccacctgct gtgtttgaag agactctgt ggttctgagg tgctacgcaa agaaaggcat    540
agaagcagag accctgacat tttacaagga tggtaaagct ctgacattac atcatcaaag    600
tgagctctct attcatcatg caaatctgaa ggacaacggt caatacaaat gcacttcgaa    660
gaagaagtgg tcttttgggt ccctctatac ttccaatacg gtcggagttc aagtccaaga    720
gttgttccca cggcctgtgc tgagagccag ccctcccat ccatagatg gaagtccagt    780 gaccctgacg tgtcagaccc agctctctgc acagaagtca gatgcccggc tccagttctg    840
tttcttcaga aacctccagc ttctggggtc aggctgcagc cgctcctcag agttccacat    900
tcctgccata tggactgaag agtcaaggag ataccagtgc aaggcagaaa cagtgaattc    960
ccaagttaga aaacaaagta cagcgttcat aatcccagtg cagagagctt ctgcgagatt   1020
ccaaacacac atcatcccag cctcaaagtt ggtgtttgaa gggcagttgc tgttactcaa   1080
ctgctcagta aaaggagtyc caggrcccct caaattctcc tggtataaaa aggacatgct   1140
gaatgaagaa acaaagattc ttaagtcctc caacgcagaa ttcaagatct cccaggtgaa   1200
catcagtgac gcaggggagt atcactgtga agctaccaac agccgccgaa gctttgtcag   1260
cagggcattt cccatcacca taaagtccc agtatctcaa ccagttctca ccctaagcac   1320
aggcaagacc caggcccttg agggagactt gatgacactt cattgtcaat cccagagggg   1380
ctctccatgt atcctgtatg aattcttcta tgagaatgtc tccctgggga atagctctat   1440
actctctgga ggaggagcat acttcaattt ctctatgagc acagagcgat ctggaaacta   1500
ctactgcaca gcagacaatg gcctgggagc ccagtgcagt gaagctataa ggatctctat   1560
ctttgacatg acaagaacaa gaagtgttcc tatggctgcc ggaatcactg tgggactgct   1620
catcatggct gttggagtgt ttctgttta ttgctggtc tctagaaaag caggaggaaa   1680
gcctacctct gatgactcca gaaacccttc agattcagaa ccccaggagc ccacctatta   1740
caacgtacca gcctgtatag aactgcagcc agtgtacagc aatgagcctg aggaaaacgt   1800
gatttacaca gaagtacgga gaactcaacc aagacagaaa catgcagatc aggagtctga   1860
```

```
aagcccaaga tcaaggtgcc agatggctga gaaaaagtag gatatgtctc ctccaagaac    1920
agctccagaa aagaaacccg aagcttcgtc agtctaatct caccgatgct tctactgggc    1980
ctgcactttc ctacccacgg atggctccac agatcatgga cagcaaggaa atggccaact    2040
ctcctaagac tgggccaaca tccccatctt ctctttggtt tcccagagcc acgccacccc    2100
aaagtcagca ggaagttgca aaagatcaca acgaccctat tcctgttttg taaccacccc    2160
cagcctgaag caggctgagc cagaccttga ccttgctgcc actaaggaga ttacctaggg    2220
tggagcctgc ctctctagat cactctattg ttcagccact gccactgttc tccttcaaga    2280
cactgctacc tgctgggagg ccactgagct attccagaga ctacaccccta tcctgcacat    2340 catcacctgt agcctgttcc aggctccaag aatgaattgg cggcaatggg cctcccccct    2400 accccctta taagtgcatt tgccattaaa catttgggct ttgatct                   2447
```

<210> SEQ ID NO 98
<211> LENGTH: 1788
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 98

```
atgtctggtt cattctcacc ctgtgtggtg ttcacacaga tgtggctgac tctactggtt      60
gtgactcctg tcaatggaca gcatgaagct gcacagcagt ctgtggtttc ccttcagcct     120
ccatggacca cttctcttcg aggagaggtc gtcacactga cttgttatag attcggcttc     180
tccgtacccc agaaaacaaa atggtaccag aaaagaaaaa cagtgaagca aaccccaggt     240
gctttggtaa ttaaagcaca taccttaaag gtccatgagt ccggagagta ttggtgccaa     300
gccgacagct tacttccgag catgcacgtg aacgtagagt tttctgaaga ttttctggtg     360
ctgcaagctc cacctgctgt gttgaagga gactctgtgg ttctgaggtg ctacgcaaag     420
aaaggcatag aagcagagac cctgacattt tacaaggatg gtaaagctct gacattacat     480
catcaaagtg agctctctat tcatcatgca aatctgaagg acaacggtca atacaaatgc     540
acttcgaaga gaagtggtc ttttgggtcc ctctatactt ccaataccggt cggagttcaa     600 gtccaagagt tgttcccacg gcctgtgctg agagccagac cctcccatcc catagatgga     660
agtccagtga ccctgacgtg tcagacccag ctctctgcac agaagtcaga tgcccggctc     720
cagttctgtt tcttcagaaa cctccagctt ctggggtcag gctgcagccg ctcctcagag     780
tttcacattc ctgccatatg gactgaagag tcaaggagat accagtgcaa ggcagaaaca     840
gtgaattccc aagttagaaa acaaagtaca gcgttcataa tcccagtgca gagagcttct     900
gcgagattcc aaacacacat catcccagcc tcaaagttgg tgtttgaagg gcagttgctg     960
ttactcaact gctcagtaaa aggagtycca ggrccccctca aattctcctg gtataaaaag    1020
gacatgctga atgaagaaac aaagattctt aagtcctcca acgcagaatt caagatctcc    1080
caggtgaaca tcagtgacgc aggggagtat cactgtgaag ctaccaacag ccgccgaagc    1140
tttgtcagca gggcatttcc catcaccata aaagtcccag tatctcaacc agttctcacc    1200
ctaagcacag gcaagaccca ggcccttgag ggagacttga tgcacttca ttgtcaatcc    1260 cagagggggct ctccatgtat cctgtatgaa ttcttctatg agaatgtctc cctggggaat    1320
agctctatac tctctggagg aggagcatac ttcaatttct ctatgagcac agagcgatct    1380
ggaaactact actgcacagc agacaatggc ctgggagccc agtgcagtga agctataagg    1440
```

```
atctctatct tgacatgac aaagaacaga agtgttccta tggctgccgg aatcactgtg    1500
ggactgctca tcatggctgt tggagtgttt ctgttttatt gctggttctc tagaaaagca    1560
ggaggaaagc ctacctctga tgactccaga aacccttcag attcagaacc ccaggagccc    1620
acctattaca acgtaccagc ctgtatagaa ctgcagccag tgtacagcaa tgagcctgag    1680
gaaaacgtga tttacacaga agtacggaga actcaaccaa gacagaaaca tgcagatcag    1740
gagtctgaaa gcccaagatc aaggtgccag atggctgaga aaaagtag                 1788
```

<210> SEQ ID NO 99
<211> LENGTH: 1710
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 99

```
cagcatgaag ctgcacagca gtctgtggtt tcccttcagc ctccatggac cactttcttt      60
cgaggagagg tcgtcacact gacttgttat agattcggct tctccgtacc ccagaaaaca    120
aaatggtacc agaaaagaaa aacagtgaag caaaccccag gtgctttggt aattaaagca    180
cataccttaa aggtccatga gtccggagag tattggtgcc aagccgacag cttacttccg    240
agcatgcacg tgaacgtaga gttttctgaa gattttctgg tgctgcaagc tccacctgct    300
gtgtttgaag gagactctgt ggttctgagg tgctacgcaa agaaaggcat agaagcagag    360
accctgacat tttacaagga tggtaaagct ctgacattac atcatcaaag tgagctctct    420
attcatcatg caaatctgaa ggacaacggt caatacaaat gcacttcgaa gaagaagtgg    480
tcttttgggt ccctctatac ttccaatacg gtcggagttc aagtccaaga gttgttccca    540
cggcctgtgc tgagagccag accctcccat cccatagatg gaagtccagt gaccctgacg    600
tgtcagaccc agctctctgc acagaagtca gatgcccggc tccagttctg tttcttcaga    660
aacctccagc ttctggggtc aggctgcagc cgctcctcag agtttcacat tcctgccata    720
tggactgaag agtcaaggag ataccagtgc aaggcagaaa cagtgaattc ccaagttaga    780
aaacaaagta cagcgttcat aatcccagtg cagagagctt ctgcgagatt ccaaacacac    840
atcatcccag cctcaaagtt ggtgtttgaa gggcagttgc tgttactcaa ctgctcagta    900
aaaggagtyc caggrccccct caaattctcc tggtataaaa aggacatgct gaatgaagaa    960
acaaagattc ttaagtcctc caacgcagaa ttcaagatct cccaggtgaa catcagtgac   1020 gcagggagt atcactgtga agctaccaac agccgccgaa gctttgtcag cagggcattt   1080
cccatcacca taaaagtccc agtatctcaa ccagttctca ccctaagcac aggcaagacc   1140
caggcccttg agggagactt gatgacactt cattgtcaat cccagagggg ctctccatgt   1200
atcctgtatg aattcttcta tgagaatgtc tccctgggga atagctctat actctctgga   1260
ggaggagcat acttcaattt ctctatgagc acagagcgat ctggaaacta ctactgcaca   1320
gcagacaatg gctgggagc ccagtgcagt gaagctataa ggatctctat ctttgacatg   1380
acaaagaaca gaagtgttcc tatggctgcc ggaatcactg tgggactgct catcatggct   1440
gttggagtgt ttctgtttta ttgctggttc tctagaaaag caggaggaaa gcctacctct   1500
gatgactcca gaaacccttc agattcagaa cccaggagc ccacctatta caacgtacca   1560
gcctgtatag aactgcagcc agtgtacagc aatgagcctg aggaaaacgt gatttacaca   1620
gaagtacgga gaactcaacc aagacagaaa catgcagatc aggagtctga aagcccaaga   1680
```

-continued tcaaggtgcc agatggctga gaaaaagtag                                    1710

<210> SEQ ID NO 100
<211> LENGTH: 1401
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 100
cagcatgaag ctgcacagca gtctgtggtt tcccttcagc ctccatggac cactttcttt      60
cgaggagagg tcgtcacact gacttgttat agattcggct tctccgtacc ccagaaaaca     120
aaatggtacc agaaaagaaa aacagtgaag caaaccccag gtgctttggt aattaaagca     180 catacccttaa aggtccatga gtccggagag tattggtgcc aagccgacag cttacttccg    240
agcatgcacg tgaacgtaga gttttctgaa gattttctgg tgctgcaagc tccacctgct    300
gtgtttgaag gagactctgt ggttctgagg tgctacgcaa agaaaggcat agaagcagag    360
accctgacat tttacaagga tggtaaagct ctgacattac atcatcaaag tgagctctct    420
attcatcatg caaatctgaa ggacaacggt caatacaaat gcacttcgaa gaagaagtgg    480
tcttttgggt ccctctatac ttccaatacg gtcggagttc aagtccaaga gttgttccca    540
cggcctgtgc tgagagccag accctcccat cccatagatg gaagtccagt gaccctgacg    600
tgtcagaccc agctctctgc acagaagtca gatgcccggc tccagttctg tttcttcaga    660
aacctccagc ttctggggtc aggctgcagc cgctcctcag agtttcacat tcctgccata    720
tggactgaag agtcaaggag ataccagtgc aaggcagaaa cagtgaattc ccaagttaga    780
aaacaaagta cagcgttcat aatcccagtg cagagagctt ctgcgagatt ccaaacacac    840
atcatcccag cctcaaagtt ggtgtttgaa gggcagttgc tgttactcaa ctgctcagta    900
aaaggagtyc caggrcccct caaattctcc tggtataaaa aggacatgct gaatgaagaa    960
acaaagattc ttaagtcctc caacgcagaa ttcaagatct cccaggtgaa catcagtgac   1020 gcagggagt atcactgtga agctaccaac agccgccgaa gctttgtcag cagggcattt   1080
cccatcacca taaagtccc agtatctcaa ccagttctca ccctaagcac aggcaagacc   1140
caggcccttg agggagactt gatgacactt cattgtcaat cccagagggg ctctccatgt   1200
atcctgtatg aattcttcta tgagaatgtc tccctgggga atagctctat actctctgga   1260
ggaggagcat acttcaattt ctctatgagc acagagcgat ctggaaacta ctactgcaca   1320
gcagacaatg gcctgggagc ccagtgcagt gaagctataa ggatctctat ctttgacatg   1380
acaaagaaca gaagtgttcc t                                             1401

<210> SEQ ID NO 101
<211> LENGTH: 1479
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 101
atgtctggtt cattctcacc ctgtgtggtg ttcacacaga tgtggctgac tctactggtt      60
gtgactcctg tcaatggaca gcatgaagct gcacagcagt ctgtggtttc ccttcagcct    120
ccatggacca ctttctttcg aggagaggtc gtcacactga cttgttatag attcggcttc    180

-continued

```
tccgtacccc agaaaacaaa atggtaccag aaaagaaaaa cagtgaagca aaccccaggt      240
gctttggtaa ttaaagcaca taccttaaag gtccatgagt ccggagagta ttggtgccaa      300
gccgacagct tacttccgag catgcacgtg aacgtagagt tttctgaaga tttctggtg      360 ctgcaagctc cacctgctgt gtttgaagga gactctgtgg ttctgaggtg ctacgcaaag      420
aaaggcatag aagcagagac cctgacattt tacaaggatg gtaaagctct gacattacat      480
catcaaagtg agctctctat tcatcatgca aatctgaagg acaacggtca atacaaatgc      540
acttcgaaga agaagtggtc ttttgggtcc ctctatactt ccaatacggt cggagttcaa      600
gtccaagagt tgttcccacg gcctgtgctg agagccagac cctcccatcc catagatgga      660
agtccagtga ccctgacgtg tcagacccag ctctctgcac agaagtcaga tgcccggctc      720
cagttctgtt tcttcagaaa cctccagctt ctggggtcag gctgcagccg ctcctcagag      780
tttcacattc ctgccatatg gactgaagag tcaaggagat accagtgcaa ggcagaaaca      840
gtgaattccc aagttagaaa acaaagtaca gcgttcataa tcccagtgca gagagcttct      900
gcgagattcc aaacacacat catcccagcc tcaaagttgg tgtttgaagg gcagttgctg      960
ttactcaact gctcagtaaa aggagtycca ggrcccctca aattctcctg gtataaaaag     1020
gacatgctga atgaagaaac aaagattctt aagtcctcca acgcagaatt caagatctcc     1080
caggtgaaca tcagtgacgc aggggagtat cactgtgaag ctaccaacag ccgccgaagc     1140
tttgtcagca gggcatttcc catcaccata aaagtcccag tatctcaacc agttctcacc     1200
ctaagcacag gcaagaccca ggcccttgag ggagacttga tgacacttca ttgtcaatcc     1260 cagagggct ctccatgtat cctgtatgaa ttcttctatg agaatgtctc cctggggaat     1320
agctctatac tctctggagg aggagcatac ttcaatttct ctatgagcac agagcgatct     1380
ggaaactact actgcacagc agacaatggc ctgggagccc agtgcagtga agctataagg     1440
atctctatct ttgacatgac aaagaacaga agtgttcct                              1479
```

<210> SEQ ID NO 102
<211> LENGTH: 240
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 102

```
tctagaaaag caggaggaaa gcctacctct gatgactcca gaaacccttc agattcagaa       60
ccccaggagc ccacctatta caacgtacca gcctgtatag aactgcagcc agtgtacagc      120
aatgagcctg aggaaaacgt gatttacaca gaagtacgga gaactcaacc aagacagaaa      180
catgcagatc aggagtctga aagcccaaga tcaaggtgcc agatggctga gaaaaagtag      240
```